(12) United States Patent
Li et al.

(10) Patent No.: US 11,497,769 B2
(45) Date of Patent: Nov. 15, 2022

(54) ANTI-CD19 ANTIBODIES

(71) Applicant: WuXi Biologics Ireland Limited, Dublin (IE)

(72) Inventors: Jing Li, Shanghai (CN); Jieying Liu, Shanghai (CN)

(73) Assignee: WuXi Biologics Ireland Limited, Dublin (IE)

( * ) Notice: Subject to any disclaimer, the term of this patent is extended or adjusted under 35 U.S.C. 154(b) by 201 days.

(21) Appl. No.: 16/649,157

(22) PCT Filed: Sep. 20, 2018

(86) PCT No.: PCT/CN2018/106619
§ 371 (c)(1),
(2) Date: Mar. 20, 2020

(87) PCT Pub. No.: WO2019/057100
PCT Pub. Date: Mar. 28, 2019

(65) Prior Publication Data
US 2020/0289563 A1    Sep. 17, 2020

(30) Foreign Application Priority Data
Sep. 21, 2017 (WO) ................ PCT/CN2017/102631

(51) Int. Cl.
*A61K 35/17* (2015.01)
*A61K 47/64* (2017.01)
(Continued)

(52) U.S. Cl.
CPC .......... *A61K 35/17* (2013.01); *A61K 47/6415* (2017.08); *A61K 47/6849* (2017.08);
(Continued)

(58) Field of Classification Search
CPC ................ A61K 35/17; A61K 47/6415; A61K 47/6849; A61P 35/00; C07K 14/7051; C07K 16/2803
See application file for complete search history.

(56) References Cited

U.S. PATENT DOCUMENTS

| 8,242,252 B2 | 8/2012 | McDonagh et al. |
| 2005/0070693 A1* | 3/2005 | Hansen ................ A61P 21/04 530/388.22 |

(Continued)

FOREIGN PATENT DOCUMENTS

| JP | 2007528209 A | 10/2007 |
| JP | 2013535192 A | 9/2013 |

(Continued)

OTHER PUBLICATIONS

Rabia, L., et al (2018) Understanding and overcoming trade-offs between antibody affinity, specificity, stability, and solubility Biochem Eng. J. 15(137); 365-374 (Year: 2018).*

(Continued)

*Primary Examiner* — Joanne Hama
*Assistant Examiner* — Audrey L Buttice
(74) *Attorney, Agent, or Firm* — Jun He Law Offices P.C.; James J. Zhu

(57) ABSTRACT

The present disclosure provides anti-CD19 antibodies or antigen-binding fragments thereof, isolated polynucleotides encoding the same, pharmaceutical compositions comprising the same, and the uses thereof.

19 Claims, 17 Drawing Sheets
Specification includes a Sequence Listing.

(51) Int. Cl.
    *A61K 47/68*     (2017.01)
    *A61P 35/00*     (2006.01)
    *C07K 14/725*     (2006.01)
    *C07K 16/28*     (2006.01)
    *A61K 9/00*     (2006.01)

(52) U.S. Cl.
    CPC .......... *A61P 35/00* (2018.01); *C07K 14/7051* (2013.01); *C07K 16/2803* (2013.01); *A61K 9/0019* (2013.01)

(56) References Cited

U.S. PATENT DOCUMENTS

| | | | |
|---|---|---|---|
| 2008/0260731 | A1 | 10/2008 | Bernett et al. |
| 2016/0289313 | A1 * | 10/2016 | Chang .................... A61P 17/02 |

FOREIGN PATENT DOCUMENTS

| | | | | |
|---|---|---|---|---|
| JP | 2018535657 | A | | 12/2018 |
| WO | 2008022152 | A2 | | 2/2008 |
| WO | 2008/031056 | A2 | | 3/2008 |
| WO | 2009/052431 | A2 | | 4/2009 |
| WO | 2009/054863 | A2 | | 4/2009 |
| WO | 2010/095031 | A2 | | 8/2010 |
| WO | 2012010561 | A1 | | 1/2012 |
| WO | 2012010562 | A1 | | 1/2012 |
| WO | 2012/156455 | A1 | | 11/2012 |
| WO | WO-2014065402 | A1 * | 5/2014 | ......... C07K 16/2878 |
| WO | 2018002358 | A1 | | 1/2018 |
| WO | 2019/237081 | A1 | | 12/2019 |

OTHER PUBLICATIONS

Tillman, D.M. et al., "immunoglobulin variable region, partial [Mus musculus domesticus]", GenBank: CAA80057.1, Jul. 25, 2016 (Jul. 25, 2016), the whole document.

E. Erica Hong et al: "Design of Coltuximab Ravtansine, a CD19-Targeting Antibody-Drug Conjugate (ADC) for the Treatment of B-Cell Malignancies: Structure-Activity Relationships and Preclinical Evaluation", Molecular Pharmaceutics, vol. 12, No. 6, Jun. 1, 2015 (Jun. 1, 2015), pp. 1703-1716, XP055224780, US; ISSN: 1543-8384, DOI: 10.1021/acs.molpharmaceut.5b00175; * the whole document * * p. 1710, left-hand column; figure 6b*.

Gerber Hans-Peter et al: "Potent antitumor activity of the anti-CD19 auristatin antibody drug conjugate hBU12-vcMMAE against rituximab-sensitive and -resistant lymphomas", Blood, American Society of Hematology, US, vol. 113, No. 18, Apr. 1, 2009 (Apr. 1, 2009), pp. 4352-4361, XP009151913, ISSN: 0006-4971, DOI: 10.1182/BLOOD-2008-09-179143; [retrieved on Jan. 15, 2009] * p. 4355 * * the whole document * * p. 4354, right-hand column, paragraph 2 *.

Extended European Search Report (EESR) of EP18858685.3, dated Apr. 19, 2021.

Morozova O.L. et al., "Prospectives of T-Cells Genetic Programming in Adoptive", Immunotherapy of Malignancies, 2016, 3(25), p. 23-28.

Kulemzin S.V. et al., "CAR T-Cell Therapy: A Balance of Efficacy and Safety", Mol Biol (Mosk). Mar.-Apr. 2017;51 (2):274-287.

The official action and search report for the corresponding RU Appl No. 2020114161, dated May 13, 2022.

Office Action dated Aug. 23, 2022 for the corresponding Japanese Patent Appln No. 2020-516576.

* cited by examiner

ANTI-CD19 ANTIBODIES

FIELD OF THE INVENTION

The present disclosure generally relates to novel anti-CD19 antibodies and the use thereof.

BACKGROUND

CD19 (Cluster of Differentiation 19) is a structurally distinct cell surface receptor expressed on the surface of B cells, including, but not limited to, all subtypes of B-cell lymphoma, from indolent to aggressive forms, as well as B-cell chronic lymphocytic leukemia and non-T acute lymphoblastic leukemia, pre-B cells, B cells in early development (i.e., immature B cells), mature B cells through terminal differentiation into plasma cells, and malignant B cells. CD19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al., J. Immunol., 131:244-250 (1983), Loken et al., Blood, 70:1316-1324 (1987), Uckun et al., Blood, 71:13-29 (1988), Anderson et al., 1984. Blood, 63:1424-1433 (1984), Scheuermann, Leuk. Lymphoma, 18:385-397 (1995)). The expression of CD19 on plasma cells further suggests it may be expressed on differentiated B cell tumors such as multiple myeloma, plasmacytomas, Waldenstrom's tumors (Grossbard et al., Br. J. Haematol., 102:509-15 (1998); Treon et al., Semin. Oncol., 30:248-52 (2003)). CD19 has also been one of the many proposed targets for immunotherapy. Unlike CD20 (another B cell surface receptor), CD19 was thought to be expressed at higher levels and internalized by cells when bound by an anti-CD19 antibody.

Need remains for novel anti-CD19 antibodies, especially those with favorable internalization ability and high binding affinity.

BRIEF SUMMARY OF THE INVENTION

Throughout the present disclosure, the articles "a," "an," and "the" are used herein to refer to one or to more than one (i.e., to at least one) of the grammatical object of the article. By way of example, "an antibody" means one antibody or more than one antibody.

The present disclosure provides novel monoclonal anti-CD19 antibodies, amino acid and nucleotide sequences thereof, and uses thereof.

In one aspect, the present disclosure provides isolated monoclonal antibodies or antigen binding fragments thereof, comprising one or more (e.g., 1, 2, or 3) heavy chain complementarity determining region (CDR) sequences selected from the group consisting of: SEQ ID NOs: 1, 2, 3, 7, 8, 9, 13, 14, 15, 19, 20, 21, 22, 23, 24, 25, 26, 27, 28, 29, 30, 31, 32, 33, 34, 35, 36, 37, 38, 39, 43, 44, 45, 136, 140, and 141, and/or one or more (e.g., 1, 2, or 3) kappa light chain CDR sequences selected from the group consisting of: SEQ ID NOs: 4, 5, 6, 10, 11, 12, 16, 17, 18, 40, 41, 42, 137, 138, and 139.

In certain embodiments, the antibodies or antigen-binding fragments thereof comprise 1, 2, or 3 heavy chain CDR sequences having at least 80% (e.g., at least 85%, 88%, 90%, 91%, 92%, 93%, 94%, 95%, 96%, 97%, 98%, 99%) sequence identity to the sequence of SEQ ID NOs: 1, 2, 3, 7, 8, 9, 13, 14, 15, 19, 20, 21, 22, 23, 24, 25, 26, 27, 28, 29, 30, 31, 32, 33, 34, 35, 36, 37, 38, 39, 43, 44, 45, 136, 140, or 141. In certain embodiments, the antibodies or antigen-binding fragments thereof comprise 1, 2, or 3 light chain CDR sequences having at least 80% (e.g., at least 85%, 88%, 90%, 91%, 92%, 93%, 94%, 95%, 96%, 97%, 98%, 99%) sequence identity to the sequence of SEQ ID NOs: 4, 5, 6, 10, 11, 12, 16, 17, 18, 40, 41, 42, 137, 138, or 139.

In certain embodiments, the antibodies or antigen-binding fragments thereof comprise a heavy chain variable region selected from the group consisting of:
a) a heavy chain variable region comprising 1, 2, or 3 CDR sequences selected from SEQ ID NO: 1, SEQ ID NO: 2, and SEQ ID NO: 3;
b) a heavy chain variable region comprising 1, 2, or 3 CDR sequences selected from SEQ ID NO: 7, SEQ ID NO: 8, and SEQ ID NO: 9;
c) a heavy chain variable region comprising 1, 2, or 3 CDR sequences selected from SEQ ID NO: 13, SEQ ID NO: 14, and SEQ ID NO: 15;
d) a heavy chain variable region comprising 1, 2, or 3 CDR sequences selected from SEQ ID NO: 19, SEQ ID NO: 20, and SEQ ID NO: 21;
e) a heavy chain variable region comprising 1, 2, or 3 CDR sequences selected from SEQ ID NO: 22, SEQ ID NO: 23, and SEQ ID NO: 24;
f) a heavy chain variable region comprising 1, 2, or 3 CDR sequences selected from SEQ ID NO: 25, SEQ ID NO: 26, and SEQ ID NO: 27;
g) a heavy chain variable region comprising 1, 2, or 3 CDR sequences selected from SEQ ID NO: 28, SEQ ID NO: 29, and SEQ ID NO: 30;
h) a heavy chain variable region comprising 1, 2, or 3 CDR sequences selected from SEQ ID NO: 31, SEQ ID NO: 32, and SEQ ID NO: 33;
i) a heavy chain variable region comprising 1, 2, or 3 CDR sequences selected from SEQ ID NO: 34, SEQ ID NO: 35, and SEQ ID NO: 36;
j) a heavy chain variable region comprising 1, 2, or 3 CDR sequences selected from SEQ ID NO: 37, SEQ ID NO: 38, and SEQ ID NO: 39;
k) a heavy chain variable region comprising 1, 2, or 3 CDR sequences selected from SEQ ID NO: 43, SEQ ID NO: 44, and SEQ ID NO: 45;
l) a heavy chain variable region comprising 1, 2, or 3 CDR sequences selected from SEQ ID NO: 136, SEQ ID NO: 2, and SEQ ID NO: 3;
m) a heavy chain variable region comprising 1, 2, or 3 CDR sequences selected from SEQ ID NO: 7, SEQ ID NO: 140, and SEQ ID NO: 9; and
n) a heavy chain variable region comprising 1, 2, or 3 CDR sequences selected from SEQ ID NO: 13, SEQ ID NO: 141, and SEQ ID NO: 15.

In certain embodiments, the antibodies or antigen-binding fragments thereof comprise a kappa light chain variable region selected from the group consisting of:
a) a kappa light chain variable region comprising 1, 2, or 3 CDR sequences selected from SEQ ID NO: 4, SEQ ID NO: 5, and SEQ ID NO: 6;
b) a kappa light chain variable region comprising 1, 2, or 3 CDR sequences selected from SEQ ID NO: 10, SEQ ID NO: 11, and SEQ ID NO: 12;
c) a kappa light chain variable region comprising 1, 2, or 3 CDR sequences selected from SEQ ID NO: 16, SEQ ID NO: 17, and/or SEQ ID NO: 18;
d) a kappa light chain variable region comprising 1, 2, or 3 CDR sequences selected from SEQ ID NO: 40, SEQ ID NO: 41, and SEQ ID NO: 42; and e) a kappa light chain variable region comprising 1, 2, or 3 CDR sequences selected from SEQ ID NO: 137, SEQ ID NO: 138, and SEQ ID NO: 139.

In certain embodiments, the antibodies or antigen-binding fragments thereof comprises:
- a) a heavy chain variable region comprising 1, 2, or 3 CDR sequences selected from SEQ ID NO: 1, SEQ ID NO: 2, and SEQ ID NO: 3; and a kappa light chain variable region comprising 1, 2, or 3 CDR sequences selected from SEQ ID NO: 4, SEQ ID NO: 5, and SEQ ID NO: 6;
- b) a heavy chain variable region comprising 1, 2, or 3 CDR sequences selected from SEQ ID NO: 7, SEQ ID NO: 8, and SEQ ID NO: 9; and a kappa light chain variable region comprising 1, 2, or 3 CDR sequences selected from SEQ ID NO: 10, SEQ ID NO: 11, and SEQ ID NO: 12;
- c) a heavy chain variable region comprising 1, 2, or 3 CDR sequences selected from SEQ ID NO: 13, SEQ ID NO: 14, and SEQ ID NO: 15; and a kappa light chain variable region comprising 1, 2, or 3 CDR sequences selected from SEQ ID NO: 16, SEQ ID NO: 17, and SEQ ID NO: 18;
- d) a heavy chain variable region comprising 1, 2, or 3 CDR sequences selected from SEQ ID NO: 19, SEQ ID NO: 20, and SEQ ID NO: 21; and a kappa light chain variable region comprising 1, 2, or 3 CDR sequences selected from SEQ ID NO: 4, SEQ ID NO: 5, and SEQ ID NO: 6;
- e) a heavy chain variable region comprising 1, 2, or 3 CDR sequences selected from SEQ ID NO: 22, SEQ ID NO: 23, and SEQ ID NO: 24; and a kappa light chain variable region comprising 1, 2, or 3 CDR sequences selected from SEQ ID NO: 4, SEQ ID NO: 5, and SEQ ID NO: 6;
- f) a heavy chain variable region comprising 1, 2, or 3 CDR sequences selected from SEQ ID NO: 25, SEQ ID NO: 26, and SEQ ID NO: 27; and a kappa light chain variable region comprising 1, 2, or 3 CDR sequences selected from SEQ ID NO: 4, SEQ ID NO: 5, and SEQ ID NO: 6;
- g) a heavy chain variable region comprising 1, 2, or 3 CDR sequences selected from SEQ ID NO: 28, SEQ ID NO: 29, and SEQ ID NO: 30; and a kappa light chain variable region comprising 1, 2, or 3 CDR sequences selected from SEQ ID NO: 4, SEQ ID NO: 5, and SEQ ID NO: 6;
- h) a heavy chain variable region comprising 1, 2, or 3 CDR sequences selected from SEQ ID NO: 31, SEQ ID NO: 32, and SEQ ID NO: 33; and a kappa light chain variable region comprising 1, 2, or 3 CDR sequences selected from SEQ ID NO: 4, SEQ ID NO: 5, and SEQ ID NO: 6;
- i) a heavy chain variable region comprising 1, 2, or 3 CDR sequences selected from SEQ ID NO: 34, SEQ ID NO: 35, and SEQ ID NO: 36; and a kappa light chain variable region comprising 1, 2, or 3 CDR sequences selected from SEQ ID NO: 4, SEQ ID NO: 5, and SEQ ID NO: 6;
- j) a heavy chain variable region comprising 1, 2, or 3 CDR sequences selected from SEQ ID NO: 37, SEQ ID NO: 38, and SEQ ID NO: 39; and a kappa light chain variable region comprising 1, 2, or 3 CDR sequences selected from SEQ ID NO: 40, SEQ ID NO: 41, and SEQ ID NO: 42;
- k) a heavy chain variable region comprising 1, 2, or 3 CDR sequences selected from SEQ ID NO: 43, SEQ ID NO: 44, and SEQ ID NO: 45; and a kappa light chain variable region comprising 1, 2, or 3 CDR sequences selected from SEQ ID NO: 4, SEQ ID NO: 5, and SEQ ID NO: 6;
- l) a heavy chain variable region comprising 1, 2, or 3 CDR sequences selected from SEQ ID NO: 136, SEQ ID NO: 2, and SEQ ID NO: 3; and a kappa light chain variable region comprising 1, 2, or 3 CDR sequences selected from SEQ ID NO: 137, SEQ ID NO: 138, and SEQ ID NO: 139;
- m) a heavy chain variable region comprising 1, 2, or 3 CDR sequences selected from SEQ ID NO: 7, SEQ ID NO: 140, and SEQ ID NO: 9; and a kappa light chain variable region comprising 1, 2, or 3 CDR sequences selected from SEQ ID NO: 10, SEQ ID NO: 11, and SEQ ID NO: 12; or
- n) a heavy chain variable region comprising 1, 2, or 3 CDR sequences selected from SEQ ID NO: 13, SEQ ID NO: 141, and SEQ ID NO: 15; and a kappa light chain variable region comprising 1, 2, or 3 CDR sequences selected from SEQ ID NO: 16, SEQ ID NO: 17, and SEQ ID NO: 18.

In certain embodiments, the antibodies or antigen-binding fragments thereof comprise: a heavy chain CDR3 sequence selected from SEQ ID NO: 3, SEQ ID NO: 9, SEQ ID NO: 15, SEQ ID NO: 21, SEQ ID NO: 24, SEQ ID NO: 27, SEQ ID NO: 30, SEQ ID NO: 33, SEQ ID NO: 36, SEQ ID NO: 39, and SEQ ID NO: 45.

In certain embodiments, the antibodies or antigen-binding fragments thereof comprise:
- a) a heavy chain CDR1 sequence selected from SEQ ID NO: 1, SEQ ID NO: 7, SEQ ID NO: 13, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 43, and SEQ ID NO: 136;
- b) a heavy chain CDR2 sequence selected from SEQ ID NO: 2, SEQ ID NO: 8, SEQ ID NO: 14, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 44, SEQ ID NO: 140, and SEQ ID NO: 141; and
- c) a heavy chain CDR3 sequence selected from SEQ ID NO: 3, SEQ ID NO: 9, SEQ ID NO: 15, SEQ ID NO: 21, SEQ ID NO: 24, SEQ ID NO: 27, SEQ ID NO: 30, SEQ ID NO: 33, SEQ ID NO: 36, SEQ ID NO: 39, and SEQ ID NO: 45.

In certain embodiments, the antibodies or antigen-binding fragments thereof comprise:
- a) a light chain CDR1 sequence selected from SEQ ID NO: 4, SEQ ID NO: 10, SEQ ID NO: 16, SEQ ID NO: 40, and SEQ ID NO: 137;
- b) a light chain CDR2 sequence selected from SEQ ID NO: 5, SEQ ID NO: 11, SEQ ID NO: 17, SEQ ID NO: 41, and SEQ ID NO: 138; and
- c) a light chain CDR3 sequence selected from SEQ ID NO: 6, SEQ ID NO: 12, SEQ ID NO: 18, SEQ ID NO: 42, and SEQ ID NO: 139.

In certain embodiments, the antibodies or antigen-binding fragments thereof comprise:
- a) a heavy chain CDR1 sequence selected from SEQ ID NO: 1, SEQ ID NO: 7, SEQ ID NO: 13, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 43, and SEQ ID NO: 136;
- b) a heavy chain CDR2 sequence selected from SEQ ID NO: 2, SEQ ID NO: 8, SEQ ID NO: 14, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 44, SEQ ID NO: 140, and SEQ ID NO: 141;
c) a heavy chain CDR3 sequence selected from SEQ ID NO: 3, SEQ ID NO: 9, SEQ ID NO: 15, SEQ ID NO: 21, SEQ ID NO: 24, SEQ ID NO: 27, SEQ ID NO: 30, SEQ ID NO: 33, SEQ ID NO: 36, SEQ ID NO: 39, and SEQ ID NO: 45;
d) a light chain CDR1 sequence selected from SEQ ID NO: 4, SEQ ID NO: 10, SEQ ID NO: 16, SEQ ID NO: 40, and SEQ ID NO: 137;
e) a light chain CDR2 sequence selected from SEQ ID NO: 5, SEQ ID NO: 11, SEQ ID NO: 17, SEQ ID NO: 41, and SEQ ID NO: 138; and
f) a light chain CDR3 sequence selected from SEQ ID NO: 6, SEQ ID NO: 12, SEQ ID NO: 18, SEQ ID NO: 42, and SEQ ID NO: 139.

In certain embodiments, the antibodies or antigen-binding fragments thereof further comprise one or more (e.g., 1, 2, 3, or 4) heavy chain framework region (FR) sequences selected from the group consisting of: SEQ ID NO: 54, 55, 56, 57, 70, 71, 72, 73, 86, 87, 88, and 89, and/or one or more (e.g., 1, 2, 3, or 4) kappa light chain framework region (FR) sequences selected from SEQ ID NO: 58, 59, 60, 61, 74, 75, 76, 77, 90, 91, 92, and 93.

In certain embodiments, the antibodies or antigen-binding fragments thereof further comprise a heavy chain FR1 sequence selected from SEQ ID NO: 54, 70 and 86; a heavy chain FR2 sequence selected from SEQ ID NO: 55, 71 and 87; a heavy chain FR3 sequence selected from SEQ ID NO: 56, 72 and 88; and/or a heavy chain FR4 sequence selected from SEQ ID NO: 57, 73 and 89.

In certain embodiments, the antibodies or antigen-binding fragments thereof further comprise a light chain FR1 sequence selected from SEQ ID NO: 58, 74 and 90; a light chain FR2 sequence selected from SEQ ID NO: 59, 75 and 91; a light chain FR3 sequence selected from SEQ ID NO: 60, 76 and 92; and/or a light chain FR4 sequence selected from SEQ ID NO: 61, 77 and 93.

In certain embodiments, the antibodies or antigen-binding fragments thereof comprises a heavy chain variable region selected from the group consisting of: SEQ ID NO: 94, SEQ ID NO: 98, SEQ ID NO: 102, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 122, SEQ ID NO: 124, SEQ ID NO: 128, SEQ ID NO: 132 and a homologous sequence thereof having at least 80% (e.g., at least 85%, 88%, 90%, 91%, 92%, 93%, 94%, 95%, 96%, 97%, 98% or 99%) sequence identity.

In certain embodiments, the antibodies or antigen-binding fragments thereof comprises a light chain variable region selected from the group consisting of: SEQ ID NO: 96, SEQ ID NO: 100, SEQ ID NO: 104, SEQ ID NO: 120, SEQ ID NO: 126, SEQ ID NO: 130, SEQ ID NO: 134 and a homologous sequence thereof having at least 80% (e.g., at least 85%, 88%, 90%, 91%, 92%, 93%, 94%, 95%, 96%, 97%, 98% or 99%) sequence identity.

In some embodiments, the antibodies or antigen-binding fragments thereof comprises all or a portion of the heavy chain variable region sequence selected from the group consisting of: SEQ ID NO: 94, 98, 102, 106, 108, 110, 112, 114, 116, 118, 122, 124, 128, and 132; and/or, all or a portion of the light chain variable region sequence selected from the group consisting of: SEQ ID NO: 100, 104, 120, 126, 130, and 134. In one embodiment, the antibodies or antigen-binding fragments thereof is a single domain antibody which consists of all or a portion of the heavy chain variable region selected from the group consisting of: SEQ ID NO: 94, 98, 102, 106, 108, 110, 112, 114, 116, 118, 122, 124, 128, and 132.

In certain embodiments, the antibodies or antigen-binding fragments thereof comprises:
a) a heavy chain variable region comprising SEQ ID NO: 94 and a kappa light chain variable region comprising SEQ ID NO: 96;
b) a heavy chain variable region comprising SEQ ID NO: 98 and a kappa light chain variable region comprising SEQ ID NO: 100;
c) a heavy chain variable region comprising SEQ ID NO: 102 and a kappa light chain variable region comprising SEQ ID NO: 104;
d) a heavy chain variable region comprising SEQ ID NO: 106 and a kappa light chain variable region comprising SEQ ID NO: 96;
e) a heavy chain variable region comprising SEQ ID NO: 108 and a kappa light chain variable region comprising SEQ ID NO: 96;
f) a heavy chain variable region comprising SEQ ID NO: 110 and a kappa light chain variable region comprising SEQ ID NO: 96;
g) a heavy chain variable region comprising SEQ ID NO: 112 and a kappa light chain variable region comprising SEQ ID NO: 96;
h) a heavy chain variable region comprising SEQ ID NO: 114 and a kappa light chain variable region comprising SEQ ID NO: 96;
i) a heavy chain variable region comprising SEQ ID NO: 116 and a kappa light chain variable region comprising SEQ ID NO: 96;
j) a heavy chain variable region comprising SEQ ID NO: 118 and a kappa light chain variable region comprising SEQ ID NO: 120;
k) a heavy chain variable region comprising SEQ ID NO: 122 and a kappa light chain variable region comprising SEQ ID NO: 96;
l) a heavy chain variable region comprising SEQ ID NO: 124 and a kappa light chain variable region comprising SEQ ID NO: 126;
m) a heavy chain variable region comprising SEQ ID NO: 128 and a kappa light chain variable region comprising SEQ ID NO: 130; or
n) a heavy chain variable region comprising SEQ ID NO: 132 and a kappa light chain variable region comprising SEQ ID NO: 134.

In certain embodiments, the antibody or antigen-binding fragment thereof further comprises one or more amino acid residue substitutions yet retains specific binding affinity to CD19.

In certain embodiments, the substitution is in one or more CDR sequences, and/or in one or more FR sequences, in one or both variable region sequences, and/or in Fc region. In some embodiments, at least one (or all) of the substitution(s) in the CDR sequences, FR sequences, variable region sequences or Fc region comprises a conservative substitution.

In certain embodiments, the antibody or antigen-binding fragment thereof comprises no more than 10, 9, 8, 7, 6, 5, 4, 3, 2, or 1 amino acid residue substitutions in one or more CDR sequences selected from SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 136, 137, 138, 139, 140, and 141.

In certain embodiments, the antibody or antigen-binding fragment thereof comprises no more than 10, 9, 8, 7, 6, 5, 4, 3, 2, or 1 amino acid residue substitutions in one or more FR sequences selected from SEQ ID NO: 54, 55, 56, 57, 58, 59, 60, 61, 70, 71, 72, 73, 74, 75, 76, 77, 86, 87, 88, 89, 90, 91, 92, and 93. In certain embodiments, the antibody or antigen-binding fragment thereof comprises no more than 10, 9, 8, 7, 6, 5, 4, 3, 2, or 1 substitutions in total in CDR sequences and/or FR sequences of a heavy chain variable region sequences selected from SEQ ID NO: 94, 98, 102, 106, 108, 110, 112, 114, 116, 118, 122, 124, 128, and 132. In certain embodiments, the antibody or antigen-binding fragment thereof comprises no more than 10, 9, 8, 7, 6, 5, 4, 3, 2, or 1 amino acid residue substitutions in all the FRs of a light chain variable region sequences selected from SEQ ID NO: 96, 100, 104, 120, 126, 130, and 134.

In certain embodiments, the substitution confers one or more desirable properties selected from: a) improving binding affinity to CD19, b) introducing or removing a glycosylation site, c) introducing a free cysteine residue, d) enhancing or reducing ADCC or CDC, e) increasing serum half-life; and f) increasing FcRn binding.

In certain embodiments, the antibody or antigen-binding fragment thereof further comprises an immunoglobulin constant region. In certain embodiments, the antibody or antigen-binding fragment thereof comprises a constant region of IgG. In certain embodiment, the antibody or antigen-binding fragment thereof comprises a constant region of mouse IgG1, mouse IgG2a, mouse IgG2b, or human IgG1.

In certain embodiments, the antibodies or antigen-binding fragments thereof is a non-human (e.g., murine or rodent) antibody or a humanized antibody.

In certain embodiments, the antibodies or antigen-binding fragments thereof are a camelized single domain antibody, a diabody, a scFv, an scFv dimer, a BsFv, a dsFv, a (dsFv)2, a dsFv-dsFv', an Fv fragment, a Fab, a Fab', a F(ab')2, a bispecific antibody, a ds diabody, a nanobody, a domain antibody, or a bivalent domain antibody.

In certain embodiments, the antibodies or antigen-binding fragments thereof is bispecific.

In certain embodiments, the antibodies or antigen-binding fragments thereof is linked to one or more conjugates. In certain embodiments, the conjugate comprises a chemotherapeutic agent, a toxin, a radioactive isotope, a lanthanide, a luminescent label, a fluorescent label, or an enzyme-substrate label. In certain embodiments, the conjugate is a toxin. In certain embodiments, the toxin is a cytotoxin, a DNA-alkylators, a topoisomerase inhibitor, a tubulin-Binders, or other anticancer drugs. In certain embodiments, the anticancer drug is a maytansinoid cytotoxic agent. In certain embodiments, the toxin is DM1

In certain embodiments, the antibody or an antigen-binding fragment thereof is capable of specifically binding to CD19. In certain embodiments, the CD19 are derived from mouse, rat, monkey or human.

In certain embodiments, the antibodies or antigen-binding fragments thereof is capable of specifically binding to human CD19 expressed on a cell at a $K_D$ value of no more than $5\times10^{-9}$M, no more than $1\times10^{-9}$M, no more than $9\times10^{-10}$ M, no more than $8\times10^{-10}$ M, no more than $7\times10^{-10}$ M, no more than $6\times10^{-10}$M, no more than $5\times10^{-10}$ M, no more than $4\times10^{-10}$ M, no more than $3\times10^{-10}$M, no more than $2\times10^{-10}$ M, no more than $1\times10^{-10}$ M as measured by flow cytometry assay.

In certain embodiments the antibodies or antigen-binding fragments thereof is capable of specifically binding to human CD19 expressed on a cell with an $EC_{50}$ of no more than 0.04 nM, no more than 0.05 nM, no more than 0.1 nM, no more than 0.2 nM, no more than 0.3 nM, no more than 0.4 nM, no more than 0.5 nM, no more than 0.5 nM, no more than 0.6 nM, no more than 0.7 nM, no more than 0.8 nM, no more than 0.9 nM, or no more than 1 nM by flow cytometry assay.

In certain embodiments, the antibodies or antigen-binding fragments thereof is capable of specifically binding to Cynomolgus monkey CD19 expressed on a cell at an $EC_{50}$ of no more than 0.2 nM, no more than 0.5 nM, no more than 0.8 nM, no more than 1 nM, no more than 2 nM, or no more than 3 nM by flow cytometry assay.

In certain embodiments, the antibodies or antigen-binding fragments thereof is capable of being internalized by a CD19-expressing cell at an $EC_{50}$ of no more than 1 pM, no more than 2 pM, no more than 3 pM, no more than 4 pM, no more than 5 pM, no more than 6 pM, no more than 7 pM, no more than 8 pM, no more than 9 pM, no more than 10 pM, no more than 11 pM, no more than 12 pM, no more than 13 pM, no more than 14 pM, no more than 15 pM, no more than 16 pM, no more than 17 pM, no more than 18 pM, no more than 19 pM, no more than 20 pM, no more than 21 pM, no more than 22 pM, no more than 23 pM, no more than 24 pM, no more than 25 pM, no more than 30 pM, no more than 35 pM, no more than 40 pM, no more than 45 pM, or no more than 50 pM by Fab-Zap assay.

In one aspect, the present disclosure provides antibodies or antigen-binding fragments thereof, which compete for the same epitope with W7011-4.155.8, W7011-4.202.9, or W7011-4.225.7.

In one aspect, the present disclosure further provides pharmaceutical compositions comprising the antibody or antigen-binding fragment thereof provided herein and a pharmaceutically acceptable carrier. In certain embodiments, the pharmaceutical composition further comprises a second agent which is capable of enhancing a therapeutic effect of the antibody or antigen-binding fragment thereof and/or is capable of reducing a side effect of the antibody or antigen-binding fragment thereof.

In one aspect, the present disclosure further provides isolated polynucleotides encoding the antibody or an antigen-binding fragment thereof provided herein. In certain embodiments, the isolated polynucleotide comprises a nucleotide sequence selecting from a group consisting of SEQ ID NO: 95, 99, 103, 107, 109, 111, 113, 115, 117, 119, 123, 125, 129 and 133, and/or a nucleotide sequence selecting from a group consisting of SEQ ID NO: 97, 101, 105, 121, 127, 131 and 135, or a homologue sequence thereof having at least 80% (e.g., at least 85%, 88%, 90%, 91%, 92%, 93%, 94%, 95%, 96%, 97%, 98% or 99%) sequence identity but encoding the same protein sequence.

In one aspect, the present disclosure further provides vectors comprising said isolated polynucleotide.

In one aspect, the present disclosure further provides host cells comprising said vector.

In one aspect, the present disclosure further provides methods of expressing the antibody or antigen-binding fragment thereof provided herein, comprising culturing said host cell under the condition at which said polynucleotide is expressed.

In one aspect, the present disclosure further provides antibody-drug conjugates comprising one or more drug moieties covalently attached to the antibodies or antigen-binding fragments provided herein, either directly or via a linker. In certain embodiments, the linker is a hydrazone linker, a disulfide linker, a bifunctional linker, dipeptide linker, glucuronide linker, a thioether linker. In certain embodiments, the linker is SMCC.

In certain embodiments, at least one drug moiety is attached to a specific site of the antibodies or antigen-binding fragments thereof. In certain embodiments, the specific site is a cysteine residue. In certain embodiments, the drug moieties are toxin or radioactive isotopes. In certain embodiments, the drug moieties are is a toxin, optionally a cytotoxin, a DNA-alkylators, a topoisomerase inhibitor, a tubulin-binders, or other anticancer drugs, optionally a maytansinoid cytotoxic agent, optionally the toxin is DM1.

In one aspect, the present disclosure further provides pharmaceutical compositions comprising the antibodies or antigen-binding fragments thereof provided herein, or the antibody-drug conjugates provided herein, and a pharmaceutically acceptable carrier.

In one aspect, the present disclosure further provides methods of treating a CD19 related disease or condition in a subject, comprising administering a therapeutically effective amount of the antibodies or antigen-binding fragments thereof provided herein, the antibody-drug conjugates provided herein, or the pharmaceutical composition provided herein, to the subject. In certain embodiments, the subject is human. In certain embodiments, the administration is via oral, nasal, intravenous, subcutaneous, sublingual, or intramuscular administration. In certain embodiments, said disease or condition is cancer. In certain embodiments, said cancer is lymphoma, lung cancer, liver cancer, cervical cancer, colon cancer, breast cancer, ovarian cancer, pancreatic cancer, melanoma, glioblastoma, prostate cancer, esophageal cancer or gastric cancer. In certain embodiments, said disease or condition is B cell lymphoma, optionally Hodgkin lymphoma or non-Hodgkin lymphoma, wherein the non-Hodgkin lymphoma comprises: Diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), Mantle cell lymphoma (MCL), Acute Lymphoblastic Leukemia (ALL), or Waldenstrom's Macroglobulinemia (WM).

In one aspect, the present disclosure further provides methods of modulating CD19 activity in a CD19-expressing cell, comprising exposing the CD19-expressing cell to the antibodies or antigen-binding fragments thereof provided herein.

In one aspect, the present disclosure further provides in vivo or in vitro methods of killing a CD19-expressing cell, comprising contacting the CD19-expressing cell with the antibody-drug conjugates provided herein.

In one aspect, the present disclosure further provides a method of detecting presence or amount of CD19 in a sample, comprising contacting the sample with the antibodies or antigen-binding fragments thereof provided herein, and determining the presence or the amount of CD19 in the sample.

In one aspect, the present disclosure further provides methods of diagnosing a CD19 related disease or condition in a subject, comprising: a) obtaining a sample from the subject; b) contacting the sample with the antibodies or antigen-binding fragments thereof provided herein; c) determining presence or amount of CD19 in the sample; d) correlating the presence or amount of CD19 to a disease or a condition in the subject.

In one aspect, the present disclosure further provides use of the antibodies or antigen-binding fragments thereof provided herein in the manufacture of a medicament for treating a disease or condition in a subject, wherein the treating comprises: administering a therapeutically effective amount of the antibodies or antigen-binding fragments thereof to the subject.

In one aspect, the present disclosure further provides use of the antibodies or antigen-binding fragments thereof provided herein in the manufacture of a diagnostic reagent for detecting CD19 related disease or condition.

In one aspect, the present disclosure provides chimeric antigen receptors (CARs) comprising the antigen binding fragment provided herein and a T-cell activation moiety. In some embodiment, the T-cell activation moiety comprises a native T-cell activation moiety of a T cell receptor (TCR). In some embodiment, the T-cell activation moiety comprises a transmembrane domain of a TCR and an intracellular signaling transduction domain of a TCR. In some embodiment, the antigen binding fragment is a scFv.

In one aspect, the present disclosure provides nucleic acids encoding the CAR provided herein. In certain embodiments, the nucleic acids comprise a first polynucleotide sequence encoding an antigen binding fragment of the antibodies provided herein, operably linked to a second polynucleotide sequence encoding a transmembrane domain of the TCR and an intracellular signaling transduction domain of a TCR.

In one aspect, the present disclosure provides vectors comprising the nucleic acid sequence encoding the CAR provided herein.

In one aspect, the present disclosure provides isolated T cells which express the CAR provided herein.

In one aspect, the present disclosure provides methods for stimulating a T cell-mediated immune response to a CD19-expressing target in a subject, the method comprising administering to the subject an effective amount of the T cells provided herein.

DETAILED DESCRIPTION OF THE INVENTION

Figure 1:
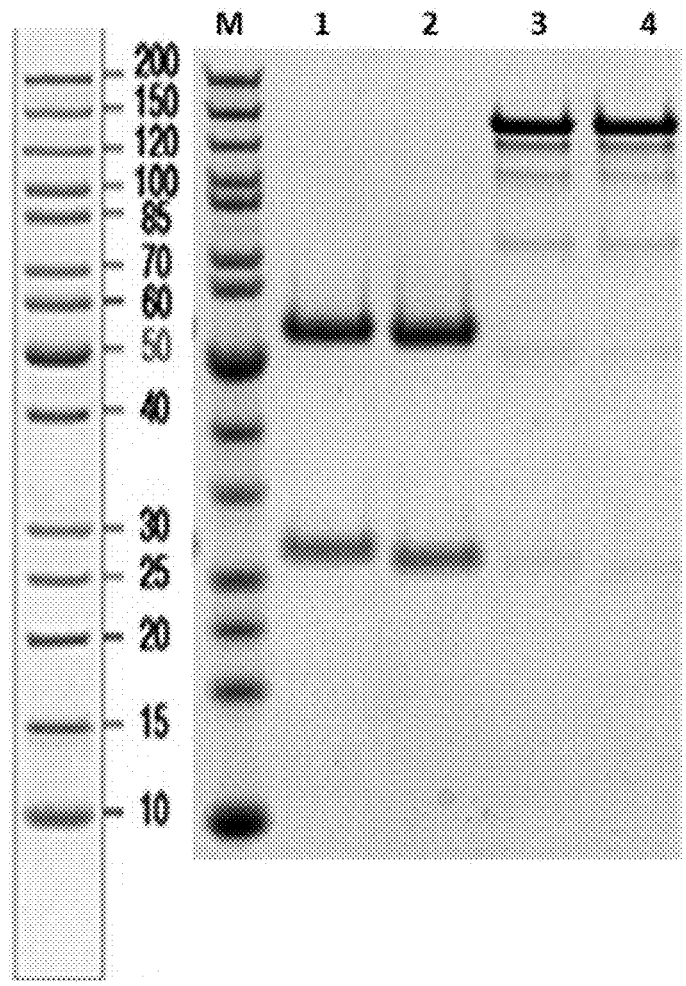
FIG. 1 shows SDS-PAGE of WBP701-BMK1 and WBP701-BMK2. M: Protein marker; Lane1: BMK1, reduced; Lane2: BMK2, reduced; Lane3: BMK1, non-reduced; Lane4: BMK4, non-reduced.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multivalent antibody, bivalent antibody, monovalent antibody, multispecific antibody, or bispecific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region ($V_H$) and a first, second, and third constant region ($C_{H1}$, $C_{H2}$, $C_{H3}$, respectively); mammalian light chains are classified as λ or κ, while each light chain consists of a variable region ($V_L$ for λ light chain or $V_K$ for κ light chain, respectively) and a constant region ($C_L$ for λ light chain or $C_K$ for κ light chain, respectively). The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). CDR boundaries for the antibodies and antigen-binding fragments disclosed herein may be defined or identified by the conventions of Kabat, IMGT, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342 (6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen-binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, delta, epsilon, gamma, and μ heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (α1 heavy chain), or IgA2 (α2 heavy chain).

The term "bivalent" as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites. In some embodiments, the antibody or antigen-binding fragment thereof is bivalent.

As used herein, a "bispecific" antibody refers to an artificial antibody which has fragments derived from two different monoclonal antibodies and is capable of binding to two different epitopes. The two epitopes may present on the same antigen, or they may present on two different antigens.

The term "antigen-binding fragment" as used herein refers to an antibody fragment formed from a portion of an antibody comprising 1, 2, or 3 CDRs, or any other antibody fragment that binds to an antigen but does not comprise an intact native antibody structure. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific antibody, a multispecific antibody, a camelized single domain antibody, a nanobody, a domain antibody, and a bivalent domain antibody. An antigen-binding fragment is capable of binding to the same antigen to which the parent antibody binds.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'. "Fv" with regard to an antibody refers to the smallest fragment of the antibody to bear the complete antigen-binding site. An Fv fragment consists of the variable region of a single light chain bound to the variable region of a single heavy chain.

A "dsFv" refers to a disulfide-stabilized Fv fragment that the linkage between the variable region of a single light chain and the variable region of a single heavy chain is a disulfide bond. In some embodiments, a "(dsFv)$_2$" or "(dsFv-dsFv')" comprises three peptide chains: two $V_H$ moieties linked by a peptide linker (e.g., a long flexible linker) and bound to two $V_L$ moieties, respectively, via disulfide bridges. In some embodiments, dsFv-dsFv' is bispecific in which each disulfide paired heavy and light chain has a different antigen specificity.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879(1988)).

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as antibody-dependent cell-mediated cytotoxicity (ADCC), and complement dependent cytotoxicity (CDC), but does not function in antigen binding.

"Single-chain Fv-Fc antibody" or "scFv-Fc" refers to an engineered antibody consisting of a scFv connected to the Fc region of an antibody.

"Camelized single domain antibody", "heavy chain antibody", or "HCAb" refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363(6428):446-8 (1993); Nguyen V K. et al. "Heavy-chain antibodies in Camelidae; a case of evolutionary innovation," Immunogenetics. April; 54(1):39-47 (2002); Nguyen V K. et al. Immunology. May; 109(1): 93-101 (2003)). The variable domain of a heavy chain antibody (VHH domain) represents the smallest known antigen-binding unit generated by adaptive immune responses (Koch-Nolte F. et al., FASEB J. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" or "dAbs" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same or different antigens (or epitopes). In certain embodiments, a "bispecific ds diabody" is a diabody target two different antigens (or epitopes). In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human animal, such as from mouse or rat. In some embodiments, the non-human animal is a mammal, for example, a mouse, a rat, a rabbit, a goat, a sheep, a guinea pig, or a hamster.

The term "humanized" as used herein means that the antibody or antigen-binding fragment comprises CDRs derived from non-human animals, FR regions derived from human, and when applicable, constant regions derived from human.

As used herein, the term "CD19" refers to the Cluster of Differentiation 19 protein, which is an antigenic determinant detectable on leukemia precursor cells. The human and mouse CD19 amino acid and nucleic acid sequences can be found in a public database, such as GenBank, UniProt and Swiss-Prot. For example, the amino acid sequence of human CD19 can be found as UniProt/Swiss-Prot Accession No. P15391 and the nucleotide sequence encoding of the human CD19 can be found at Accession No. NM_001178098. As used herein, the term CD19 includes proteins comprising mutations, e.g., point mutations, fragments, insertions, deletions and splice variants of full length wild-type CD19. CD19 is expressed on most B lineage cancers, including, e.g., acute lymphoblastic leukemia, chronic lymphocyte leukemia and non-Hodgkin lymphoma. It is also an early marker of B cell progenitors. See, e.g., Nicholson et al. Mol. Immun. 34 (16-17): 1157-1165 (1997). In one aspect, the CD19 protein is expressed on a cancer cell.

The term "specific binding" or "specifically binds" as used herein refers to a non-random binding reaction between two molecules, such as for example between an antibody and an antigen. In certain embodiments, the antibodies or antigen-binding fragments provided herein specifically bind to human and/or CD19 with a binding affinity ($K_D$) of $\leq 10^{-6}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 4 \times 10^{-9}$ M, $\leq 3 \times 10^{-9}$ M, $\leq 2 \times 10^{-9}$ M, or $\leq 10^{-9}$ M. $K_D$ used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the $K_D$ value can be appropriately determined by using flow cytometry method.

The ability to "block binding" or "compete for the same epitope" as used herein refers to the ability of an antibody or antigen-binding fragment to inhibit the binding interaction between two molecules (e.g., human CD19 and an anti-CD19 antibody) to any detectable degree. In certain embodiments, an antibody or antigen-binding fragment that blocks binding between two molecules inhibits the binding interaction between the two molecules by at least 50%, at least 60%, at least 70%, at least 75%, at least 80%, at least 85%, or at least 90%. In certain embodiments, this inhibition may be greater than 60%, greater than 70%, greater than 75%, greater than 80%, greater than 85%, or greater than 90%.

The term "epitope" as used herein refers to the specific group of atoms or amino acids on an antigen to which an antibody binds. Two antibodies may bind the same or a closely related epitope within an antigen if they exhibit competitive binding for the antigen. For example, if an antibody or antigen-binding fragment blocks binding of a reference antibody to the antigen (e.g., human/monkey CD19) by at least 50%, at least 60%, at least 70%, at least 75%, at least 80%, at least 85%, or at least 90%, then the antibody or antigen-binding fragment may be considered to bind the same/closely related epitope as the reference antibody.

Those skilled in the art will recognize that it is possible to determine, without undue experimentation, if a human monoclonal antibody binds to the same epitope as the antibody of present disclosure (e.g., mouse monoclonal antibodies WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.231.5, and humanized antibodies W7011-4.34.11-z1-m5, W7011-4.87.6-z1(N-S), and W7011-4.155.8-z1-P15) by ascertaining whether the former prevents the latter from binding to a CD19 antigen polypeptide. If the test antibody competes with the antibody of present disclosure, as shown by a decrease in binding by the antibody of present disclosure to the CD19 antigen polypeptide, then the two antibodies bind to the same, or a closely related, epitope. Or if the binding of a test antibody to the CD19 antigen polypeptide was inhibited by the antibody of present disclosure, then the two antibodies bind to the same, or a closely related, epitope.

The various symbols used in the antibody names as provided herein are of different representation: "mIgG2" refers to an antibody with mouse constant region of IgG2 isotype; "uIgG1" refers an antibody with human constant region of IgG1 isotype; "K" or "L" refers to an antibody using the kappa or lambda light chain.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g., Met, Ala, Val, Leu, and Ile), among residues with neutral hydrophilic side chains (e.g., Cys, Ser, Thr, Asn and Gln), among residues with acidic side chains (e.g., Asp, Glu), among amino acids with basic side chains (e.g., His, Lys, and Arg), or among residues with aromatic side chains (e.g., Trp, Tyr, and Phe). As known in the art, conservative substitution usually does not cause significant change in the protein conformational structure, and therefore could retain the biological activity of a protein.

The term "homologue" and "homologous" as used herein are interchangeable and refer to nucleic acid sequences (or its complementary strand) or amino acid sequences that have sequence identity of at least 80% (e.g., at least 85%, 88%, 90%, 91%, 92%, 93%, 94%, 95%, 96%, 97%, 98%, 99%) to another sequences when optimally aligned.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

As used herein, an antibody that "internalizes" or "is capable of being internalized" is the antibody that is taken up by a cell upon binding to its antigen on the surface of the cell. In some embodiments, the antibody and the fragments thereof provided herein may be internalized, at least to some extent, by cells that express CD19 on their surfaces. For example, in some embodiments, an anti-CD19 antibody provided herein can be internalized by a B cell lymphoma cell upon binding to the CD19 expressed on the surface of the cell. Internalization may occur in vitro or in vivo. For therapeutic applications, internalization may occur in vivo. Whether an antibody internalizes upon binding to a mammalian cell can be determined by various assays including those described in the Examples below (e.g., the Fab-Zap method). Methods of detecting whether an antibody internalizes into a cell are also described in U.S. Pat. No. 7,619,068 which is incorporated herein by reference in its entirety. In some embodiments, the antibodies and the antigen binding fragments thereof capable of being internalized may be associated with or conjugated to anti-cancer agents such as cytotoxic moieties that kill the cell upon internalization. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. An isolated "nucleic acid" or "polynucleotide" are used interchangeably and refer to the sequence of an isolated nucleic acid molecule. In certain embodiments, an "isolated antibody or antigen-binding fragment thereof" refers to the antibody or antigen-binding fragments having a purity of at least 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the antibody or antigen-binding fragment thereof, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCal, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

A "CD19 related disease or condition" as used herein refers to any disease or condition caused by, exacerbated by, or otherwise linked to increased or decreased expression or activities of CD19. In some embodiments, the CD19 related condition is B cell lymphoma, optionally Hodgkin lymphoma or non-Hodgkin lymphoma, wherein the non-Hodgkin lymphoma comprises: Diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), Mantle cell lymphoma (MCL), Acute Lymphoblastic Leukemia (ALL), or Waldenstrom's Macroglobulinemia (WM).

"Cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer include but are not limited to, non-small cell lung cancer (squamous/nonsquamous), small cell lung cancer, renal cell cancer, colorectal cancer, colon cancer, ovarian cancer, breast cancer (including basal breast carcinoma, ductal carcinoma and lobular breast carcinoma), pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, melanoma, myelomas, mycoses fungoids, merkel cell cancer, hepatocellular carcinoma (HCC), fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, lymphoid malignancy, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, hepatoma, bile duct carcinoma, choriocarcinoma, Wilms' tumor, cervical cancer, testicular tumor, seminoma, classical Hodgkin lymphoma (CHL), primary mediastinal large B-cell lymphoma, T-cell/histiocyte-rich B-cell lymphoma, acute lymphocytic leukemia, acute myelocytic leukemia, acute myelogenous leukemia, chronic myelocytic (granulocytic) leukemia, chronic myelogenous leukemia, chronic lymphocytic leukemia, polycythemia vera, mast cell derived tumors, EBV-positive and -negative PTLD, diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), Mantle cell lymphoma (MCL), Acute Lymphoblastic Leukemia (ALL), plasmablastic lymphoma, extranodal NK/T-cell lymphoma, nasopharyngeal carcinoma, HHV8-associated primary effusion lymphoma, non-Hodgkin's lymphoma, multiple myeloma, Waldenstrom's macroglobulinemia (WM), heavy chain disease, myelodysplastic syndrome, hairy cell leukemia and myelodysplasia, primary CNS lymphoma, spinal axis tumor, brain stem glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-CD19 Antibody

The present disclosure provides anti-CD19 antibodies and antigen-binding fragments thereof comprising one or more (e.g., 1, 2, 3, 4, 5, or 6) CDR sequences of an anti-CD19 antibody selected from WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.231.5, W7011-4.34.11-z1-m5, W7011-4.87.6-z1(N-S), and W7011-4.155.8-z1-P15. Throughout the present disclosure, the term "WBP7011" with respect to the antibody names is used interchangeably with "W7011". For example, antibody WBP7011-4.34.11 is also referred to as W7011-4.34.11 and such names refer to the same antibody.

"WBP7011-4.34.11" as used herein refers to a mouse monoclonal antibody having a heavy chain variable region of SEQ ID NO: 94, and a kappa light chain variable region of SEQ ID NO: 96.

"WBP7011-4.87.6" as used herein refers to a mouse monoclonal antibody having a heavy chain variable region of SEQ ID NO: 98, and a kappa light chain variable region of SEQ ID NO: 100.

"WBP7011_4.155.8" as used herein refers to a mouse monoclonal antibody having a heavy chain variable region of SEQ ID NO: 102, and a kappa light chain variable region of SEQ ID NO: 104.

"WBP7011_4.56.1" as used herein refers to a mouse monoclonal antibody having a heavy chain variable region of SEQ ID NO: 106, and a kappa light chain variable region of SEQ ID NO: 96.

"WBP7011-4.15.10" as used herein refers to a mouse monoclonal antibody having a heavy chain variable region of SEQ ID NO: 108, and a kappa light chain variable region of SEQ ID NO: 96.

"WBP7011-4.100.1" as used herein refers to a mouse monoclonal antibody having a heavy chain variable region of SEQ ID NO: 110, and a kappa light chain variable region of SEQ ID NO: 96.

"WBP7011-4.106.3" as used herein refers to a mouse monoclonal antibody having a heavy chain variable region of SEQ ID NO: 112, and a kappa light chain variable region of SEQ ID NO: 96.

"WBP7011_4.108.3" as used herein refers to a mouse monoclonal antibody having a heavy chain variable region of SEQ ID NO: 114, and a kappa light chain variable region of SEQ ID NO: 96.

"WBP7011_4.191.6" as used herein refers to a mouse monoclonal antibody having a heavy chain variable region of SEQ ID NO: 116, and a kappa light chain variable region of SEQ ID NO: 96.

"WBP7011_4.194.10" as used herein refers to a mouse monoclonal antibody having a heavy chain variable region of SEQ ID NO: 118, and a kappa light chain variable region of SEQ ID NO: 120.

"WBP7011_4.231.5" as used herein refers to a mouse monoclonal antibody having a heavy chain variable region of SEQ ID NO: 122, and a kappa light chain variable region of SEQ ID NO: 96.

"W7011-4.34.11-z1-m5" as used herein refers to a humanized antibody based on WBP3311_2.166.48 that comprises a heavy chain variable region of SEQ ID NO: 124, and a kappa light chain variable region of SEQ ID NO: 126.

"W7011-4.87.6-z1(N-S)" as used herein refers to a humanized antibody based on WBP3311_2.166.48 that comprises a heavy chain variable region of SEQ ID NO 128, and a kappa light chain variable region of SEQ ID NO: 130.

"W7011-4.155.8-z1-P15" as used herein refers to a humanized antibody based on WBP3311_2.166.48 that comprises a heavy chain variable region of SEQ ID NO: 132, and a kappa light chain variable region of SEQ ID NO: 134.

Table 1 shows the CDR sequences of these 11 mouse anti-CD19 antibodies, and of the three humanized antibodies W7011-4.34.11-z1-m5, W7011-4.87.6-z1(N-S), and W7011-4.155.8-z1-P15. The heavy chain and light chain variable region sequences are also provided below.

TABLE 1

|  |  | CDR1 | CDR2 | CDR3 |
| --- | --- | --- | --- | --- |
| WBP7011-4.34.11 | VH | SEQ ID NO: 1<br>GYTFTNYVIH | SEQ ID NO: 2<br>YFNPYNDGTEYNEKFKA | SEQ ID NO: 3<br>GPYYYGSSPFDY |
| WBP7011-4.34.11 | VK | SEQ ID NO: 4<br>RSSQSLENSNGNTYLN | SEQ ID NO: 5<br>RVSNRFS | SEQ ID NO: 6<br>LQVTHVPYT |
| WBP7011-4.87.6 | VH | SEQ ID NO: 7<br>GYAFSTYWMN | SEQ ID NO: 8<br>QIYPGDDDTKYNGKFKG | SEQ ID NO: 9<br>RYFRYDYWYSDV |
| WBP7011-4.87.6 | VK | SEQ ID NO: 10<br>RASQDISNYLN | SEQ ID NO: 11<br>YTSRLHS | SEQ ID NO: 12<br>HQGNTLPLT |
| WBP7011_4.155.8 | VH | SEQ ID NO: 13<br>GYAFTSYNMY | SEQ ID NO: 14<br>YIDPYNGDTTYNQKFKG | SEQ ID NO: 15<br>TAYAMDY |
| WBP7011_4.155.8 | VK | SEQ ID NO: 16<br>SASSTVNYMH | SEQ ID NO: 17<br>STSNLAS | SEQ ID NO: 18<br>HQWSSYPYT |
| WBP7011_4.56.1 | VH | SEQ ID NO: 19<br>GYTFTNYVIH | SEQ ID NO: 20<br>YINPYNDGTEYNEKFKG | SEQ ID NO: 21<br>GPYYYGGSPFDY |

TABLE 1-continued

|  |  | CDR1 | CDR2 | CDR3 |
|---|---|---|---|---|
| WBP7011_4.56.1 | VK | SEQ ID NO: 4 RSSQSLENSNGNTYLN | SEQ ID NO: 5 RVSNRFS | SEQ ID NO: 6 LQVTHVPYT |
| WBP7011-4.15.10 | VH | SEQ ID NO: 22 GYTFTSYVMH | SEQ ID NO: 23 YINPYNDGTEYHEKFKG | SEQ ID NO: 24 GPYYYGGSPFDF |
| WBP7011-4.15.10 | VK | SEQ ID NO: 4 RSSQSLENSNGNTYLN | SEQ ID NO: 5 RVSNRFS | SEQ ID NO: 6 LQVTHVPYT |
| WBP7011-4.100.1 | VH | SEQ ID NO: 25 GYTFTSYVIH | SEQ ID NO: 26 YINPYNDGAEYTEKFKG | SEQ ID NO: 27 GPYYYGGSPFDY |
| WBP7011-4.100.1 | VK | SEQ ID NO: 4 RSSQSLENSNGNTYLN | SEQ ID NO: 5 RVSNRFS | SEQ ID NO: 6 LQVTHVPYT |
| WBP7011-4.106.3 | VH | SEQ ID NO: 28 GYTFSSYVIH | SEQ ID NO: 29 YINPYNDGAEYAEKFKG | SEQ ID NO: 30 GPYYYGGSPFDY |
| WBP7011-4.106.3 | VK | SEQ ID NO: 4 RSSQSLENSNGNTYLN | SEQ ID NO: 5 RVSNRFS | SEQ ID NO: 6 LQVTHVPYT |
| WBP7011_4.108.3 | VH | SEQ ID NO: 31 GYTFTSYVIH | SEQ ID NO: 32 YINPYNDGAEYNEKFKG | SEQ ID NO: 33 GPYYYGSSPFDY |
| WBP7011_4.108.3 | VK | SEQ ID NO: 4 RSSQSLENSNGNTYLN | SEQ ID NO: 5 RVSNRFS | SEQ ID NO: 6 LQVTHVPYT |
| WBP7011_4.191.6 | VH | SEQ ID NO: 34 GYTFTDYVIH | SEQ ID NO: 35 YINPYNDGSEYSEKFKG | SEQ ID NO: 36 GPYYYGGSPFDY |
| WBP7011_4.191.6 | VK | SEQ ID NO: 4 RSSQSLENSNGNTYLN | SEQ ID NO: 5 RVSNRFS | SEQ ID NO: 6 LQVTHVPYT |
| WBP7011_4.194.10 | VH | SEQ ID NO: 37 GYTFTSYVMH | SEQ ID NO: 38 YINPYNDGTKYNEKFKG | SEQ ID NO: 39 GPYYYGSSPFDY |
| WBP7011_4.194.10 | VK | SEQ ID NO: 40 RSSQTLENSNGNTYLN | SEQ ID NO: 41 RVSNRFS | SEQ ID NO: 42 LQVTHVPYT |
| WBP7011_4.231.5 | VH | SEQ ID NO: 43 GYTFTSYVMH | SEQ ID NO: 44 YINPYNDGTQYNEKFKG | SEQ ID NO: 45 GPYYYSPSPFDY |
| WBP7011_4.231.5 | VK | SEQ ID NO: 4 RSSQSLENSNGNTYLN | SEQ ID NO: 5 RVSNRFS | SEQ ID NO: 6 LQVTHVPYT |
| W7011-4.34.11-z1-m5 | VH | SEQ ID NO: 136 GYTFTDYVIH | SEQ ID NO: 2 YFNPYNDGTEYNEKFKA | SEQ ID NO: 3 GPYYYGSSPFDY |
| W7011-4.34.11-z1-m5 | VK | SEQ ID NO: 137 RSSQSLENSNHNTYIN | SEQ ID NO: 138 RVSKRFS | SEQ ID NO: 139 HQVTHVPYT |
| W7011-4.87.6-z1(N-S) | VH | SEQ ID NO: 7 GYAFSTYWMN | SEQ ID NO: 140 QIYPGDDDTKYSGKFKG | SEQ ID NO: 9 RYFRYDYWYSDV |
| W7011-4.87.6-z1(N-S) | VK | SEQ ID NO: 10 RASQDISNYLN | SEQ ID NO: 11 YTSRLHS | SEQ ID NO: 12 HQGNTLPLT |
| W7011-4.155.8-z1-P15 | VH | SEQ ID NO: 13 GYAFTSYNMY | SEQ ID NO: 141 YIDPYNADTTYNQKFKG | SEQ ID NO: 15 TAYAMDY |

TABLE 1-continued

| | CDR1 | CDR2 | CDR3 |
|---|---|---|---|
| W7011-4.155.8-VK z1-P15 | SEQ ID NO: 16 SASSTVNYMH | SEQ ID NO: 17 STSNLAS | SEQ ID NO: 18 HQWSSYPYT |

Heavy or kappa light chain variable region sequences of WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, or WBP7011_4.231.5, and humanized W7011-4.34.11-z1-m5, W7011-4.87.6-z1(N-S), and W7011-4.155.8-z1-P15 antibodies are provided below.

WBP7011-4.34.11-VH
Amino acid sequence (SEQ ID NO: 94):
EVQLQQSGPELVKPGASVKMSCKAS<u>GYTFTNYVIH</u>WVKQKPGQGLEWIG<u>YFNPYN</u>

<u>DGTEYNEKFKA</u>KATLTSDKSSSTAYMELSSLTSEDSAVYYCAK<u>GPYYYGSSPFDY</u>W

GQGTTLTVSS

Nucleic acid sequence (SEQ ID NO: 95):
GAGGTCCAGCTGCAGCAGTCTGGACCTGAGCTGGTAAAGCCTGGGGCTTCAGTG

AAGATGTCCTGCAAGGCTTCTGGATACACATTCACTAACTATGTTATTCACTGGG

TGAAGCAGAAGCCTGGGCAGGGCCTTGAGTGGATTGGATATTTTAATCCTTACAA

TGATGGTACTGAATACAATGAGAAGTTCAAAGCCAAGGCCACACTGACTTCAGA

CAAATCCTCCAGCACAGCCTACATGGAGCTCAGCAGCCTGACCTCTGAGGACTCT

GCGGTCTATTACTGTGCAAAAGGTCCCTACTACTACGGTAGTAGCCCCTTTGACT

ACTGGGGCCAAGGCACCACTCTCACAGTCTCCTCA

WBP7011-4.34.11-VK
Amino acid sequence (SEQ ID NO: 96):
DAVMTQTPLSLPVSLGDQASISC<u>RSSQSLENSNGNTYLN</u>WYLQKPGQSPQLLIY<u>RVS</u>

<u>NRFS</u>GVLDRFSGSGSGTDFTLKISRVEAEDLGVYFC<u>LQVTHVPYT</u>FGGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011-4.87.6-VH
Amino acid sequence (SEQ ID NO: 98):
QVQLQQSGAELVRPGSSVKISCKAS<u>GYAFSTYWMN</u>WVKQRPGQGLEWIG<u>QIYPGD</u>

<u>DDTKYNGKFKG</u>KASLTADKSSSTAYMQLISLTSEDSAVYFCAR<u>RYFRYDWYSDV</u>

WGAGTTVTVTS

Nucleic acid sequence (SEQ ID NO: 99):
CAGGTTCAACTGCAGCAGTCTGGGGCTGAGCTGGTGAGGCCTGGGTCCTCAGTG

AAGATTTCCTGCAAGGCTTCTGGCTATGCATTCAGTACCTATTGGATGAACTGGG

TGAAGCAGAGGCCTGGACAGGGTCTTGAGTGGATTGGACAGATTTATCCTGGAG

ATGATGATACTAAGTACAATGGAAAGTTCAAGGGTAAAGCCTCACTGACTGCAG

ACAAATCCTCCAGCACCGCCTACATGCAGCTCATCAGCCTAACATCTGAGGACTC

```
TGCGGTCTATTTCTGTGCAAGAAGATACTTTAGGTACGACTACTGGTATTCCGAT

GTCTGGGGCGCAGGGACCACGGTCACCGTCACCTCA

WBP7011-4.87.6-VK
Amino acid sequence (SEQ ID NO: 100):
DIQMTQTTSSLSASLGDRVTISCRASQDISNYLNWYQQKPDGTVKLLIYYTSRLHSGV

PARFSGSGSGTDYSLTISNLEQEDIATYFCHQGNTLPLTFGAGTKLELK

Nucleic acid sequence (SEQ ID NO: 101):
GATATCCAGATGACACAGACTACATCCTCCCTGTCTGCCTCTCTGGGAGACAGAG

TCACCATCAGTTGCAGGGCAAGTCAGGACATTAGCAATTATTTAAACTGGTATCA

GCAGAAACCGGATGGAACTGTTAAACTCCTGATCTATTACACATCAAGATTACAC

TCAGGAGTCCCAGCAAGATTCAGTGGCAGTGGGTCTGGAACAGATTACTCTCTCA

CCATTAGTAACCTGGAACAAGAAGATATTGCCACTTACTTTTGCCACCAGGGTAA

TACGCTTCCGCTCACGTTCGGTGCTGGGACCAAGCTGGAGCTGAAA

WBP7011-4.155.8-VH
Amino acid sequence (SEQ ID NO: 102):
EIQLQQSGPELVKPGASVKVSCKASGYAFTSYNMYWVKQSHGKSLEWIGYIDPYNG

DTTYNQKFKGKATLTVDKSSSTAYMHLNSLTSEDSAVYYCLTTAYAMDYWGQGTS

VTVSS

Nucleic acid sequence (SEQ ID NO: 103):
GAGATCCAGCTGCAGCAGTCTGGACCTGAGCTGGTGAAGCCTGGGGCTTCAGTG

AAGGTATCCTGCAAGGCTTCTGGTTATGCATTCACTAGCTACAACATGTACTGGG

TGAAGCAGAGCCATGGAAAGAGCCTTGAGTGGATTGGATATATTGATCCTTACA

ATGGTGATACTACCTACAACCAGAAGTTCAAGGGCAAGGCCACATTGACTGTTG

ACAAGTCCTCCAGCACAGCCTACATGCATCTCAACAGCCTGACATCTGAGGACTC

TGCAGTCTATTACTGTCTCACTACGGCCTATGCTATGGACTACTGGGGTCAAGGA

ACCTCAGTCACCGTCTCCTCA

WBP7011-4.155.8-VK
Amino acid sequence (SEQ ID NO: 104):
QIVLTQSPAIMSASLGEEITLTCSASSTVNYMHWYQQKSGTSPKLLIYSTSNLASGVPS

RFSGSGSGTFYSLTIRSVEAEDAADYYCHQWSSYPYTFGGGTKLEIK

Nucleic acid sequence (SEQ ID NO: 105):
CAAATTGTTCTCACCCAGTCTCCAGCAATCATGTCTGCATCTCTAGGGGAGGAGA

TCACCCTAACCTGCAGTGCCAGCTCGACTGTAAATTACATGCACTGGTACCAGCA

GAAGTCAGGCACTTCTCCCAAACTCTTGATTTATAGCACATCCAACCTGGCTTCT

GGAGTCCCTTCTCGCTTCAGTGGCAGTGGGTCTGGGACCTTTTATTCTCTCACAAT

CAGAAGTGTGGAGGCTGAAGATGCTGCCGATTATTACTGCCATCAGTGGAGTAG

TTATCCGTACACGTTCGGAGGGGGGACCAAGCTGGAAATAAAA

WBP7011_4.56.1-VH
Amino acid sequence (SEQ ID NO: 106):
EVQLQQSGPELVKPGASVKMSCKASGYTFTNYVIHWVKQKPGQGLEWIGYINPYND

GTEYNEKFKGKATLTSDTSSSTAYMALSSLTSEDSAVYYCTRGPYYYGGSPFDYWG

QGTTLTVSS

Nucleic acid sequence (SEQ ID NO: 107):
GAGGTCCAGCTGCAGCAGTCTGGACCTGAGCTGGTAAAGCCTGGGGCTTCAGTG

AAGATGTCCTGCAAGGCTTCTGGATACACATTCACTAACTATGTTATACACTGGG

TGAAGCAGAAGCCTGGGCAGGGCCTTGAGTGGATTGGATATATTAATCCTTACA

ATGATGGTACTGAGTACAATGAGAAGTTCAAGGGCAAGGCCACACTGACTTCAG
```

ACACATCCTCCAGCACAGCCTACATGGCGCTCAGCAGCCTGACCTCTGAGGACTC

TGCGGTCTATTACTGTACAAGAGGACCCTATTACTACGGTGGTAGCCCCTTCGAC

TACTGGGGCCAAGGCACCACTCTCACAGTCTCCTCA

WBP7011_4.56.1-VK
Amino acid sequence (SEQ ID NO: 96):
DAVMTQTPLSLPVSLGDQASISCRSSQSLENSNGNTYLNWYLQKPGQSPQLLIYRVS

NRFSGVLDRFSGSGSGTDFTLKISRVEAEDLGVYFCLQVTHVPYTFGGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011_4.15.10-VH
Amino acid sequence (SEQ ID NO: 108):
EVQLQQSGPELVKPGASVKMSCKASGYTFTSYVMHWMKQKPGQGLEWIGYINPYN

DGTEYHEKFKGKATLTSDKSSSTAYMELSSLTSEDSAVFYCARGPYYYGGSPFDFWG

QGTTLTVSS

Nucleic acid sequence (SEQ ID NO: 109):
GAGGTCCAGCTGCAGCAGTCTGGGCCTGAGCTGGTAAAGCCTGGGGCTTCAGTG

AAGATGTCCTGCAAGGCTTCTGGATACACATTCACTAGCTATGTTATGCACTGGA

TGAAACAGAAGCCTGGGCAGGGCCTTGAGTGGATTGGATATATTAATCCTTACA

ATGATGGTACTGAGTACCATGAGAAGTTCAAAGGCAAGGCCACACTGACTTCAG

ACAAATCCTCCAGCACAGCCTACATGGAGCTCAGCAGCCTGACCTCTGAGGACTC

TGCGGTCTTTTACTGTGCAAGAGGACCCTATTACTACGGTGGTAGCCCCTTTGAC

TTCTGGGGCCAAGGCACCACTCTCACGGTCTCCTCA

WBP7011_4.15.10-VK
Amino acid sequence (SEQ ID NO: 96):
DAVMTQTPLSLPVSLGDQASISCRSSQSLENSNGNTYLNWYLQKPGQSPQLLIYRVS

NRFSGVLDRFSGSGSGTDFTLKISRVEAEDLGVYFCLQVTHVPYTFGGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011_4.100.1-VH
Amino acid sequence (SEQ ID NO: 110):
EVQLQQSGPELVKPGASVKMSCKASGYTFTSYVIHWVKQKPGQGLEWIGYINPYND

GAEYTEKFKGKATLTSDKSSSTAYMELSSLTSEDSTVYYCARGPYYYGGSPFDYWG

QGTTLTVSS

-continued

Nucleic acid sequence (SEQ ID NO: 111):
GAGGTCCAGCTGCAGCAGTCTGGACCTGAGCTGGTAAAGCCTGGGGCTTCAGTG

AAGATGTCCTGCAAGGCTTCTGGATACACATTCACTAGCTATGTTATACACTGGG

TGAAGCAGAAGCCTGGGCAGGGCCTTGAGTGGATTGGATATATTAATCCTTACA

ATGATGGTGCTGAGTACACTGAGAAGTTCAAGGGCAAGGCCACACTGACTTCAG

ACAAATCCTCCAGTACTGCCTATATGGAGCTCAGCAGCCTGACCTCTGAGGACTC

TACGGTCTATTACTGTGCACGAGGACCCTATTACTACGGTGGTAGCCCCTTTGAC

TACTGGGGCCAAGGCACCACTCTCACAGTCTCCTCA

WBP7011_4.100.1-VK
Amino acid sequence (SEQ ID NO: 96):
DAVMTQTPLSLPVSLGDQASISCRSSQSLENSNGNTYLNWYLQKPGQSPQLLIYRVS

NRFSGVLDRFSGSGSGTDFTLKISRVEAEDLGVYFCLQVTHVPYTFGGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011_4.106.3-VH
Amino acid sequence (SEQ ID NO: 112):
EVQLQQSGPELVKPGASVKMSCKASGYTFSSYVIHWVKQKPGQGLEWIGYINPYND

GAEYAEKFKGKATLTSDKSSSAYMELGSLTSEDSAVYYCARGPYYYGGSPFDYWG

QGTTLTVSS

Nucleic acid sequence (SEQ ID NO: 113):
GAGGTCCAGCTGCAGCAGTCTGGACCTGAGCTGGTAAAGCCTGGGGCTTCAGTG

AAGATGTCCTGCAAGGCTTCTGGATACACATTCAGTAGTTATGTTATACACTGGG

TGAAGCAGAAGCCTGGGCAGGGCCTTGAGTGGATTGGATATATTAATCCTTACA

ATGATGGTGCTGAGTATGCTGAGAAGTTCAAGGGCAAGGCCACACTGACTTCAG

ACAAATCCTCCAGTTCTGCCTATATGGAGCTCGGCAGCCTGACCTCTGAGGACTC

TGCGGTCTATTACTGTGCACGAGGACCCTATTACTACGGTGGTAGTCCCTTTGAC

TACTGGGGCCAAGGCACCACTCTCACAGTCTCCTCA

WBP7011_4.106.3-VK
Amino acid sequence (SEQ ID NO: 96):
DAVMTQTPLSLPVSLGDQASISCRSSQSLENSNGNTYLNWYLQKPGQSPQLLIYRVS

NRFSGVLDRFSGSGSGTDFTLKISRVEAEDLGVYFCLQVTHVPYTFGGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

-continued

WBP7011_4.108.3-VH
Amino acid sequence (SEQ ID NO: 114):
EVQLQQSGPELVKPGASVEMSCKAS<u>GYTFTSYVIH</u>WLKQKPGQGLEWIG<u>YINPYND</u>

<u>GAEYNEKFKG</u>KATLTSDKSSTAYMDLNSLTSEDSAVYYCAR<u>GPYYYGSSPFDY</u>WG

QGTTLTVSS

Nucleic acid sequence (SEQ ID NO: 115):
GAGGTCCAGCTGCAGCAGTCTGGACCTGAGCTGGTGAAGCCTGGGGCTTCAGTG

GAGATGTCCTGCAAGGCTTCTGGATACACATTCACTAGCTATGTTATTCACTGGT

TGAAGCAGAAGCCTGGGCAGGGCCTTGAGTGGATTGGATATATTAATCCTTACA

ATGATGGTGCTGAGTATAATGAGAAGTTCAAGGGCAAGGCCACACTGACTTCAG

ACAAATCCTCCAGTACAGCCTATATGGATCTCAACAGCCTGACCTCTGAGGACTC

TGCGGTCTATTACTGTGCAAGAGGACCCTATTACTACGGTAGTAGCCCCTTTGAC

TACTGGGGCCAAGGCACCACTCTCACAGTCTCCTCA

WBP7011_4.108.3-VK
Amino acid sequence (SEQ ID NO: 96):
DAVMTQTPLSLPVSLGDQASISC<u>RSSQSLENSNGNTYLN</u>WYLQKPGQSPQLLIY<u>RVS</u>

<u>NRFS</u>GVLDRFSGSGSGTDFTLKISRVEAEDLGVYFC<u>LQVTHVPYTF</u>GGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGCAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011_4.191.6-VH
Amino acid sequence (SEQ ID NO: 116):
EVQLLQSGPELVKPGASVKMSCKAS<u>GYTFTDYVIH</u>WVKQRPGQGLEWIG<u>YINPYND</u>

<u>GSEYSEKFKG</u>KATLTSDKSSTAYMELSSLTSEDSAVYYCAR<u>GPYYYGGSPFDY</u>WG

QGTTLTVSS

Nucleic acid sequence (SEQ ID NO: 117):
GAGGTCCAGCTGCTGCAGTCTGGACCTGAGCTGGTAAAGCCTGGGGCTTCAGTG

AAGATGTCCTGCAAGGCTTCTGGATACACATTCACTGACTATGTTATACACTGGG

TGAAGCAGAGGCCTGGGCAGGGCCTTGAGTGGATTGGATATATTAATCCTTACA

ATGATGGTTCTGAGTACAGTGAGAAGTTCAAAGGCAAGGCCACACTGACTTCAG

ACAAATCCTCCAGCACAGCCTACATGGAGCTCAGCAGCCTGACCTCTGAGGACTC

TGCGGTCTATTACTGTGCAAGAGGACCCTATTACTACGGTGGTAGTCCCTTTGAC

TACTGGGGCCAAGGCACCACTCTCACAGTCTCCTCA

WBP7011_4.191.6-VK
Amino acid sequence (SEQ ID NO: 96):
DAVMTQTPLSLPVSLGDQASISC<u>RSSQSLENSNGNTYLN</u>WYLQKPGQSPQLLIY<u>RVS</u>

<u>NRFS</u>GVLDRFSGSGSGTDFTLKISRVEAEDLGVYFC<u>LQVTHVPYTF</u>GGGTKLEIK

Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGCAGTGGATCAGGGA

-continued

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA

WBP7011_4.194.10-VH
Amino acid sequence (SEQ ID NO: 118):
EVQLQQSGPELVKPGASVKMSCKAS<u>GYTFTSYVMH</u>WVKQKPGQGLEWIG<u>YINPYN</u>

<u>DGTKYNEKFKG</u>KATLTSDKSSSTAYMELSSLTSEDSAVYYCAR<u>GPYYYGSSPFDY</u>W

GQGTTLTVSS

Nucleic acid sequence (SEQ ID NO: 119):
GAGGTCCAGCTGCAGCAGTCTGGACCTGAGCTGGTAAAGCCTGGGGCTTCAGTG

AAGATGTCCTGCAAGGCTTCTGGATACACATTCACTAGCTATGTTATGCACTGGG

TGAAGCAGAAGCCTGGGCAGGGCCTTGAGTGGATTGGATATATTAATCCTTACA

ATGATGGTACTAAGTACAATGAGAAGTTCAAAGGCAAGGCCACACTGACTTCAG

ACAAATCCTCCAGCACAGCCTACATGGAACTCAGCAGCCTGACCTCTGAGGACTC

TGCGGTCTATTACTGTGCAAGAGGACCCTATTACTACGGTAGTAGCCCCTTTGAC

TACTGGGGCCAAGGCACCACTCTCACAGTCTCCTCA

WBP7011_4.194.10-VK
Amino acid sequence (SEQ ID NO: 120):
DAVMTQTPLSLPVSLGDQASISC<u>RSSQTLENSNGNTYLN</u>WYLQKPGQSPQLLIY<u>RVS</u>

<u>NRFS</u>GVLDRFSGSGSGTDFTLKISRVETEDLGVYFC<u>LQVTHVPYTF</u>GGGTKLEIK

Nucleic acid sequence (SEQ ID NO: 121):
GATGCTGTGATGACCCAAACTCCACTCTCCCTGCCTGTCAGTCTTGGAGATCAAG

CCTCCATCTCTTGCAGGTCTAGTCAGACCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTAGACAGGTTCAGTGGTAGTGGATCAGGGA

CAGATTTCACACTGAAAATCAGCAGAGTGGAGACTGAGGATTTGGGAGTTTATTT

CTGCCTCCAAGTTACACATGTCCCGTACACGTTCGGAGGGGGGACCAAGCTGGA

AATAAAA

WBP7011_4.231.5-VH
Amino acid sequence (SEQ ID NO: 122):
EVQLQQSGPELVKPGASVKMSCKAS<u>GYTFTSYVMH</u>WVKQKPGQGLEWIG<u>YINPYN</u>

<u>DGTQYNEKFKG</u>KATLTSDKSSSTAYMELSSLTSEDSAVYYCAR<u>GPYYYSPSPFDY</u>W

GQGTTLTVSS

Nucleic acid sequence (SEQ ID NO: 123):
GAGGTCCAGCTGCAGCAGTCTGGACCTGAGCTGGTAAAGCCTGGGGCTTCAGTG

AAGATGTCCTGCAAGGCTTCTGGATACACATTCACTAGCTATGTCATGCACTGGG

TGAAGCAGAAGCCTGGGCAGGGCCTTGAGTGGATTGGATATATTAATCCTTACA

ATGATGGTACTCAGTACAATGAGAAGTTTAAAGGCAAGGCCACACTGACTTCAG

ACAAATCCTCCAGCACAGCCTACATGGAGCTCAGCAGCCTGACCTCTGAGGACTC

TGCGGTCTATTACTGTGCAAGAGGACCCTATTACTACAGTCCTAGCCCCTTTGAC

TACTGGGGCCAAGGCACCACTCTCACAGTCTCCTCA

WBP7011_4.231.5-VK
Amino acid sequence (SEQ ID NO: 96):
DAVMTQTPLSLPVSLGDQASISC<u>RSSQSLENSNGNTYLN</u>AVYLQKPGQSPQLLIY<u>RVS</u>

<u>NRFS</u>GVLDRFSGSGSGTDFTLKISRVEAEDLGVYFC<u>LQVTHVPYTF</u>GGGTKLEIK

-continued
```
Nucleic acid sequence (SEQ ID NO: 97):
GATGCTGTGATGACCCAAACTCCACTCTCCCTGCCTGTCAGTCTTGGAGATCAAG

CCTCCATCTCTTGCAGGTCTAGTCAGAGCCTTGAAAACAGTAATGGAAACACCTA

TTTGAACTGGTACCTCCAGAAACCAGGCCAGTCTCCACAGCTCCTGATCTACAGG

GTTTCCAACCGATTTTCTGGGGTCCTTGACAGGTTCAGTGGTAGTGGATCAGGGA

CAGATTTCACACTGAAAATCAGTAGAGTGGAGGCTGAGGATTTGGGAGTTTATTT

CTGTCTCCAAGTTACACATGTCCCGTACACGTTCGGAGGGGGGACCAAGCTGGA

AATAAAA
```

CDRs are known to be responsible for antigen binding, however, it has been found that not all of the 6 CDRs are indispensable or unchangeable. In other words, it is possible to replace or change or modify 1, 2, or 3 CDRs in anti-CD19 antibodies WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.231.5, W7011-4.34.11-z1-m5, W7011-4.87.6-z1(N-S), or W7011-4.155.8-z1-P15, yet substantially retain the specific binding affinity to CD19.

In certain embodiments, the anti-CD19 antibodies and the antigen-binding fragments provided herein comprise a heavy chain CDR3 sequence of one of the anti-CD19 antibodies WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.231.5, W7011-4.34.11-z1-m5, W7011-4.87.6-z1(N-S), or W7011-4.155.8-z1-P15. In certain embodiments, the anti-CD19 antibodies and the antigen-binding fragments provided herein comprise a heavy chain CDR3 sequence selected from the group consisting of SEQ ID NOs: 3, 9, 15, 21, 24, 27, 30, 33, 36, 39, and 45. Heavy chain CDR3 regions are located at the center of the antigen-binding site, and therefore are believed to make the most contact with antigen and provide the most free energy to the affinity of antibody to antigen. It is also believed that the heavy chain CDR3 is by far the most diverse CDR of the antigen-binding site in terms of length, amino acid composition and conformation by multiple diversification mechanisms (Tonegawa S. Nature. 302:575-81). The diversity in the heavy chain CDR3 is sufficient to produce most antibody specificities (Xu J L, Davis M M. Immunity. 13:37-45) as well as desirable antigen-binding affinity (Schier R, etc. J Mol Biol. 263:551-67).

In certain embodiments, the antibodies and antigen-binding fragments thereof provided herein comprise suitable framework region (FR) sequences, as long as the antibodies and antigen-binding fragments thereof can specifically bind to CD19. The CDR sequences provided in Table 1 are obtained from mouse antibodies, but they can be grafted to any suitable FR sequences of any suitable species such as mouse, human, rat, rabbit, among others, using suitable methods known in the art such as recombinant techniques.

In certain embodiments, the antibodies and antigen-binding fragments thereof provided herein are humanized. A humanized antibody or antigen-binding fragment is desirable in its reduced immunogenicity in human. A humanized antibody is chimeric in its variable regions, as non-human CDR sequences are grafted to human or substantially human FR sequences. Humanization of an antibody or antigen-binding fragment can be essentially performed by substituting the non-human (such as murine) CDR genes for the corresponding human CDR genes in a human immunoglobulin gene (see, for example, Jones et al. (1986) Nature 321:522-525; Riechmann et al. (1988) Nature 332:323-327; Verhoeyen et al. (1988) Science 239:1534-1536).

Suitable human heavy chain and light chain variable domains can be selected to achieve this purpose using methods known in the art. In an illustrative example, "best-fit" approach can be used, where a non-human (e.g., rodent) antibody variable domain sequence is screened or BLASTed against a database of known human variable domain sequences, and the human sequence closest to the non-human query sequence is identified and used as the human scaffold for grafting the non-human CDR sequences (see, for example, Sims et al, (1993) J. Immunol. 151:2296; Chothia et al. (1987) J. Mot. Biol. 196:901). Alternatively, a framework derived from the consensus sequence of all human antibodies may be used for the grafting of the non-human CDRs (see, for example, Carter et al. (1992) Proc. Natl. Acad. Sci. USA, 89:4285; Presta et al. (1993) J. Immunol., 151:2623).

In certain embodiments, the humanized antibodies or antigen-binding fragments provided herein are composed of substantially all human sequences except for the CDR sequences which are non-human. In some embodiments, the variable region FRs, and constant regions if present, are entirely or substantially from human immunoglobulin sequences. The human FR sequences and human constant region sequences may be derived different human immunoglobulin genes, for example, FR sequences derived from one human antibody and constant region from another human antibody. In some embodiments, the humanized antibody or antigen-binding fragment comprise human heavy/light chain FR1-4.

In certain embodiments, the humanized antibodies and antigen-binding fragment thereof provided herein comprise one or more FR sequences of W7011-4.34.11-z1-m5, W7011-4.87.6-z1(N-S) or W7011-4.155.8-z1-P15. Table 2 below shows the FR sequences of W7011-4.34.11-z1-m5, W7011-4.87.6-z1(N-S) or W7011-4.155.8-z1-P15. The corresponding native mouse FR sequences are also provided in Table 2. The heavy chain and light chain variable region sequences are also provided below.

TABLE 2

| | FR1 | FR2 | FR3 | FR4 |
|---|---|---|---|---|
| WBP7011-4.34.11-VH | SEQ ID NO: 46 EVQLQQSGPELVK PGASVKMSCKAS | SEQ ID NO: 47 WVKQRPG QGLEWIG | SEQ ID NO: 48 KATLTSDKSSSTAYME LSSLTSEDSAVYYCAK | SEQ ID NO: 49 WGQGT TLTVSS |
| W7011-4.34.11-z1-m5-VH | SEQ ID NO: 54 QVQLVQSGAEVK KPGSSVKVSCKAS | SEQ ID NO: 55 WVRQAPG QGLEWMG | SEQ ID NO: 56 RVTITADKSTSTAYME LSSLRSEDTAVYYCAR | SEQ ID NO: 57 WGQGT TVTVSS |
| WBP7011-4.34.11-VK | SEQ ID NO: 50 DAVMTQTPLSLPV SLGDQASISC | SEQ ID NO: 51 WYQQKPG QSPKLLIY | SEQ ID NO: 52 GVLDRFSGSGSGTDFTL KISRVEAEDLGVYFC | SQ ID NO: 53 FGGGT KLEIK |
| W7011-4.34.11-z1-m5-VK | SEQ ID NO: 58 DIVMTQTPLSLPV TPGEPASISC | SEQ ID NO: 59 WYLQKPG QSPQLLIY | SEQ ID NO: 60 GVPDRFSGSGSGTDFTL KISRVEAEDVGVYYC | SEQ ID NO: 61 FGQGT KLEIK |
| WBP7011-4.87.6-VH | SEQ ID NO: 62 QVQLQQSGAELVR PGSSVKISCKAS | SEQ ID NO: 63 WVKQRPG QGLE WIG | SEQ ID NO: 64 KASLTADKSSSTAYMQ LISLTSEDSAVYFCAR | SEQ ID NO: 65 WGAGT TVTVTS |
| W7011-4.87.6-z1(N-S)-VH | SEQ ID NO: 70 QVQLVQSGAEVK KPGASVKVSCKAS | SEQ ID NO: 71 WVRQAPG QGLEWMG | SEQ ID NO: 72 RVTITADKSTSTAYME LSSLRSEDTAVYYCAR | SEQ ID NO: 73 WGQGT TVTVSS |
| WBP7011-4.87.6-VK | SEQ ID NO: 66 DIQMTQTTSSLSAS LGDRVTISC | SEQ ID NO: 67 WYQQKPD GTVKLLIY | SEQ ID NO: 68 GVPARFSGSGSGTDYS LTISNLEQEDIATYFC | SEQ ID NO: 69 FGAGT KLELK |
| W7011-4.87.6-z1(N-S)-VK | SEQ ID NO: 74 DIQMTQSPSSLSAS VGDRVTITC | SEQ ID NO: 75 WYQQKPG KVPKLLIY | SEQ ID NO: 76 GVPSRFSGSGSGTDFTL TISSLQPEDVATYYC | SEQ ID NO: 77 FGQGT KLEIK |
| WBP7011_4.155.8-VH | SEQ ID NO: 78 EIQLQQSGPELVKP GASVKVSCKAS | SEQ ID NO: 79 WVKQSHG KSLEWIG | SEQ ID NO: 80 KATLTVDKSSSTAYMH LNSLTSEDSAVYYCLT | SEQ ID NO: 81 WGQGT SVTVSS |
| W7011-4.155.8-z1-P15-VH | SEQ ID NO: 86 QMQLVQSGPEVK KPGTSVKVSCKAS | SEQ ID NO: 87 WVRQARG QRLEWIG | SEQ ID NO: 88 RVTITRDMSTAYME LSSLRSEDTAVYYCLT | SEQ ID NO: 89 WGQGT LVTVSS |
| WBP7011_4.155.8-VK | SEQ ID NO: 82 QIVLTQSPAIMSAS LGEEITLTC | SEQ ID NO: 83 WYQQKSG TSPKLLIY | SEQ ID NO: 84 GVPSRFSGSGSGTFYSL TIRSVEAEDAADYYC | SEQ ID NO: 85 FGGGT KLEIK |
| W7011-4.155.8-z1-P15-VK | SEQ ID NO: 90 DIQLTQSPSFLSAS VGDRVTITC | SEQ ID NO: 91 WYQQKPG KAPKLLIY | SEQ ID NO: 92 GVPSRFSGSGSGTEFTL TISSLQPEDFATYYC | SEQ ID NO: 93 FGQGT KLEIK |

W7011-4.34.11-z1-m5-VH
Amino acid sequence (SEQ ID NO: 124):
QVQLVQSGAEVKKPGSSVKVSCKAS<u>GYTFTDYVIH</u>WVRQAPGQGLEWMG<u>YFNPYN</u>
<u>DGTEYNEKFKA</u>RVTITADKSTSTAYMELSSLRSEDTAVYYCAR<u>GPYYYGSSPFDY</u>W
GQGTTVTVSS Nucleic acid sequence (SEQ ID NO: 125):
CAGGTGCAGCTTGTGCAGTCTGGAGCTGAAGTGAAGAAGCCAGGATCCTCCGTG
AAGGTCTCCTGTAAGGCTTCTGGCTACACCTTCACCGATTACGTGATCCACTGGG
TCAGGCAGGCCCCTGGGCAAGGCTTGGAGTGGATGGGGTACTTTAACCCCTACA
ACGATGGGACTGAGTACAATGAGAAGTTTAAAGCACGGTTGACCATTACCGCCG
ACAAGAGCACAAGCACAGCCTACATGGAGCTGTCCAGCCTCCGCAGCGAGGATA
CAGCCGTCTACTACTGCGCCAGAGGCCCTTACTACTATGGGTCCAGCCCCTTCGA
CTATTGGGGCCAGGGGACTACAGTGACTGTCAGTTCA W7011-4.34.11-z1-m5-VK
Amino acid sequence (SEQ ID NO: 126):
DIVMTQTPLSLPVTPGEPASISC<u>RSSQSLENSNHNTYIN</u>WYLQKPGQSPQLLIY<u>RVSKR</u>
<u>FS</u>GVPDRFSGSGSGTDFTLKISRVEAEDVGVYYC<u>HQVTHVPYT</u>FGQGTKLEIK Nucleic acid sequence (SEQ ID NO: 127):
GATATCGTGATGACCCAGACTCCCCTGTCCCTTCCTGTGACCCCAGGAGAACCAG
CTTCTATCAGCTGTAGGTCCTCACAGAGCCTGGAGAACTCCAACCACAACACTTA
CATAAACTGGTACCTCCAGAAGCCTGGGCAGTCTCCCCAGTTGCTGATCTACAGG
GTCAGCAAACGCTTCTCCGGGGTGCCCGATCGGTTTAGTGGGAGCGGGAGCGGC
ACAGACTTTACACTCAAGATTTCCAGAGTGGAGGCCGAGGACGTCGGCGTCTATT
ACTGCCACCAAGTGACACACGTGCCCTACACATTCGGCCAGGGCACTAAACTGG
AGATTAAG

TABLE 2-continued

| FR1 | FR2 | FR3 | FR4 |
|---|---|---|---|

W7011-4.87.6-z1(N-S)-VH
Amino acid sequence (SEQ ID NO: 128):
QVQLVQSGAEVKKPGASVKVSCKAS<u>GYAFSTYWMN</u>WVRQAPGQGLEWMG<u>QIYPG
DDDTKYSGKFKG</u>RVTITADKSTSTAYMELSSLRSEDTAVYYCAR<u>RYFRYDYWYSDV</u>
WGQGTTVTVSS Nucleic acid sequence (SEQ ID NO: 129):
CAGGTCCAGCTTGTCCAGTCTGGAGCAGAAGTGAAGAAGCCAGGGGCTTCAGTG
AAGGTGTCTTGCAAGGCTTCCGGATACGCCTTCTCCACTTACTGGATGAACTGGG
TGCGCCAGGCCCCTGGGCAGGGCTTGGAGTGGATGGGCCAGATCTATCCCGGCG
ATGACGACACAAAATACAGCGGGAAGTTCAAGGGGCGGGTGACCATTACCGCCG
ATAAAAGCACCTCCACCGCCTACATGGAGCTCAGTTCCCTGAGAAGCGAGGATA
CAGCCGTGTACTACTGTGCCAGGAGGTACTTTCGGTACGACTACTGGTATAGCGA
CGTCTGGGGCAAGGCACAACTGTCACAGTGAGCAGC W7011-4.87.6-z1(N-S)-VK
Amino acid sequence (SEQ ID NO: 130):
DIQMTQSPSSLSASVGDRVTITC<u>RASQDISNYLN</u>WYQQKPGKVPKLLIY<u>YTSRLHS</u>GV
PSRFSGSGSGTDFTLTISSLQPEDVATYYC<u>HQGNTLPLT</u>FGQGTKLEIK Nucleic acid sequence (SEQ ID NO: 131):
GACATCCAAATGACCCAGAGCCCTTCCTCCTTGTCCGCAAGTGTGGGAGATAGAG
TGACCATCACCTGCAGGGCTTCTCAGGATATCTCCAACTACCTGAACTGGTATCA
GCAGAAGCCCGGCAAGGTGCCAAAGCTCCTTATTTACTACACCTCCCGGCTGCAC
AGCGGAGTCCCATCTCGCTTCAGCGGGTCAGGCAGCGGCACTGACTTTACTCTGA
CAATTAGCAGCCTCCAGCCTGAAGACGTCGCCACTTACTACTGTCATCAGGGGAA
TACACTCCCCCTGACATTCGGGCAGGGGACAAAACTGGAGATTAAG W7011-4.155.8-z1-P15-VH
Amino acid sequence (SEQ ID NO: 132):
QMQLVQSGPEVKKPGTSVKVSCKAS<u>GYAFTSYNMY</u>WVRQARGQRLEWIG<u>YIDPYN
ADTTYNQKFKG</u>RVTITRDMSTSTAYMELSSLRSEDTAVYYCLT<u>TAYAMD</u>YWGQGT
LVTVSS Nucleic acid sequence (SEQ ID NO: 133):
CAAATGCAGCTCGTCCAGTCTGGACCTGAAGTGAAGAAGCCCGGGACATCCGTC
AAGGTCTCATGTAAGGCTAGCGGGTACGCATTCACTTCCTACAACATGTACTGGG
TGCGCCAGGCCAGAGGACAGAGGTTGGAGTGGATCGGCTACATCGACCCATACA
ACGCCGATACTACCTACAATCAGAAGTTTAAAGGGCGGGTGACCATTACCCGGG
ATATGTCCACCTCCACCGCCTACATGGAGCTGAGCAGCCTGAGGAGCGAGGACA
CAGCCGTGTACTACTGCCTGACAACAGCCTATGCCATGGACTATTGGGGCCAGGG
CACACTTGTGACTGTGAGCAGT W7011-4.155.8-z1-P15-VK
Amino acid sequence (SEQ ID NO: 134):
DIQLTQSPSFLSASVGDRVTITC<u>SASSTVNYMH</u>WYQQKPGKAPKLLIY<u>STSNLAS</u>GVP
SRFSGSGSGTEFTLTISSLQPEDFATYYC<u>HQWSSYPYT</u>FGQGTKLEIK Nucleic acid sequence (SEQ ID NO: 135):
GACATCCAGCTCACCCAATCCCCTTCTTTCCTCTCCGCAAGTGTCGGAGATAGGG
TGACTATCACCTGCTCAGCTTCTTCAACCGTGAACTACATGCATTGGTACCAGCA
GAAGCCCGGGAAAGCCCCAAAGCTGCTGATCTACAGCACCTCCAATCTGGCCAG
TGGAGTGCCAAGCCGGTTTAGCGGGAGCGGCTCCGGCACTGAATTCACTTTGACA
ATTAGCAGCCTTCAGCCTGAGGACTTTGCCACATATTACTGTCACCAGTGGTCCA
GCTACCCCTACACATTCGGGCAGGGCACAAAGCTGGAGATTAAG The exemplary humanized anti-CD19 antibodies W7011-4.34.11-z1-m5, W7011-4.87.6-z1(N-S) or W7011-4.155.8-z1-P15 all retained the specific binding affinity to CD3-expressing cell (e.g. CD4 T cell), and are at least comparable to, or even better than, the parent mouse antibodies in that aspect.

In some embodiments, the FR regions derived from human may comprise the same amino acid sequence as the human immunoglobulin from which it is derived. In some embodiments, one or more amino acid residues of the human FR are substituted with the corresponding residues from the parent non-human antibody. This may be desirable in certain embodiments to make the humanized antibody or its fragment closely approximate the non-human parent antibody structure. In certain embodiments, the humanized antibody or antigen-binding fragment provided herein comprises no more than 10, 9, 8, 7, 6, 5, 4, 3, 2, or 1 amino acid residue substitutions in each of the human FR sequences, or no more than 10, 9, 8, 7, 6, 5, 4, 3, 2, or 1 amino acid residue substitutions in all the FRs of a heavy or a light chain variable domain. In some embodiments, such change in amino acid residue could be present in heavy chain FR regions only, in light chain FR regions only, or in both chains.

In certain embodiments, the antibodies and antigen-binding fragments thereof provided herein comprise a heavy chain variable domain sequence selected from the group consisting of: SEQ ID NO: 94, SEQ ID NO: 98, SEQ ID NO: 102, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 122, SEQ ID NO: 124, SEQ ID NO: 128, SEQ ID NO: 132. In certain embodiments, the antibodies and antigen-binding fragments thereof provided herein comprise a light chain variable domain sequence selected from the group consisting of: SEQ ID NO: 96, SEQ ID NO: 100, SEQ ID NO: 104, SEQ ID NO: 120, SEQ ID NO: 126, SEQ ID NO: 130, SEQ ID NO: 134.

In some embodiments, the anti-CD19 antibodies and the antigen-binding fragments provided herein comprise all or a portion of the heavy chain variable domain and/or all or a portion of the light chain variable domain. In one embodiment, the anti-CD19 antibodies and the antigen-binding fragments provided herein is a single domain antibody which consists of all or a portion of the heavy chain variable domain provided herein. More information of such a single domain antibody is available in the art (see, e.g., U.S. Pat. No. 6,248,516).

In certain embodiments, the anti-CD19 antibodies and the fragments thereof provided herein further comprise an immunoglobulin constant region. In some embodiments, an immunoglobulin constant region comprises a heavy chain and/or a light chain constant region. The heavy chain constant region comprises CH1, hinge, and/or CH2-CH3 regions. In certain embodiments, the heavy chain constant region comprises an Fc region. In certain embodiments, the light chain constant region comprises Cκ.

In some embodiments, the anti-CD19 antibodies and antigen-binding fragments thereof have a constant region of IgG1, IgG2a or IgG2b isotype, which has reduced or depleted effector function such as ADCC or CDC, which can be evaluated by various assays known in the art, for example, Fc receptor binding assay, C1q binding assay, and cell lysis assay.

Binding affinity of the antibody and antigen-binding fragment provided herein can be represented by $K_D$ value, which represents the ratio of dissociation rate to association rate ($k_{off}/k_{on}$) when the binding between the antigen and antigen-binding molecule reaches equilibrium. The antigen-binding affinity (e.g., $K_D$) can be appropriately determined using suitable methods known in the art, including, for example, flow cytometry assay. In some embodiments, binding of the antibody to the antigen at different concentrations can be determined by flow cytometry, the determined mean fluorescence intensity (MFI) can be firstly plotted against antibody concentration, $K_D$ value can then be calculated by fitting the dependence of specific binding fluorescence intensity (Y) and the concentration of antibodies (X) into the one site saturation equation: $Y=B_{max}*X/(K_D+X)$ (Scarchard Analysis) using Prism version 5 (GraphPad Software, San Diego, Calif.), wherein $B_{max}$ refers to the maximum specific binding of the tested antibody to the antigen.

In certain embodiments, the anti-CD19 antibodies and antigen-binding fragments thereof provided herein are capable of specifically binding to human/Cynomolgus monkey CD19 expressed on a cell surface naturally or artificially. For example, human/Cynomolgus monkey CD19 DNA sequence can be cloned into an expression vector, and then transfected and expressed in 293F cells such that human/Cynomolgus monkey CD19 protein can be expressed on the surface of the transfected 293F cells.

In some embodiments, the anti-CD19 antibodies and the antigen-binding fragments thereof provided herein are capable of specifically binding to human CD19 expressed on surface of cells with a binding affinity ($K_D$) of no more than $5\times10^{-9}$M, no more than $1\times10^{-9}$M, no more than $9\times10^{-10}$ M, no more than $8\times10^{-10}$ M, no more than $7\times10^{-10}$ M, no more than $6\times10^{-10}$M, no more than $5\times10^{-10}$M, no more than $4\times10^{-10}$ M, no more than $3\times10^{-10}$ M, no more than $2\times10^{-10}$ M, or no more than $1\times10^{-10}$ M as measured by flow cytometry assay.

In certain embodiments, the anti-CD19 antibodies and antigen-binding fragments thereof provided herein cross-react with Cynomolgus monkey CD19 expressed on a cell surface.

Binding of the antibodies to CD19 expressed on a cell can also be represented by "half maximal effective concentration" ($EC_{50}$) value, which refers to the concentration of an antibody where 50% of its maximal effect (e.g., binding or inhibition etc.) is observed. The $EC_{50}$ value can be measured by methods known in the art, for example, sandwich assay such as ELISA, Western Blot, flow cytometry assay, and other binding assay. In certain embodiments, the antibodies and the fragments thereof provided herein specifically bind to human CD19 expressed on a cell with an EC50 of no more than 0.01 nM, no more than 0.02 nM, no more than 0.03 nM, no more than 0.04 nM, no more than 0.05 nM, no more than 0.1 nM, no more than 0.2 nM, no more than 0.3 nM, no more than 0.4 nM, no more than 0.5 nM, no more than 0.6 nM, no more than 0.7 nM, no more than 0.8 nM, no more than 0.9 nM, or no more than 1 nM by flow cytometry assay.

In certain embodiments, the antibodies and antigen-binding fragments thereof bind to Cynomolgus monkey CD19 with a binding affinity similar to that of human CD19. For example, binding of the exemplary antibodies WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.225.7, or WBP7011_4.231.5 to Cynomolgus monkey CD19 is at a similar affinity or $EC_{50}$ value to that of human CD19.

In certain embodiments, the antibodies and the antigen-binding fragments thereof provided herein specifically bind to Cynomolgus monkey CD19 expressed on a cell at an $EC_{50}$ of no more than 0.2 nM, no more than 0.5 nM, no more than 0.8 nM, no more than 1 nM, no more than 2 nM, or no more than 3 nM by flow cytometry assay.

In certain embodiments, the antibodies and the fragments thereof provided herein are internalized by a CD19-expressing cell at an $EC_{50}$ of no more than 1 pM, no more than 2 pM, no more than 3 pM, no more than 4 pM, no more than 5 pM, no more than 6 pM, no more than 7 pM, no more than 8 pM, no more than 9 pM, no more than 10 pM, no more than 11 pM, no more than 12 pM, no more than 13 pM, no more than 14 pM, no more than 15 pM, no more than 16 pM, no more than 17 pM, no more than 18 pM, no more than 19 pM, no more than 20 pM, no more than 21 pM, no more than 22 pM, no more than 23 pM, no more than 24 pM, no more than 25 pM, no more than 30 pM, no more than 35 pM, no more than 40 pM, no more than 45 pM, or no more than 50 pM by Fab-Zap assay.

In certain embodiments, the antibodies and the fragments thereof provided herein have a specific binding affinity to human CD19 which is sufficient to provide for diagnostic and/or therapeutic use. A number of therapeutic strategies targeting B cells by clinically used anti-human CD19 monoclonal antibodies.

The antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

Antibody Variants

The present disclosure also encompass various types of variants of the antibodies and antigen-binding fragments thereof provided herein. In certain embodiments, the present disclosure encompasses variants of an exemplary antibody provided herein, i.e., WBP7011-4.34.11, WBP7011-4.87.6, WBP7011_4.155.8, WBP7011_4.56.1, WBP7011-4.15.10, WBP7011-4.100.1, WBP7011-4.106.3, WBP7011_4.108.3, WBP7011_4.191.6, WBP7011_4.194.10, WBP7011_4.231.5, W7011-4.34.11-z1-m5, W7011-4.87.6-z1(N-S), or W7011-4.155.8-z1-P15.

In certain embodiments, the antibody variants comprise one or more modifications or substitutions in 1, 2, or 3 CDR sequences as provided in Table 1, one or more FR sequences provided in Table 2, the heavy or light chain variable region sequences provided herein, and/or the constant region (e.g., Fc region). Such antibody variants retain specific binding affinity to CD19 of their parent antibodies, but have one or more desirable properties conferred by the modification(s) or substitution(s). For example, the antibody variants may have improved antigen-binding affinity, improved glycosylation pattern, reduced risk of glycosylation, reduced deamination, reduced or depleted effector function(s), improved FcRn receptor binding, increased pharmacokinetic half-life, pH sensitivity, and/or compatibility to conjugation (e.g., one or more introduced cysteine residues).

A parent antibody sequence may be screened to identify suitable or preferred residues to be modified or substituted, using methods known in the art, for example "alanine scanning mutagenesis" (see, for example, Cunningham and Wells (1989) Science, 244:1081-1085). Briefly, target residues (e.g., charged residues such as Arg, Asp, His, Lys, and Glu) can be identified and replaced by a neutral or negatively charged amino acid (e.g., alanine or polyalanine), and the modified antibodies are produced and screened for the interested property. If substitution at a particular amino acid location demonstrates an interested functional change, then the position can be identified as a potential residue for modification or substitution. The potential residues may be further assessed by substituting with a different type of residue (e.g., cysteine residue, positively charged residue, etc.).

Affinity Variant

An affinity variant may contain modifications or substitutions in one or more CDR sequences as provided in Table 1, one or more FR sequences provided in Table 2, or the heavy or light chain variable region sequences provided herein. The affinity variants retain specific binding affinity to CD19 of the parent antibody, or even have improved CD19 specific binding affinity over the parent antibody. In certain embodiments, at least one (or all) of the substitution(s) in the CDR sequences, FR sequences, or variable region sequences comprises a conservative substitution.

A skilled artisan will understand that in the CDR sequences and FR sequences provided in Table 1 and Table 2, one or more amino acid residues may be substituted yet the resulting antibody or antigen-binding fragment still retain the binding affinity to CD19, or even have an improved binding affinity. Various methods known in the art can be used to achieve this purpose. For example, a library of antibody variants (such as Fab or scFv variants) can be generated and expressed with phage display technology, and then screened for the binding affinity to human CD19. For another example, computer software can be used to virtually simulate the binding of the antibodies to human CD19, and identify the amino acid residues on the antibodies which form the binding interface. Such residues may be either avoided in the substitution so as to prevent reduction in binding affinity, or targeted for substitution to provide for a stronger binding.

In certain embodiments, the humanized antibody or antigen-binding fragment provided herein comprises one or more amino acid residue substitutions in one or more CDR sequences, and/or one or more FR sequences. In certain embodiments, an affinity variant comprises no more than 10, 9, 8, 7, 6, 5, 4, 3, 2, or 1 substitutions in the CDR sequences and/or FR sequences in total.

In certain embodiments, the anti-CD19 antibodies and antigen-binding fragments thereof comprise 1, 2, or 3 CDR sequences having at least 80% (e.g., at least 85%, 88%, 90%, 91%, 92%, 93%, 94%, 95%, 96%, 97%, 98%, 99%) sequence identity to that (or those) listed in Table 1, and in the meantime retain the binding affinity to CD19 at a level similar to or even higher than its parental antibody.

In certain embodiments, the anti-CD19 antibodies and antigen-binding fragments thereof comprise one or more FR sequences having at least 80% (e.g., at least 85%, 88%, 90%, 91%, 92%, 93%, 94%, 95%, 96%, 97%, 98%, 99%) sequence identity to that (or those) listed in Table 2, and in the meantime retain the binding affinity to CD19 at a level similar to or even higher than its parental antibody.

In certain embodiments, the anti-CD19 antibodies and antigen-binding fragments thereof comprise one or more variable region sequences having at least 80% (e.g., at least 85%, 88%, 90%, 91%, 92%, 93%, 94%, 95%, 96%, 97%, 98%, 99%) sequence identity to that (or those) listed in SEQ ID NO: 94, SEQ ID NO: 98, SEQ ID NO: 102, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 122, SEQ ID NO: 124, SEQ ID NO: 128, SEQ ID NO: 132, SEQ ID NO: 96, SEQ ID NO: 100, SEQ ID NO: 104, SEQ ID NO: 120, SEQ ID NO: 126, SEQ ID NO: 130, SEQ ID NO: 134 and in the meantime retain the binding affinity to CD19 at a level similar to or even higher than its parent antibody. In some embodiments, a total of 1 to 10 amino acids have been substituted, inserted, or deleted in a sequence selected from SEQ ID NO: 94, SEQ ID NO: 98, SEQ ID NO: 102, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 122, SEQ ID NO: 124, SEQ ID NO: 128, SEQ ID NO: 132, SEQ ID NO: 96, SEQ ID NO: 100, SEQ ID NO: 104, SEQ ID NO: 120, SEQ ID NO: 126, SEQ ID NO: 130, and SEQ ID NO: 134. In some embodiments, the substitutions, insertions, or deletions occur in regions outside the CDRs (i.e., in the FRs).

Glycosylation Variant

The anti-CD19 antibodies and antigen-binding fragments provided herein also encompass a glycosylation variant, which can be obtained to either increase or decrease the extent of glycosylation of the antibody or antigen binding fragment.

The anti-CD19 antibody or antigen binding fragment thereof may comprise one or more amino acid residues with a side chain to which a carbohydrate moiety (e.g., an oligosaccharide structure) can be attached. Glycosylation of antibodies is typically either N-linked or O-linked. N-linked refers to the attachment of the carbohydrate moiety to the side chain of an asparagine residue, for example, an asparagine residue in a tripeptide sequence such as asparagine-X-serine and asparagine-X-threonine, where X is any amino acid except proline. O-linked glycosylation refers to the attachment of one of the sugars N-aceylgalactosamine, galactose, or xylose to a hydroxyamino acid, most commonly to serine or threonine. Removal of a native glycosylation site can be conveniently accomplished, for example, by altering the amino acid sequence such that one of the above-described tripeptide sequences (for N-linked glycosylation sites) or serine or threonine residues (for O-linked glycosylation sites) present in the sequence is substituted. A new glycosylation site can be created in a similar way by introducing such a tripeptide sequence or serine or threonine residue.

Cysteine-Engineered Variant

The anti-CD19 antibodies and antigen-binding fragments provided herein also encompass a cysteine-engineered variant, which comprises one or more introduced free cysteine amino acid residues.

A free cysteine residue is one which is not part of a disulfide bridge. A cysteine-engineered variant is useful for conjugation with, for example a cytotoxic and/or imaging compound, a label, or a radioisotype among others, at the site of the engineered cysteine, through for example a maleimide or haloacetyl. Methods for engineering antibodies or antigen-binding fragments to introduce free cysteine residues are known in the art, see, for example, WO2006/034488.

Fc Variant

The anti-CD19 antibodies and antigen-binding fragments provided herein also encompass an Fc variant, which comprises one or more amino acid residue modifications or substitutions at its Fc region and/or hinge region.

In certain embodiments, the anti-CD19 antibodies or antigen-binding fragments comprise one or more amino acid substitution(s) that improves pH-dependent binding to neonatal Fc receptor (FcRn). Such a variant can have an extended pharmacokinetic half-life, as it binds to FcRn at acidic pH which allows it to escape from degradation in the lysosome and then be translocated and released out of the cell. Methods of engineering an antibody and antigen-binding fragment thereof to improve binding affinity with FcRn are well-known in the art, see, for example, Vaughn, D. et al, Structure, 6(1): 63-73, 1998; Kontermann, R. et al, Antibody Engineering, Volume 1, Chapter 27: Engineering of the Fc region for improved PK, published by Springer, 2010; Yeung, Y. et al, Cancer Research, 70: 3269-3277 (2010); and Hinton, P. et al, J. Immunology, 176:346-356 (2006).

In certain embodiments, the anti-CD19 antibodies or antigen-binding fragments comprise one or more amino acid substitution(s) that alters the antibody-dependent cellular cytotoxicity (ADCC). Certain amino acid residues at CH2 domain of the Fc region can be substituted to provide for enhanced ADCC activity. Alternatively or additionally, carbohydrate structures on the antibody can be changed to enhance ADCC activity. Methods of altering ADCC activity by antibody engineering have been described in the art, see for example, Shields R L. et al., J Biol Chem. 2001. 276(9): 6591-604; Idusogie E E. et al., J Immunol. 2000. 164(8): 4178-84; Steurer W. et al., J Immunol. 1995, 155(3): 1165-74; Idusogie E E. et al., J Immunol. 2001, 166(4): 2571-5; Lazar G A. et al., PNAS, 2006, 103(11): 4005-4010; Ryan M C. et al., Mol. Cancer Ther., 2007, 6: 3009-3018; Richards J O, et al., Mol Cancer Ther. 2008, 7(8): 2517-27; Shields R. L. et al, J. Biol. Chem, 2002, 277: 26733-26740; Shinkawa T. et al, J. Biol. Chem, 2003, 278: 3466-3473.

In certain embodiments, the anti-CD19 antibodies or antigen-binding fragments comprise one or more amino acid substitution(s) that alters Complement Dependent Cytotoxicity (CDC), for example, by improving or diminishing C1q binding and/or Complement Dependent Cytotoxicity (CDC) (see, for example, WO99/51642; Duncan & Winter Nature 322:738-40 (1988); U.S. Pat. Nos. 5,648,260; 5,624,821; and WO94/29351 concerning other examples of Fc region variants.

In certain embodiments, the anti-CD19 antibodies or antigen-binding fragments comprise one or more amino acid substitution(s) in the interface of the Fc region to facilitate and/or promote heterodimerization. These modifications comprise introduction of a protuberance into a first Fc polypeptide and a cavity into a second Fc polypeptide, wherein the protuberance can be positioned in the cavity so as to promote interaction of the first and second Fc polypeptides to form a heterodimer or a complex. Methods of generating antibodies with these modifications are known in the art, e.g., as described in U.S. Pat. No. 5,731,168.

Antigen-Binding Fragments

Provided herein are also anti-CD19 antigen-binding fragments. Various types of antigen-binding fragments are known in the art and can be developed based on the anti-CD19 antibodies provided herein, including for example, the exemplary antibodies whose CDR and FR sequences are shown in Tables 1 and 2, and their different variants (such as affinity variants, glycosylation variants, Fc variants, cysteine-engineered variants and so on).

In certain embodiments, an anti-CD19 antigen-binding fragment provided herein is a camelized single domain antibody, a diabody, a single chain Fv fragment (scFv), an scFv dimer, a BsFv, a dsFv, a $(dsFv)_2$, a dsFv-dsFv', an Fv fragment, a Fab, a Fab', a $F(ab')_2$, a bispecific antibody, a ds diabody, a nanobody, a domain antibody, a single domain antibody, or a bivalent domain antibody.

Various techniques can be used for the production of such antigen-binding fragments. Illustrative methods include, enzymatic digestion of intact antibodies (see, e.g., Morimoto et al., Journal of Biochemical and Biophysical Methods 24:107-117 (1992); and Brennan et al., Science, 229:81 (1985)), recombinant expression by host cells such as *E. Coli* (e.g., for Fab, Fv and ScFv antibody fragments), screening from a phage display library as discussed above (e.g., for ScFv), and chemical coupling of two Fab'-SH fragments to form $F(ab')_2$ fragments (Carter et al., Bio/Technology 10:163-167 (1992)). Other techniques for the production of antibody fragments will be apparent to a skilled practitioner.

In certain embodiments, the antigen-binding fragment is a scFv. Generation of scFv is described in, for example, WO 93/16185; U.S. Pat. Nos. 5,571,894; and 5,587,458. scFv may be fused to an effector protein at either the amino or the carboxy terminus to provide for a fusion protein (see, for example, Antibody Engineering, ed. Borrebaeck).

The anti-CD19 antibodies or antigen-binding fragments thereof provided herein can be a monoclonal antibody, polyclonal antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals.

In certain embodiments, the antibodies and antigen-binding fragments thereof can be used as the base of bispecific or multivalent antibodies, or antibody-drug conjugates.

Bispecific Antibodies, Multivalent Antibodies

In certain embodiments, the antibodies and antigen-binding fragments thereof provided herein are bivalent, tetravalent, hexavalent, or multivalent. In certain embodiments, the antibodies and antigen-binding fragments thereof provided herein are monospecific, or bispecific.

The term "valent" as used herein refers to the presence of a specified number of antigen binding sites in a given molecule. As such, the terms "bivalent", "tetravalent", and "hexavalent" denote the presence of two binding site, four binding sites, and six binding sites, respectively, in an antigen-binding molecule. A bivalent molecule can be monospecific if the two binding sites are both for specific binding of the same antigen or the same epitope. Similarly, a trivalent molecule can be bispecific, for example, when two binding sites are monospecific for a first antigen (or epitope) and the third binding site is specific for a second antigen (or epitope).

In certain embodiments, the antibodies and antigen-binding fragments thereof provided herein can be monospecific but bivalent, trivalent, or tetravalent, with at least two binding sites specific for the same antigen or epitope. This, in certain embodiments, provides for stronger binding to the antigen or the epitope than a monovalent counterpart. In certain embodiments, in a bivalent antigen-binding moiety, the first valent of binding site and the second valent of binding site are structurally identical (i.e. having the same sequences), or structurally different (i.e. having different sequences albeit with the same specificity).

In certain embodiments, the antibodies and antigen-binding fragments thereof provided herein are bispecific. In some embodiments, the bispecific antibodies and antigen-binding fragments thereof provided herein has a first specificity for CD19, and a second specificity. In some embodiments, the second specificity is for CD19 but to different epitopes. In some embodiments, the second specificity is for a second antigen different from CD19 and is capable of promoting or facilitating immune response to the CD19-expressing target cells when they are in close proximity. For example, the bispecific antibody may bring CD19-expressing target cells in close proximity to an immune cell such as a T cell or NK cell, hence promoting recognition or elimination of such a target cell by the immune system.

The bispecific antibodies and antigen-binding fragments provided herein can be made with any suitable methods known in the art. In a conventional approach, two immunoglobulin heavy chain-light chain pairs having different antigenic specificities can be co-expressed in a host cell to produce bispecific antibodies in a recombinant way (see, for example, Milstein and Cuello, Nature, 305: 537 (1983)), followed by purification by affinity chromatography.

Recombinant approach may also be used, where sequences encoding the antibody heavy chain variable domains for the two specificities are respectively fused to immunoglobulin constant domain sequences, followed by insertion to an expression vector which is co-transfected with an expression vector for the light chain sequences to a suitable host cell for recombinant expression of the bispecific antibody (see, for example, WO 94/04690; Suresh et al., Methods in Enzymology, 121:210 (1986)). Similarly, scFv dimers can also be recombinantly constructed and expressed from a host cell (see, e.g., Gruber et al., J. Immunol., 152:5368 (1994).)

In another method, leucine zipper peptides from the Fos and Jun proteins can be linked to the Fab' portions of two different antibodies by gene fusion. The linked antibodies are reduced at the hinge region to four half antibodies (i.e. monomers) and then re-oxidized to form heterodimers (Kostelny et al., J. Immunol., 148(5):1547-1553 (1992)).

The two antigen-binding domains may also be conjugated or cross-linked to form a bispecific antibody or antigen-binding fragment. For example, one antibody can be coupled to biotin while the other antibody to avidin, and the strong association between biotin and avidin would complex the two antibodies together to form a bispecific antibody (see, for example, U.S. Pat. No. 4,676,980; WO 91/00360, WO 92/00373, and EP 03089). For another example, the two antibodies or antigen-binding fragments can be cross-linked by conventional methods known in the art, for example, as disclosed in U.S. Pat. No. 4,676,980.

Bispecific antigen-binding fragments may be generated from a bispecific antibody, for example, by proteolytic cleavage, or by chemical linking. For example, an antigen-binding fragment (e.g., Fab') of an antibody may be prepared and converted to Fab'-thiol derivative and then mixed and reacted with another converted Fab' derivative having a different antigenic specificity to form a bispecific antigen-binding fragment (see, for example, Brennan et al., Science, 229: 81 (1985)).

In certain embodiments, the bispecific antibody or antigen-binding fragments may be engineered at the interface so that a knob-into-hole association can be formed to promote heterodimerization of the two different antigen-binding sites. "Knob-into-hole" as used herein, refers to an interaction between two polypeptides (such as Fc), where one polypeptide has a protuberance (i.e. "knob") due to presence of an amino acid residue having a bulky side chain (e.g., tyrosine or tryptophan), and the other polypeptide has a cavity (i.e. "hole") where a small side chain amino acid residue resides (e.g., alanine or threonine), and the protuberance is positionable in the cavity so as to promote interaction of the two polypeptides to form a heterodimer or a complex. Methods of generating polypeptides with knobs-into-holes are known in the art, e.g., as described in U.S. Pat. No. 5,731,168.

Conjugates

In some embodiments, the anti-CD19 antibodies and antigen-binding fragments thereof are linked to a conjugate. A conjugate is a non-proteinaceous moiety that can be attached to the antibody or antigen-binding fragment thereof. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies or antigen binding fragments thereof are linked to one or more conjugates via a linker. In certain embodiments, the linker is a hydrazone linker, a disulfide linker, a bifunctional linker, dipeptide linker, glucuronide linker, a thioether linker.

In certain embodiments, the anti-CD19 antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate.

The conjugate can be a therapeutic agent (e.g., a chemotherapeutic agent), a radioactive isotope, a detectable label (e.g., a lanthanide, a luminescent label, a fluorescent label, or an enzyme-substrate label), a pharmacokinetic modifying moiety, or a purifying moiety (such as a magnetic bead or nanoparticle).

Examples of detectable label may include a fluorescent labels (e.g., fluorescein, rhodamine, dansyl, phycoerythrin, or Texas Red), enzyme-substrate labels (e.g., horseradish peroxidase, alkaline phosphatase, luceriferases, glucoamylase, lysozyme, saccharide oxidases or β-D-galactosidase), radioisotuopes, other lanthanides, luminescent labels, chromophoric moiety, digoxigenin, biotin/avidin, a DNA molecule or gold for detection.

Examples of radioisotopes may include $^{123}I$, $^{124}I$, $^{125}I$, $^{131}I$, $^{35}S$, $^{3}H$, $^{111}In$, $^{112}In$, $^{14}C$, $^{64}Cu$, $^{67}Cu$, $^{86}Y$, $^{88}Y$, $^{90}Y$, $^{177}Lu$, $^{211}At$, $^{186}Re$, $^{188}Re$, $^{153}Sm$, $^{212}Bi$, and $^{32}P$. Radioisotope labelled antibodies are useful in receptor targeted imaging experiments.

In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like.

In certain embodiments, the conjugate can be a purification moiety such as a magnetic bead or a nanoparticle.

Antibody-Drug Conjugates

In certain embodiments, the present disclosure provides antibody-drug conjugates (ADC) comprising any of the above anti-CD19 antibodies or antigen-binding fragments conjugated to a cytotoxic agent such as a chemotherapeutic agent, a drug, a growth inhibitory agent, toxin, or a radioactive isotope (i.e., a radioconjugate).

Antibody-drug conjugates can be useful for local delivery of cytotoxic agents, for example, in the treatment of cancer. This allows for targeted delivery of cytotoxic agents to tumors and intracellular accumulation therein, which is particularly useful where systemic administration of these unconjugated cytotoxic agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed. s), pp. 475-506; Syrigos and Epenetos (1999) Anticancer Research 19:605-614; Niculescu-Duvaz and Springer (1997) Adv. Drg Del. Rev. 26:151-172; U.S. Pat. No. 4,975,278).

In certain embodiments, the cytotoxic agent can be any agent that is detrimental to cells or that can damage or kill cells. In certain embodiments, the cytotoxic agent is optionally a cytotoxin, a DNA-alkylators, a topoisomerase inhibitor, a tubulin-Binders, or other anticancer drugs.

Examples of enzymatically active cytotoxin include bacterial toxins and plant toxins, such as for example, diphtheria toxin, exotoxin A chain (from *Pseudomonas aeruginosa*), ricin, abrin, modeccin, alpha-sarcin, *Aleurites fordii*. proteins, dianthin proteins, *Phytolaca americana* proteins (PART, PAPII, and PAP-S), *Momordica charantia* inhibitor, curcin, crotin, *Sapaonaria officinalis* inhibitor, gelonin, restrictocin, phenomycin, enomycin, and the tricothecenes (see, e.g., WO 93/21232). Such a large molecule toxin can be conjugated to the antibodies or antigen-binding fragments provided herein using methods known in the art, for example, as described in Vitetta et al (1987) Science, 238: 1098.

The cytotoxic agent can also be small molecule toxins and drugs, such as geldanamycin (Mandler et al (2000) Jour. of the Nat. Cancer Inst. 92(19):1573-1581; Mandler et al (2002) Bioconjugate Chem. 13:786-791), maytansinoids (EP 1391213; Liu et al., (1996) Proc. Natl. Acad. Sci. USA 93:8618-8623), calicheam icin (Lode et al (1998) Cancer Res. 58:2928; Hinman et al (1993) Cancer Res. 53:3336-3342), taxol, cytochalasin B, gramicidin D, ethidium bromide, emetine, mitomycin, etoposide, tenoposide, vincristine, vinblastine, vindesine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine), calicheamicin, maytansinoids, dolastatins, auristatins, a trichothecene, and CC1065, and the derivatives thereof having cytotoxic activity.

The cytotoxic agent can also be a highly radioactive isotope. Examples include $At^{211}$, $I^{131}$, $I^{125}$, $Y^{90}$, $Re^{186}$, $Sm^{153}$, $Bi^{212}$, $P^{32}$, $Pb^{212}$ and radioactive isotopes of Lu. Methods of conjugation of a radioisotope to an antibody is known in the art, for example, via a suitable ligand reagent (see, e.g., WO94/11026; Current Protocols in Immunology, Volumes 1 and 2, Coligen et al, Ed. Wiley-Interscience, New York, N.Y., Pubs. (1991)). A ligand reagent has a chelating ligand that can bind, chelate or otherwise complex a radioisotope metal, and also has a functional group that is reactive with a thiol of cysteine of an antibody or antigen-binding fragment. Exemplary chelating ligands include DOTA, DOTP, DOTMA, DTPA and TETA (Macrocyclics, Dallas, Tex.).

The conjugates provided herein of antibodies (or antigen-binding fragments) and cytotoxic agents may be made using a variety of bifunctional protein linking agents. Exemplary bifunctional linking reagents include, such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluom-2,4-dinitrobenzene).

In certain embodiments, the ADC provided herein is prepared with a linker reagents selected from the group consisting of: BMPS, EMCS, GMBS, HBVS, LC-SMCC, MBS, MPRH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSG (succinimidyl-(4-vinylsulfone)benzoate). Those linker reagents are commercially available (e.g., from Pierce Biotechnology, Inc., Rockford, Ill., U.S.A, see pages 467-498, 2003-2004 Applications Handbook and Catalog).

In certain embodiments, the linker is cleavable under a particular physiological environment, thereby facilitating release of the cytotoxic drug in the cell. For example, the linker can be an acid-labile linker, peptidase-sensitive linker, photolabile linker, dimethyl linker or disulfide-containing linker (Chari et al., Cancer Research 52:127-131 (1992); U.S. Pat. No. 5,208,020). In some embodiments, the linker may comprise amino acid residues, such as a dipeptide, a tripeptide, a tetrapeptide or a pentapeptide. The amino acid residues in the linker may be natural or non-naturally occurring amino acid residues. Examples of such linkers include: valine-citrulline (ve or val-cit), alanine-phenylalanine (af or ala-phe), glycine-valine-citrulline (gly-yal-cit), glycine-glycine-glycine (gly-gly-gly), an valine-citrullin-p-aminobenzyloxycaronyl ("vc-PAB"). Amino acid linker components can be designed and optimized in their selectivity for enzymatic cleavage by a particular enzymes, for example, a tumor-associated protease, cathepsin B, C and D, or a plasmin protease.

In certain embodiments, in the ADC provided herein, an antibody (or antigen-binding fragment) is conjugated to one or more cytotoxic agents at an antibody: agent ratio of about 1 to about 20, about 1 to about 6, about 2 to about 6, about 3 to about 6, about 2 to about 5, about 2 to about 4, or about 3 to about 4.

The ADC provided herein may be prepared by any suitable methods known in the art. In certain embodiments, a nucleophilic group of the antibody (or antigen-binding fragment) is first reacted with a bifunctional linker reagent and then linked to the cytotoxic agent, or the other way around, i.e., first reacting a nucleophilic of the cytotoxic agent with a bifunctional linker and then linking to the antibody.

In certain embodiments, the cytotoxic agent may contain (or modified to contain) a thiol reactive functional group which may react with a cysteine thiol of a free cysteine of the antibodies or antigen-binding fragments provided herein. Exemplary thiol-reactive functional group include, for example, a maleimide, an iodoacetamide, a pyridyl disulfide, haloacetyl, succinimidyl ester (e.g., NHS, N-hydroxysuccinimide), isothiocyanate, sulfonyl chloride, 2,6-dichlorotriazinyl, pentafluorophenyl ester, or phosphoramidite (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

The cytotoxic agent or the antibody may react with a linking reagent before being conjugated to form the ADC. For example, N-hydroxysuccinimidyl ester (NETS) of a cytotoxic agent may be preformed, isolated, purified, and/or characterized, or it may be formed in situ and reacted with a nucleophilic group of an antibody. Typically, the carboxyl form of the conjugate is activated by reacting with some combination of a carbodiimide reagent, e.g., dicyclohexyl-carbodiimide; diisopropyl carbodiimide, or a uronium reagent, e.g., TsTu (O—(N-Succinimidyl)-N,N,N',N'-tetramethyluronium tetrafluoroborate, HBTU (O-benzotri-azol-1-yl)-N,N,N'N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester. In some cases, the cytotoxic agent and the antibody may be linked by in situ activation and reaction to form the ADC in one step. Other activating and linking reagents include TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), PyBOP (benzotriazole-1-yl-oxy-trispyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbo-diimide), MSNT (1-(mesitylene-2-sulfonyl)-3-nitro-1H-1,2,4-triazole, and aryl sulfonyl halides, e.g., triisopropylbenzenesulfonyl chloride. In another example, the antibody or antigen-binding fragments may be conjugated to biotin, then indirectly conjugated to a second conjugate that is conjugated to avidin.

Maytansine and Maytansinoids

In one embodiment, any of the anti-CD19 antibodies or antigen-binding fragments provided herein is conjugated to one or more maytansinoid molecules. Maytansinoids are mitototic inhibitors which act by inhibiting tubulin polymerization.

Maytansine compounds (such as maytansinol and C-3 maytansinol esters) suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods (see, e.g., U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533).

Suitable maytansinoids are disclosed, for example, in U.S. Pat. No. 5,208,020 and in the other patents and nonpatent publications referred to herein. Exemplary maytansinoids are maytansinol and maytansinol analogues modified in the aromatic ring or at other positions of the maytansinol molecule, see, e.g., C-49-dechloro (U.S. Pat. No. 4,256, 746); C-20-hydroxy (or C-20-demethyl)+/−C-19-dechloro (U.S. Pat. Nos. 4,361,650 and 4,307,016); C-20-demethoxy, C-20-acyloxy (—OCOR), +/−dechloro (U.S. Pat. No. 4,294, 757), C-9-SH (U.S. Pat. No. 4,424,219); C-14-alkoxymethyl (demethoxy/CH$_2$OR)(U.S. Pat. No. 4,331,598); C-14-hydroxymethyl or acyloxymethyl (CH$_2$OH or CH$_2$OAc) (U.S. Pat. No. 4,450,254); C-15-hydroxy/acyloxy (U.S. Pat. No. 4,364,866); C-15-methoxy (U.S. Pat. Nos. 4,313,946 and 4,315,929); C-18-N-demethyl (U.S. Pat. Nos. 4,362,663 and 4,322,348); and 4,5-deoxy (U.S. Pat. No. 4,371,533). In certain embodiments, the maytansinoid conjugated to the antibodies provided herein is DM1 (N2'-deacetyl-N2'-(3-mercapto-1-oxopropyl)-Maytansine), or DM4 (N2'-deacetyl-N2'-(4-mercapto-4-methyl-1-oxopentyl)-6-methyl-maytansine).

Anti-CD19 antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In certain embodiments, an average of 1 to 4, 2 to 4, or 3 to 4 maytansinoid molecules is conjugated per antibody molecule without negatively affecting the function or solubility of the antibody.

A maytansinoid moiety can be linked to an antibody or antigen-binding fragment via any suitable linkers known in the art, see, for example, in U.S. Pat. Nos. 5,208,020, 6,441,163, or EP Patent 0 425 235 B1, Chari et al., Cancer Research 52:127-131 (1992), and US 2005/0169933 A1, the disclosures of which are hereby expressly incorporated by reference. The linkers in the ADC provided herein include disulfide groups, thioether groups, acid labile groups, photolabile groups, peptidase labile groups, or esterase labile groups. In certain embodiments, the linker in the ADC provided herein is a bifunctional protein coupling agent, such as N-succinimidyl-3-(2-pyridyldithio) propionate (SPDP), succinimidyl-4-(N-maleimidomethyl) cyclohexane-1-carboxylate (SMCC), N-succinimidyl-4-(2-pyridylthio)pentanoate (SPP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene).

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolostatins

In one embodiment, any of the anti-CD19 antibodies or antigen-binding fragments provided herein is conjugated to one or more dolostatins, dolostatin peptidic analogs and derivative, or auristatins (U.S. Pat. Nos. 5,635,483; 5,780,588). Dolastatins and auristatins have anticancer and antifungal activity, presumably by interference with microtubule dynamics, GTP hydrolysis, and nuclear and cellular division (see, e.g., U.S. Pat. No. 5,663,149; Pettit et al (1998) Antimicrob. Agents Chemother. 42:2961-2965; Woyke et al (2001) Antimicrob. Agents and Chemother. 45(12):3580-3584).

Exemplary auristatins include MMAE and MMAF. The auristatin/dolastatin drug moieties may be prepared according to the methods of: US 2005/0238649; U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

The dolastatin or auristatin drug moiety may be attached to the antibody through the N (amino) terminus or the C (carboxyl) terminus of the peptidic drug moiety (WO 02/088172).

Chimeric Antigen Receptor (CAR) Composition

The present disclosure also provides chimeric antigen receptors (CARs) comprising antigen binding fragment of the antibody provided herein that binds specifically to CD19 and a T-cell activation moiety. In some embodiment, the T-cell activation moiety comprises a native T-cell activation moiety of a TCR. In some embodiment, the T-cell activation moiety comprises a transmembrane domain and an intracellular signaling domain of a TCR.

Antigen Binding Fragment

In some embodiment, the antigen binding fragment can be any fragment that binds to CD19 including but not limited to antigen recognition domains derived from any one or more of the antibodies provided herein. In some embodiments, it is beneficial for the antigen binding fragment to be derived from the same species in which the CAR will ultimately be used in. For example, for use in humans, it may be beneficial to have the antigen binding fragment used in the CAR derived from a human antibody or a humanized antibody. In some embodiment, the antigen binding fragment is a single chain variable fragment (scFv). In some embodiment, the antigen binding fragment may exist in a variety of other forms including, for example, Fv, Fab, and (Fab')$_2$, as well as bi-functional (i.e. bi-specific) hybrid antibody fragments (e.g., Lanzavecchia et al., Eur. J. Immunol. 17, 105 (1987)).

Transmembrane Domain

With respect to the transmembrane domain, in various embodiments, the CAR is designed to comprise a transmembrane domain that is fused to the extracellular domain of the CAR. In one embodiment, the transmembrane domain that is naturally associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the CAR. A glycine-serine doublet provides a particularly suitable linker.

Signal Transduction Domain

The signal transduction domain of the CAR of the present disclosure is responsible for activation of at least one of the normal TCR effector functions of the T cell in which the CAR has been placed in. TCR effector function of a T cell, for example, may be cytolytic activity or helper activity including the secretion of cytokines. Thus the term "signal transduction domain" refers to the portion of a protein which transduces the TCR effector function signal and directs the T cell to perform a specialized function. While usually the entire intracellular signal transduction domain can be employed, in many cases it is not necessary to use the entire chain. To the extent that a truncated portion of the intracellular signal transduction domain is used, such truncated portion may be used in place of the intact chain as long as it transduces the effector function signal. The term intracellular signaling domain is thus meant to include any truncated portion of the intracellular signal transduction domain sufficient to transduce the TCR effector function signal.

Examples of intracellular signaling domains for use in the CAR of the present disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary intracellular signal transduction sequences regulate primary activation of the TCR complex either in a stimulatory way, or in an inhibitory way. Primary intracellular signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the intracellular signallingc domain of the CAR is designed to comprise the CD3-zeta signaling domain by itself or combined with any other desired cytoplasmic domain(s) useful in the context of the CAR of the present disclosure. For example, the intracellular signaling domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. The CD3 zeta chain portion and the costimulatory signaling region may be linked to each other in a random or in a specified order. Optionally, a short oligo- or polypeptide linker, for example, between 2 and 10 amino acids in length may form the linkage. A glycine-serine doublet provides a particularly suitable linker.

In one aspect, the present disclosure further provides nucleic acid sequences encoding the CAR provided herein, comprising a first polynucleotide sequence encoding an antigen binding fragment of the antibodies provided herein, and optionally a second polynucleotide sequence encoding a transmembrane domain and an intracellular signal transduction domain of TCR. In some embodiments, the sequence encoding the antigen binding fragment is operably linked to the sequence encoding the transmembrane domain and the signal transduction domain of TCR. In some embodiment, the signal transduction comprises, a costimulatory signaling region and/or a CD3 zeta chain portion. The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

In one aspect, the present disclosure provides vectors comprising the nucleic acid sequence encoding the CAR provided herein. In some embodiments, the vector is retroviral and lentiviral vector construct expressing the CAR of the present disclosure which can be directly transduced into a cell, or RNA construct that can be directly transfected into a cell.

In one aspect, the present disclosure provides isolated host cells which express the CAR provided herein.

In one aspect, the present disclosure further provides methods for stimulating a T cell-mediated immune response to a CD19-expressing target in a subject, the method comprising administering to the subject an effective amount of the T cell expressing the CAR provided herein.

Polynucleotides and Recombinant Methods

The present disclosure provides isolated polynucleotides that encode the anti-CD19 antibodies and antigen-binding fragments thereof. In certain embodiments, the isolated polynucleotides comprise one or more nucleotide sequences as shown in SEQ IN NO: 95, 97, 99, 101, 103, 105, 107, 109, 111, 113, 115, 117, 119, 121, 123, 125, 127, 129, 131, 133 and/or 135, which encodes the variable region of the exemplary antibodies. DNA encoding the monoclonal antibody is readily isolated and sequenced using conventional procedures (e.g., by using oligonucleotide probes that are capable of binding specifically to genes encoding the heavy and light chains of the antibody). The encoding DNA may also be obtained by synthetic methods.

The isolated polynucleotide that encodes the anti-CD9 antibodies and antigen-binding fragments thereof (e.g., including the sequences in as shown in SEQ IN NO: 95, 97, 99, 101, 103, 105, 107, 109, 111, 113, 115, 117, 119, 121, 123, 125, 127, 129, 131, 133 and/or 135) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g., SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMD18-T, pMONO, pSELECT, pUNO, pDUO, Psg5L, pBABE, pWPXL, pBI, p15TV-L, pPro18, pTD, pRS420, pLexA, pACT2.2 etc, and other laboratorial and commercially available vectors. Suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-CD19 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus*

(ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-CD19 antibody production and cultured in conventional nutrient media modified as appropriate for inducing promoters, selecting transformants, or amplifying the genes encoding the desired sequences. In another embodiment, the antibody may be produced by homologous recombination known in the art.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The anti-CD19 antibodies or antigen-binding fragments thereof prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

In certain embodiments, Protein A immobilized on a solid phase is used for immunoaffinity purification of the antibody and antigen-binding fragment thereof. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (Lindmark et al., J. Immunol. Meth. 62:1-13 (1983)). Protein G is recommended for all mouse isotypes and for human gamma3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX.™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Composition

The present disclosure further provides pharmaceutical compositions comprising the anti-CD19 antibodies or antigen-binding fragments thereof or the antibody-drug conjugate provided herein, and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylceluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In certain embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-CD19 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Methods of Use

The present disclosure also provides therapeutic methods comprising: administering a therapeutically effective amount of the antibody or antigen-binding fragment as provided herein to a subject in need thereof, thereby treating or preventing a CD19-related condition or a disorder. In some embodiment, the CD19-related condition or a disorder is cancer. In some embodiments, the cancer is selected from the group consisting of B cell lymphoma, optionally Hodgkin lymphoma or non-Hodgkin lymphoma, wherein the non-Hodgkin lymphoma comprises: Diffuse large B-cell lymphoma (DLBCL), Follicular lymphoma, Marginal zone B-cell lymphoma (MZL), Mucosa-Associated Lymphatic Tissue lymphoma (MALT), Small lymphocytic lymphoma (chronic lymphocytic leukemia, CLL), or Mantle cell lymphoma (MCL), Acute Lymphoblastic Leukemia (ALL), or Waldenstrom's Macroglobulinemia (WM). In some embodiment, the subject is human.

In another aspect, methods are provided to treat a condition in a subject that would benefit from modulation of CD19 of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements.

In certain embodiments, an anti-CD19 antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 3 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 3 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The anti-CD19 antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

In some embodiments, the anti-CD19 antibodies or antigen-binding fragments disclosed herein may be administered alone or in combination with one or more additional therapeutic means or agents. For example, the antibodies or antigen-binding fragments disclosed herein may be administered in combination with another therapeutic agent, for example, a chemotherapeutic agent or an anti-cancer drug.

In certain of these embodiments, an anti-CD19 antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an anti-CD19antibody or antigen-binding fragment administered "in combination" with another therapeutic agent does not have to be administered simultaneously with or in the same composition as the agent. An anti-CD19antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

The present disclosure further provides methods of using the anti-CD19 antibodies or antigen-binding fragments thereof. In some embodiments, the present disclosure provides methods of inhibiting growth of CD19-expressing cells in vivo or in vitro, comprising: contacting the CD19-expressing cells with the antibody or antigen-binding fragment thereof provided herein. In some embodiments, the present disclosure provides methods of modulating CD19 activity in a CD19-expressing cell, comprising exposing the CD19-expressing cell to the antibody or antigen-binding fragment thereof provided herein.

In some embodiments, the present disclosure provides methods of detecting presence or amount of CD19 in a sample, comprising contacting the sample with the antibody or antigen-binding fragment thereof, and determining the presence or the amount of CD19 in the sample.

In some embodiments, the present disclosure provides methods of diagnosing a CD19 related disease or condition in a subject, comprising: a) obtaining a sample from the subject; b) contacting the sample with the antibody or antigen-binding fragment thereof provided herein; c) determining presence or amount of CD19 in the sample; and d) determining existence of the CD19 related disease or condition in the subject.

In some embodiments, the present disclosure provides kits comprising the antibody or antigen-binding fragment thereof provided herein, optionally conjugated with a detectable moiety. The kits may be useful in detection of CD19 or diagnosis of CD19 related disease.

In some embodiments, the present disclosure also provides use of the antibody or antigen-binding fragment thereof provided herein in the manufacture of a medicament for treating a CD19 related disease or condition in a subject, in the manufacture of a diagnostic reagent for diagnosing a CD3 related disease or condition.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Material Generation 1.1 Reference Antibody Generation

Variable region gene of anti-CD19 reference antibodies (WBP701-BMK1 corresponds to huB4 in patent US20140072587A1; WBP701-BMK2 corresponds to hBU12 in U.S. Pat. No. 8,242,252B2; WBP701-BMK3 corresponds to 21D4 in U.S. Pat. No. 8,097,703B2) were cloned into an expression vector containing human Fc region gene. The expression plasmids were transfected into Expi293 cells (Invitrogen-A14527) using Expi-Fectamine293 Transfection Kit (Invitrogen-A14524). The cells were cultured in Expi293 expression medium (Invitrogen-A1435101) on an orbital shaker platform rotating at 135 rpm, in a 37° C. incubator. The harvested supernatant was purified using Protein A column (GE Healthcare 17543802).

Figure 2:
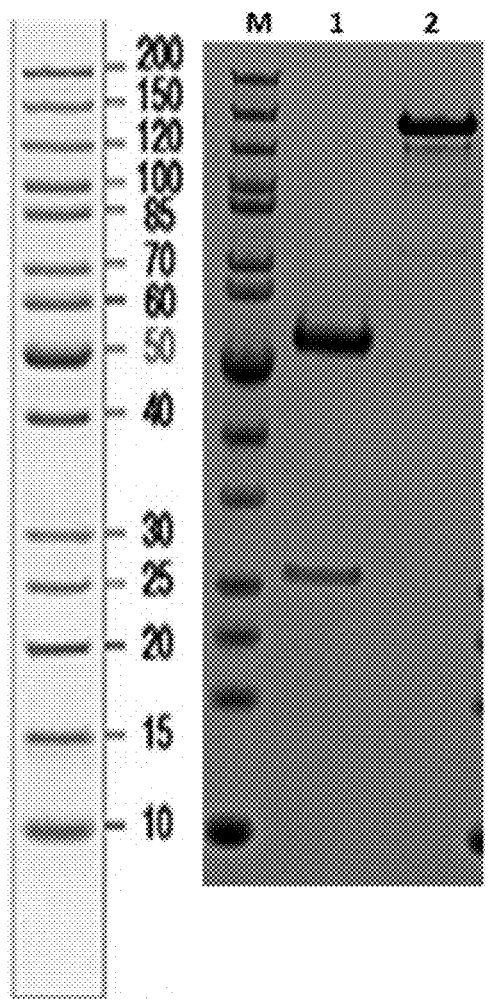
FIG. 2 shows SDS-PAGE of WBP701-BMK3. M: Protein marker; Lane1: BMK3, reduced; Lane2: BMK3, non-reduced.
Figure 3A:
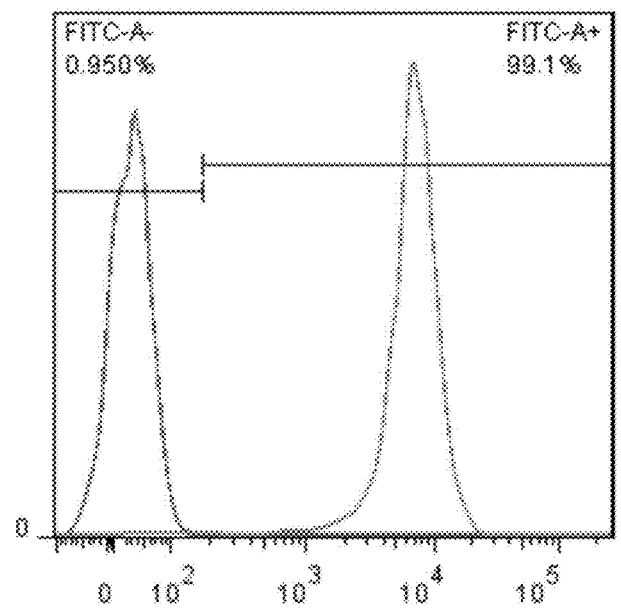
FIG. 3A shows flow cytometry histograms for the CD19 expression in the human CD19 transfected 293F cell line (WBP701.293F.hPro1.FL.A2). The peak on the left represents negative control signal. The right-shifted peak represents the CD19 expression in the detected cell line.
Figure 3B:
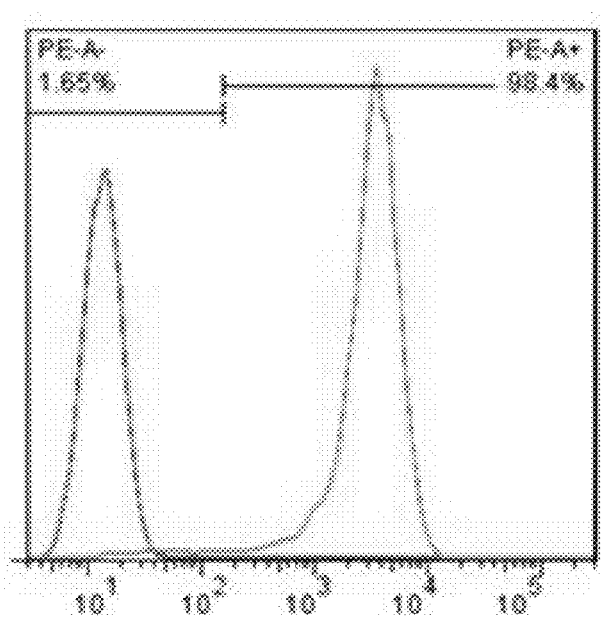
FIG. 3B shows flow cytometry histograms for the CD19expression in the human CD19 transfected CHO-K1 cell line (WBP701.CHO-K1.hPro1.FL.B4). The peak on the left represents negative control signal. The right-shifted peak represents the CD19 expression in the detected cell line.
Figure 3C:
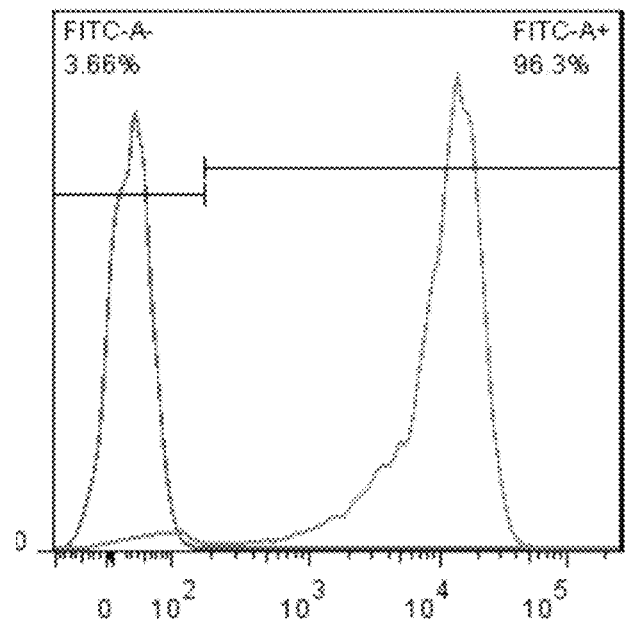
FIG. 3C shows flow cytometry histograms for the CD19 expression in the cynomolgus monkey CD19 transfected 293 cell line (WBP701.293F.cpro1.FL.C1). The peak on the left represents negative control signal. The right-shifted peak represents the CD19 expression in the detected cell line.
Figure 3D:
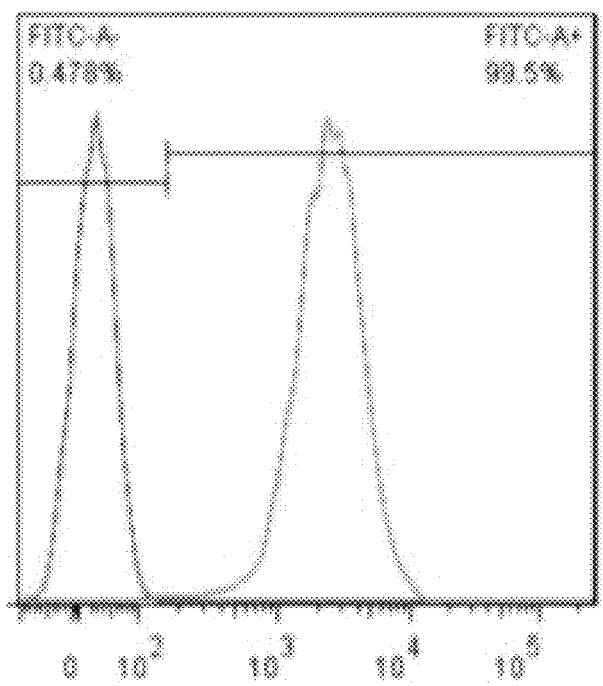
FIG. 3D shows flow cytometry histograms for the CD19expression in the cynomolgus monkey CD19 transfected CHO-K1 cell line (WBP701.CHO-K1.cpro1.FL.C9). The peak on the left represents negative control signal. The right-shifted peak represents the CD19 expression in the detected cell line.
Figure 4A:
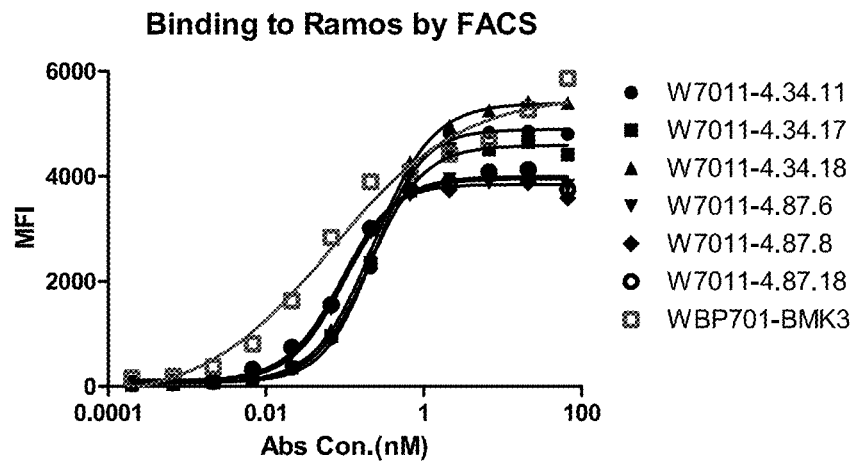
FIG. 4A-4F show binding of selected subclones to Ramos cell by FACS.
Figure 4B:
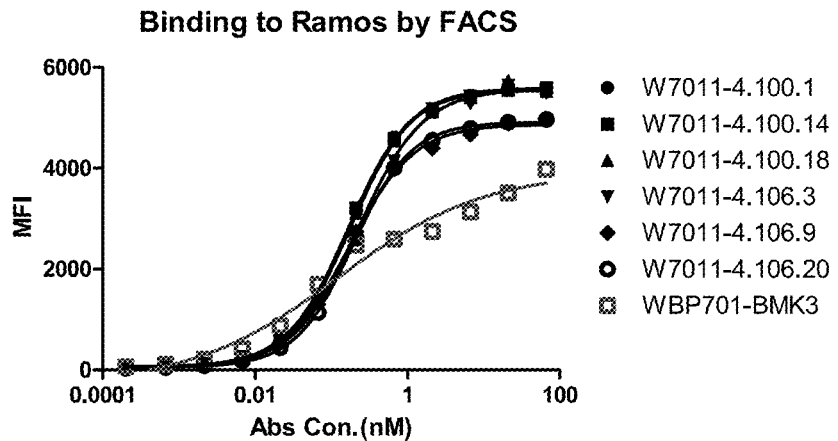
Figure 4C:
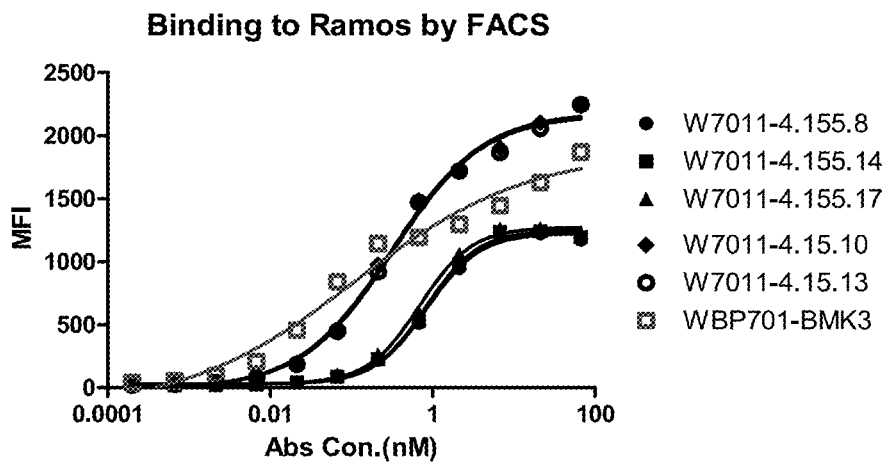
Figure 4D:
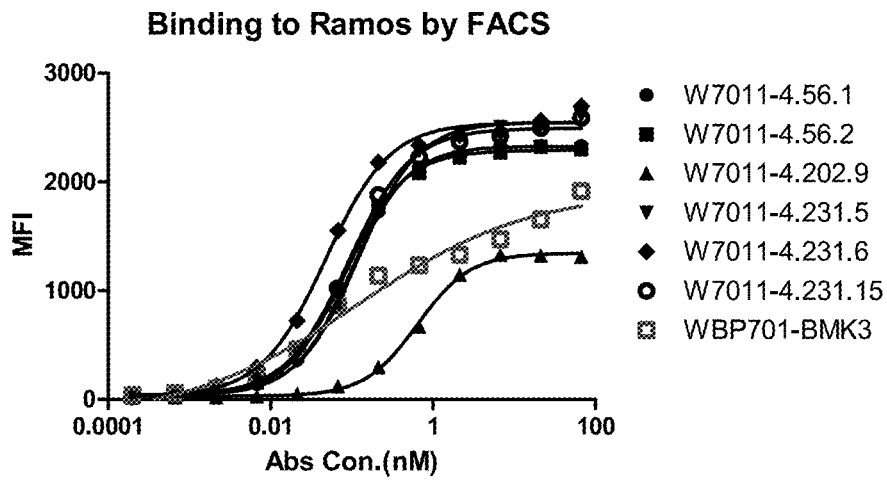
Figure 4E:
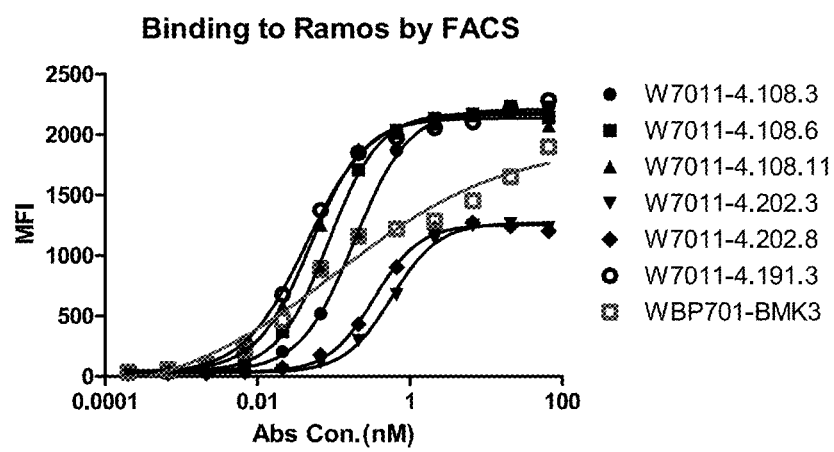
Figure 4F:
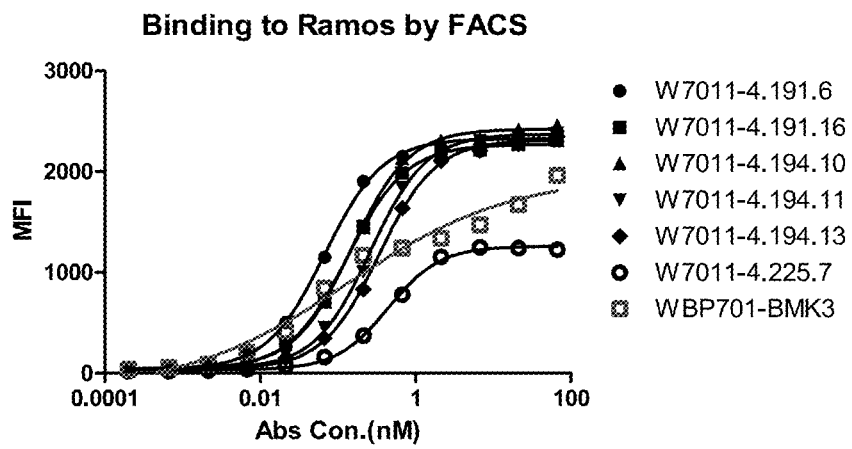

Reference antibodies WBP701-BMK1, WBP701-BMK2 and WBP701-BMK3 generated according to the method above were analyzed on SDS PAGE. FIGS. 1 and 2 showed that all three generated reference antibodies migrated with the apparent molecular mass of 25 kDa and 55 kDa in SDS-PAGE under reducing condition which correspond to light chain and heavy chain. The main band under non-reducing condition correspond to the whole IgG with M.W. of ~150 KD. The purity of the reference antibodies is higher than 95% (see FIGS. 1 and 2).

1.2 Generation Human or Cynomolgus Monkey CD19 Expression Cell Lines

The gene of full length human or cynomolgus monkey CD19 was cloned into pcDNA3.3 vector. Briefly, a volume of 30 mL FreeStyle 293F cells (ThermoFisher-R79007) at a density of $1 \times 10^6$/mL was transfected with 30 µg DNA using Plasfect Reagent (Bioline-46025). The transfected cells were cultured in an incubator setting at 37° C., 8% $CO_2$ and 100 rpm shaking speed. 24 hours after transfection, blasticidin (Invitrogen-A1113902) at a final concentration of 4-10 µg/mL was used to generate the stable pool. The selected clones were tested by FACS using an anti-CD19 antibody. After two to three passages of selection, the cells were enriched by PE conjugated anti-CD19 antibody and anti-PE Microbeads (Miltenyi-013-048-801). Stable single cell clones were isolated by limiting dilution and screened by FACS using anti-CD19 antibody.

The gene of full length human or cynomolgus monkey CD19 was cloned into pcDNA3.3 vector. Each expression vector was then transfected into CHO-K1 cells respectively using Lipofectamine 2000. The cells were cultured in F12-K with 10% FBS. Blasticidin was added 24-48 hours after transfection. After two to three passages of selection, the cells were enriched by PE conjugated anti-CD19 antibody and Anti-PE Microbeads (Miltenyi-013-048-801). Stable single cell clones were isolated by limiting dilution and screened by FACS using anti-CD19 antibody.

The expression of human CD19 and cynomolgus monkey CD19 of transfected cell lines were detected using anti-CD19 antibody by flow cytometry. The transfected cell lines WBP701.293F.hPro1.FL.A2, WBP701.CHO-K1.hPro1.FL.B4, WBP701.cPro1.293F.FL.C1 and WBP701.CHO-K1.cpro1.FL.C9 all showed high expression of human or monkey CD19 (FIGS. 3A-3D).

Example 2: Antibody Generation 2.1 Immunization

Balb/c mice were immunized with CD19 transfected 293F cells. The cell membrane lysate was mixed with adjuvant including CpG-ODN and Adju-Phos or Titer-Max. The mice were immunized twice via footpad, subcutaneous or intraperitoneal routes with two weeks interval. The mice with high serum titer were given a final boost with cell membrane lysate of $1 \times 10^6$ cells/animal and 10 µg of ECD protein/animal in PBS.

2.2 Serum Titer Detection

The serum titer was detected by flow cytometry. The CD19 transfected CHO-K1 cells were spread in 96-well U-bottom plates (BD) at a density of $1 \times 10^5$ cells/well. Mouse serum was diluted at the ratio of 1:3 starting from 100-fold dilution using staining buffer (1×PBS/1% BSA). Serum samples were incubated with cells for 1 hr at 4° C. After washing the cells twice with staining buffer, PE-conjugated goat anti-mouse IgG Fc antibody (Jackson) was added and incubated at 4° C. in the dark for 30 min. The cells were then washed twice and re-suspended in 100 µL staining buffer. The fluorescence intensity was measured by flow cytometry (BD Canto II) and analyzed by FlowJo.

All the mice showed CD19 specific titer. Mice with high serum titer were selected for hybridoma fusion (Table 3).

TABLE 3

| Mouse# | Serum titer | | | | |
|---|---|---|---|---|---|
| | 1 | 2 | 3 | 4 | 5 |
| Pre-bleed on CHO-K1.CD19 cell | <100 | <100 | <100 | <100 | <100 |
| Titer on CHO-K1.CD19 cell | 1968300 | 656100 | 218700 | 656100 | 72900 |
| Titer on parental CHO-K1 cell | 2700 | 2700 | 900 | 300 | 2700 |

2.3 Hybridoma Generation

Lymph nodes cells were fused with Sp2/0 myeloma cells by electro-fusion according to general electro-fusion procedures. After cell fusion, the cells were plated in 96-well plates at $1 \times 10^4$ lymphocytes/well with DMEM medium with 20% FBS and 1% HAT. The plates were incubated at 37° C. for 10-12 days.

2.4 Antibody Screening 2.4.1 Binding to Human CD19

The human CD19 transfected CHO-K1 cells were plated in 96-well U-bottom plates (BD) at a density of $1 \times 10^5$ cells/well. Hybridoma supernatants were transferred to the plates and incubated with cells for 1 hr at 4° C. The cells were then washed twice with staining buffer (BSA/1×PBS). PE-conjugated goat anti-mouse IgG Fc antibody (Jackson 115-115-164), was added and incubated at 4° C. in the dark for 30 min. The cells were then washed twice and re-suspended in 100 µL staining buffer. The fluorescence intensity was measured by flow cytometry (BD Canto II) and analyzed by FlowJo.

2.4.2 Binding to Cynomolgus Monkey CD19

The cynomolgus CD19 transfected CHO-K1 cells were plated in 96-well U-bottom plates (BD) at a density of $1 \times 10^5$ cells/well. Hybridoma supernatants were transferred to the plates and incubated with cells for 1 hr at 4° C. The cells were then washed twice with staining buffer (BSA/1×PBS). PE-conjugated goat anti-mouse IgG Fc antibody (Jackson 115-115-164), was added and incubated at 4° C. in the dark for 30 min. The cells were then washed twice and re-suspended in 100 µL staining buffer. The fluorescence intensity was measured by flow cytometry (BD Canto II) and analyzed by FlowJo.

2.4.3 Internalization Assay

Fab-ZAP is a chemical conjugate of goat anti-human monovalent antibody and the ribosome-inactivating protein, saporin. Fab-ZAP is used to determine the internalization ability of antibodies. IgG concentration in hybridoma supernatants were determined by ELISA. Normalized hybridoma supernatants and Fab-ZAP were mixed at the molar ratio of 1:3. Ramos cells (5000/well) were incubated with different concentrations of the conjugate in a 37° C., 5% $CO_2$ incubator for 96 hrs. Cell cytotoxicity was determined by CellTiter Glo (Promega). Cell viability (%) was calculated as follows: cell viability (%)=RLU of sample/RLU of control×100%, wherein RLU stands for relative light units.

Results:

Hybridoma supernatant was used for primary screen. The primary binding screen identified 116 hybridomas which can produce antigen-specific binding antibodies. The antigen-specific hybridomas were then confirmed binding on CD19 transfected CHO-K1 cell and counter screened on parental CHO-K1 cell. The selected 40 hybridoma lines were confirmed binding on Ramos cell. The positive binders were then screened in Fab-Zap assay. 13 hybridoma lines were selected for subcloning based on binding and internalization ability.

2.5 Subcloning of Hybridoma

Hybridoma cells of each selected lines were plated in 96-well plates at the density of 1 cell/well. The plates were kept in a humidified incubator at 37° C., 6% $CO_2$ for 10-12 days. The single clones were picked and tested by FACS.

2.6 Isotype

Antibody Isotype was identified by ELISA. Plates (Nunc) were coated with goat anti-mouse IgG1, anti-mouse IgG2a, anti-mouse IgG2b, anti-mouse IgG3, anti-mouse IgM antibodies at 2 µg/ml overnight at 4° C. After blocking and washing, the hybridoma supernatants were transferred to the coated plates and incubate at room temperature for 1 h. The plates were then incubated with secondary antibody goat anti-mouse kappa HRP or goat anti mouse lambda HRP (Southern Biotech) for 45 min. After washing, TMB substrate was added and the reaction was stopped by 2M HCl. The absorbance at 450 nm was read using a microplate reader (Molecular Device).

Results:

Hybridoma subclones were verified by binding to CD19 cell line, and their isotypes were also detected (see Table 4). The selected subclones were purified and further evaluated in binding assay, internalization assay, cross-family binding assay and binning assay.

TABLE 4

Antibody isotype

| Antibody | Isotype |
|---|---|
| WBP7011_4.34.11 | mouse IgG2a, kappa |
| WBP7011_4.87.6 | mouse IgG2a, kappa |
| WBP7011_4.100.1 | mouse IgG2a, kappa |
| WBP7011_4.106.3 | mouse IgG2a, kappa |
| WBP7011_4.155.8 | mouse IgG2a, kappa |
| WBP7011_4.15.10 | mouse IgG1, kappa |
| WBP7011_4.56.1 | mouse IgG2a, kappa |
| WBP7011_4.202.9 | mouse IgG2a, kappa |
| WBP7011_4.231.5 | mouse IgG2b, kappa |
| WBP7011_4.108.3 | mouse IgG2a, kappa |
| WBP7011_4.191.3 | mouse IgG1, kappa |
| WBP7011_4.194.10 | mouse IgG2b, kappa |
| WBP7011_4.225.7 | mouse IgG2a, kappa |

Example 3: Antibody Candidates Characterization 3.1 Antibody Purification

Harvested hybridoma supernatants were loaded to Protein A column (Mab Select SuRe, GE) after adjusting pH to 7.0. Antibodies were eluted by Glycine followed with immediately neutralization using 1 M Tris. Antibody concentration was tested by Nano Drop (Thermal-Fisher). The purity of proteins was evaluated by SDS-PAGE (Invitrogen, NuPAGE 4%-12% Bis-Tris Gel) and HPLC-SEC (Agilent).

3.2 Affinity by FACS

The CD19 transfected CHO-K1 cells or Ramos cells were plated in a 96-well plates (BD) at a density of $5 \times 10^4$ cells/well. Antibodies to be tested were serially diluted in the staining buffer (1×PBS/1% BSA) and incubated with cells at 4° C. for 1 hr. After discarding the supernatants, PE conjugated Goat Anti-Mouse IgG Fc antibody (Jackson 115-1154-164 was added and incubated at 4° C. in the dark for 30 min. The cells were washed once and re-suspended in 100 µL staining buffer. The fluorescence intensity was measured by flow cytometry (BD Canto II) and analyzed by FlowJo. Bound IgG and free IgG concentration were calculated based on the fluorescence intensities of the quantitative beads (PE fluorescence quantitation kit, BD 340495). $K_D$ was calculated using Scatchard Analysis.

Results:

The affinity of selected candidate antibodies were tested on CD19 transfected CHO-K1 cell by flow cytometry. $K_D$ values were summarized in Table 5. All the candidate antibodies showed sub-nanomolar binding affinity to human CD19.

TABLE 5

Affinity of candidate antibodies

| Antibody | KD (M) |
|---|---|
| W7011-4.34.11 | 1.81E−10 |
| W7011-4.87.6 | 9.55E−11 |
| W7011-4.100.1 | 2.13E−10 |
| W7011-4.106.3 | 2.31E−10 |
| W7011-4.155.8 | 9.49E−10 |
| W7011-4.15.10 | 1.70E−10 |
| W7011-4.56.1 | 1.18E−10 |
| W7011-4.202.9 | 8.47E−10 |
| W7011-4.231.5 | 1.70E−10 |
| W7011-4.108.3 | 2.52E−10 |
| W7011-4.191.3 | 1.14E−10 |
| W7011-4.194.10 | 4.20E−10 |
| W7011-4.225.7 | 7.35E−10 |

3.3 Binding to Human CD19

The Ramos cells were plated in 96-well U-bottom plates (BD) at a density of $1 \times 10^5$ cells/well. The purified antibody were serially diluted in the staining buffer (1×PBS/1% BSA) and incubated with cells for 1 hr at 4° C. The cells were then washed twice with staining buffer (BSA/1×PBS). PE-conjugated goat anti-mouse IgG Fc antibody (Jackson 115-115-164), was added and incubated at 4° C. in the dark for 30 min. The cells were then washed twice and re-suspended in 100 µL staining buffer. The fluorescence intensity was measured by flow cytometry (BD Canto II) and analyzed by FlowJo.

Binding activity of the selected subclones were tested on Ramos cell by flow cytometry (FIG. 4). The binding EC50 values were summarized in Table 6. All the candidate antibodies showed sub-nanomolar EC50 in the binding assay.

TABLE 6

Binding activity of selected subclones

| Clone# | EC50 (nM) |
|---|---|
| W7011-4.34.11 | 0.23 |
| W7011-4.34.17 | 0.21 |
| W7011-4.34.18 | 0.24 |
| W7011-4.87.6 | 0.10 |
| W7011-4.87.8 | 0.09 |

TABLE 6-continued

Binding activity of selected subclones

| Clone# | EC50 (nM) |
|---|---|
| W7011-4.87.18 | 0.09 |
| W7011-4.100.1 | 0.17 |
| W7011-4.100.14 | 0.17 |
| W7011-4.100.18 | 0.18 |
| W7011-4.106.3 | 0.23 |
| W7011-4.106.9 | 0.18 |
| W7011-4.106.20 | 0.19 |
| W7011-4.155.8 | 0.85 |
| W7011-4.155.14 | 0.82 |
| W7011-4.155.17 | 0.69 |
| W7011-4.15.10 | 0.31 |
| W7011-4.15.13 | 0.32 |
| W7011-4.56.1 | 0.10 |
| W7011-4.56.2 | 0.08 |
| W7011-4.202.9 | 0.64 |
| W7011-4.231.5 | 0.12 |
| W7011-4.231.6 | 0.05 |
| W7011-4.231.15 | 0.09 |
| W7011-4.108.3 | 0.19 |
| W7011-4.108.6 | 0.09 |
| W7011-4.108.11 | 0.05 |
| W7011-4.202.3 | 0.58 |
| W7011-4.202.8 | 0.34 |
| W7011-4.191.3 | 0.04 |
| W7011-4.191.6 | 0.07 |
| W7011-4.191.16 | 0.13 |
| W7011-4.194.10 | 0.15 |
| W7011-4.194.11 | 0.26 |
| W7011-4.194.13 | 0.34 |
| W7011-4.225.7 | 0.45 |
| W7011-4.225.9 | 0.39 |
| WBP701.BMK3 | 0.11 |

3.4 Binding to Cynomogus Monkey CD19

The cynomolgus CD19 transfected CHO-K1 cells were plated in 96-well U-bottom plates (BD) at a density of 1×10$^5$ cells/well. The purified antibody were serially diluted in the staining buffer (1×PBS/1% BSA) and incubated with cells for 1 hr at 4° C. The cells were then washed twice with staining buffer (BSA/1×PBS). PE-conjugated goat anti-mouse IgG Fc antibody (Jackson 115-115-164), was added and incubated at 4° C. in the dark for 30 min. The cells were then washed twice and re-suspended in 100 μL staining buffer. The fluorescence intensity was measured by flow cytometry (BD Canto II) and analyzed by FlowJo.

Figure 5A:
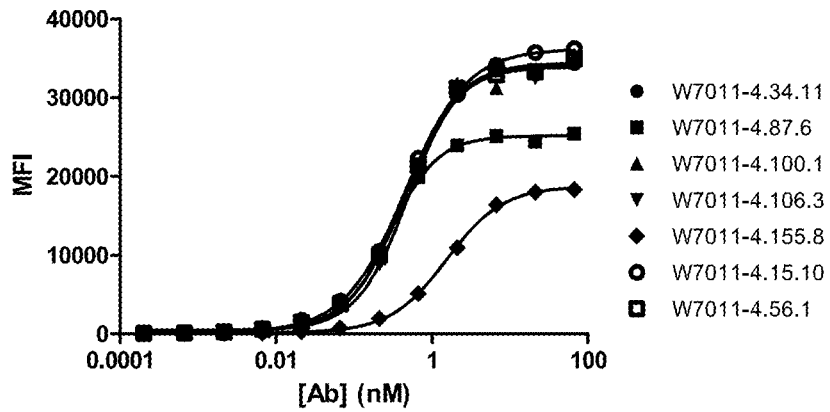
FIG. 5A-5C show binding of selected subclones to cynomolgus monkey CD19 expressing cell (WBP701.CHO-K11.cynoPro1) by FACS.
Figure 5B:
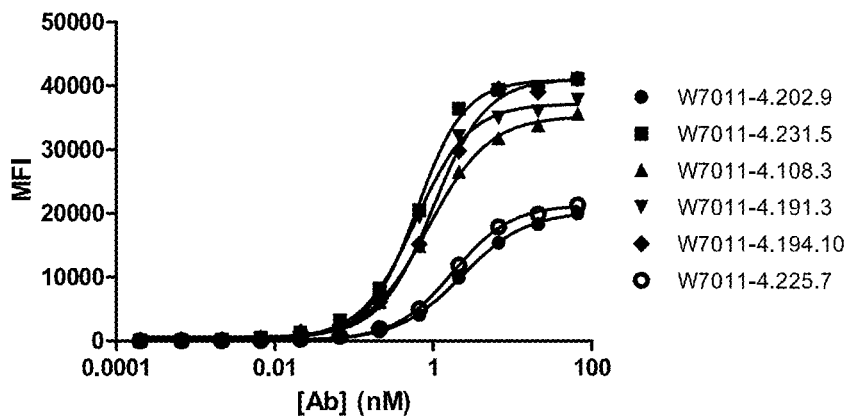
Figure 5C:
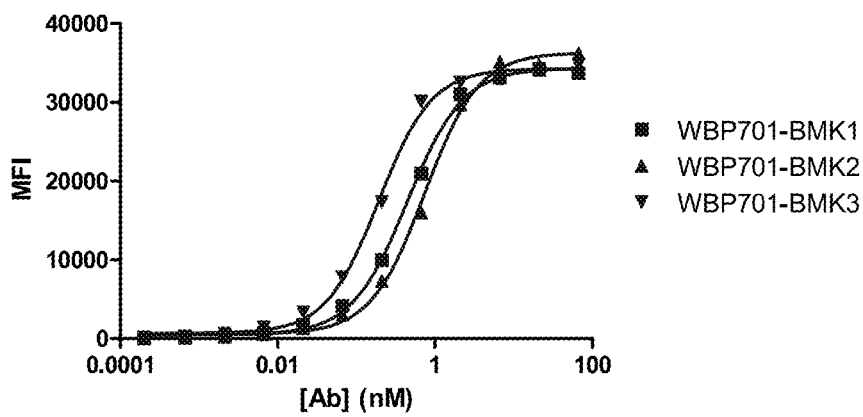
Figure 6A:
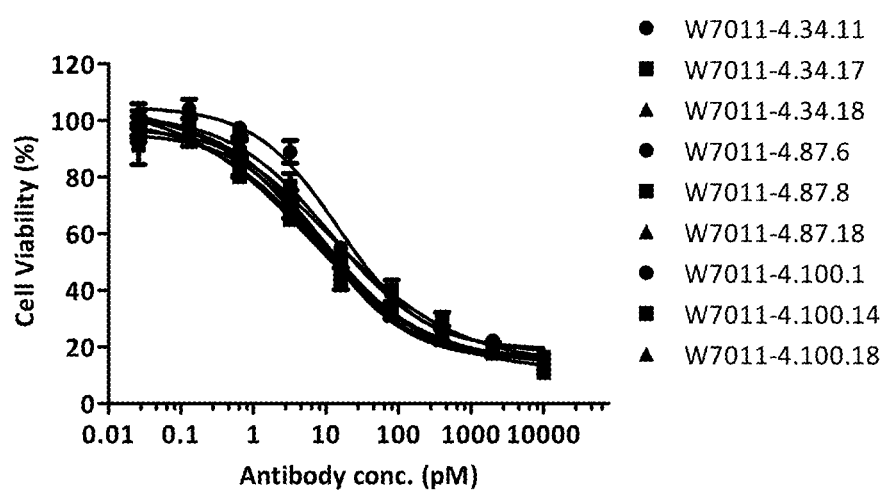
FIG. 6A-6E show Fab-Zap assay of selected subclones.
Figure 6B:
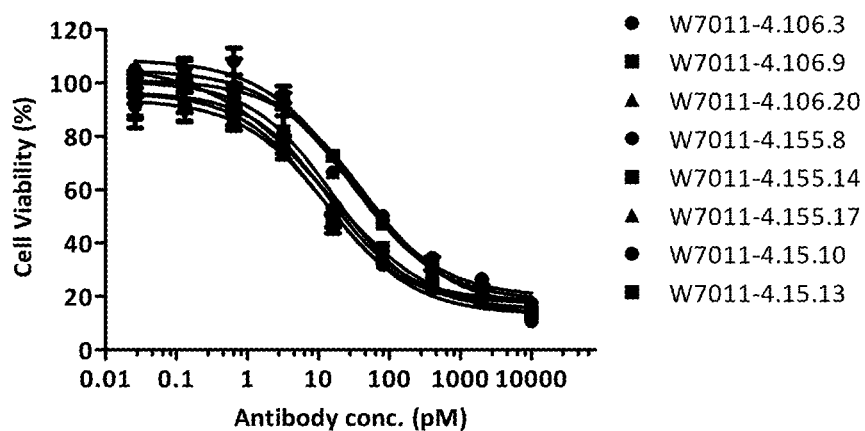
Figure 6C:
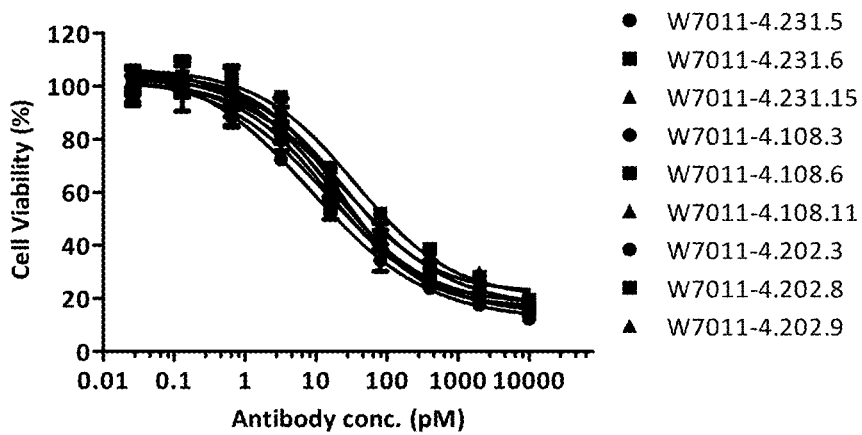
Figure 6D:
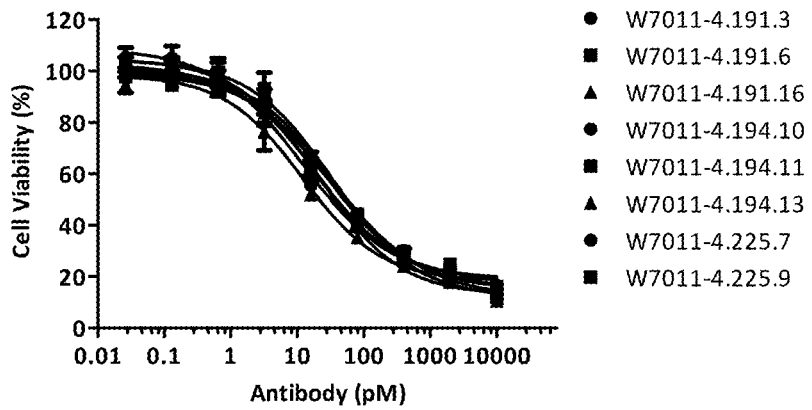
Figure 6E:
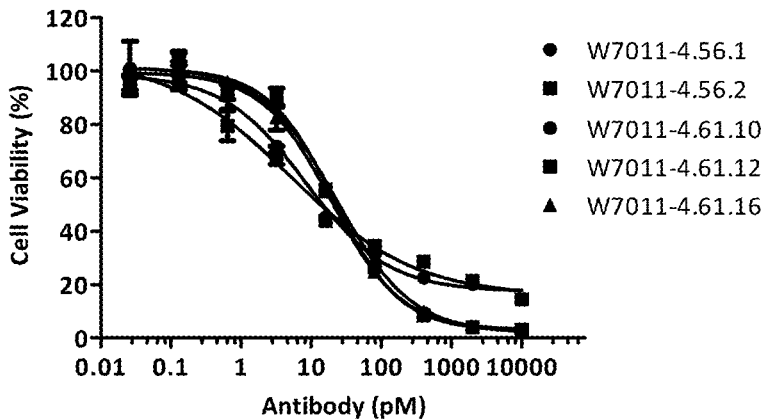

The binding activity to cynomogus monkey CD19 of candidate antibodies was evaluated using cynomolgus monkey CD19 transfected CHO-K1 cell line (FIG. 5). The binding EC50 values were summarized in Table 7. All the selected clones showed strong binding to cynomolgus monkey CD19 cell.

TABLE 7

Binding activity to cynomolgus monkey CD19

| Antibody | EC50 (nM) |
|---|---|
| W7011-4.34.11 | 0.4427 |
| W7011-4.87.6 | 0.285 |
| W7011-4.100.1 | 0.4384 |
| W7011-4.106.3 | 0.4959 |
| W7011-4.155.8 | 1.542 |
| W7011-4.15.10 | 0.4598 |
| W7011-4.56.1 | 0.4381 |
| W7011-4.202.9 | 2.299 |
| W7011-4.231.5 | 0.628 |
| W7011-4.108.3 | 0.8634 |
| W7011-4.191.3 | 0.5984 |
| W7011-4.194.10 | 0.9959 |

TABLE 7-continued

Binding activity to cynomolgus monkey CD19

| Antibody | EC50 (nM) |
|---|---|
| W7011-4.225.7 | 1.77 |
| WBP701-BMK1 | 0.4473 |
| WBP701-BMK2 | 0.7407 |
| WBP701-BMK3 | 0.1936 |

3.5 Internalization Assay

Fab-ZAP is used to determine the internalization ability of antibodies. The serially diluted antibodies were mixed with Fab-Zap at the molar ratio of 1:3. Ramos cells (5000/well) were incubated with different concentrations of the conjugate in a 37° C., 5% $CO_2$ incubator for 96 hours. Cell cytotoxicity was determined by CellTiter Glo (Promega). Cell viability (%) was calculated as follows: cell viability (%)=RLU of sample/RLU of control×100%.

Internalization activity of the selected subclones were tested on Ramos using Fab-Zap assay (FIG. 6). The EC50 of cell viability were summarized in Table 8. All the candidate antibodies can internalize on Ramos cell and showed picomolar EC50 values in Fab-Zap assay.

TABLE 8

Fab-Zap assay

| Antibody | $EC_{50}$ (pM) |
|---|---|
| W7011-4.34.11 | 7 |
| W7011-4.34.17 | 8.9 |
| W7011-4.34.18 | 8.9 |
| W7011-4.87.6 | 8.5 |
| W7011-4.87.8 | 5.8 |
| W7011-4.87.18 | 7.2 |
| W7011-4.100.1 | 14.8 |
| W7011-4.100.14 | 11.5 |
| W7011-4.100.18 | 11 |
| W7011-4.106.3 | 13.6 |
| W7011-4.106.9 | 12.7 |
| W7011-4.106.20 | 16.2 |
| W7011-4.155.8 | 27.6 |
| W7011-4.155.14 | 44.9 |
| W7011-4.155.17 | 30.2 |
| W7011-4.15.10 | 13.9 |
| W7011-4.15.13 | 11 |
| W7011-4.56.1 | 8.4 |
| W7011-4.56.2 | 5.2 |
| W7011-4.61.10 | 23.1 |
| W7011-4.61.12 | 21.1 |
| W7011-4.61.16 | 19.4 |
| W7011-4.231.5 | 8.5 |
| W7011-4.231.6 | 14.8 |
| W7011-4.231.15 | 14.7 |
| W7011-4.108.3 | 20.6 |
| W7011-4.108.6 | 15.7 |
| W7011-4.108.11 | 18.7 |
| W7011-4.202.3 | 28.3 |
| W7011-4.202.8 | 35.4 |
| W7011-4.202.9 | 23.6 |
| W7011-4.191.3 | 18.4 |
| W7011-4.191.6 | 19.1 |
| W7011-4.191.16 | 18.2 |
| W7011-4.194.10 | 11.7 |
| W7011-4.194.11 | 11.8 |
| W7011-4.194.13 | 12.8 |
| W7011-4.225.7 | 15 |
| W7011-4.225.9 | 15.8 |

3.6 Epitope Binning

The CD19 transfected cells WBP701.CHO-K1.hPro1.B4 were plated in a 96-well plates (BD) at a density of 1×10$^5$ cells/well. Antibodies to be tested were serially diluted and mixed with reference antibodies. The mixtures were added to the plate and incubated for 30 min at 4° C. After washing PE-conjugated Goat anti-human IgG Fc antibody (Jackson), was added and incubated at 4° C. in the dark for 30 min. The cells were washed twice and re-suspended in 100 μL staining buffer (1×PBS/1% BSA). The fluorescence intensity was measured by flow cytometry (BD Canto II) and analyzed by FlowJo.

Figure 7A:
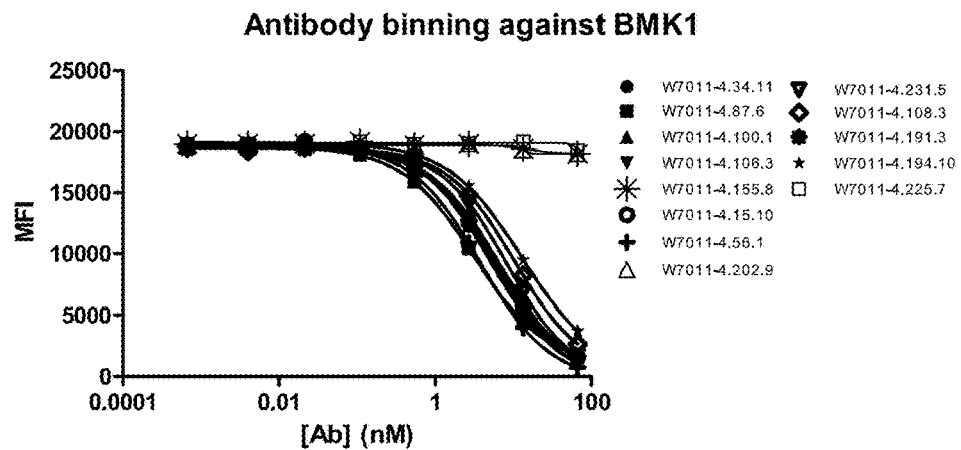
FIG. 7A-7C show candidate antibody binning against BMK1, BMK2 and BMK3 antibodies by FACS.
Figure 7B:
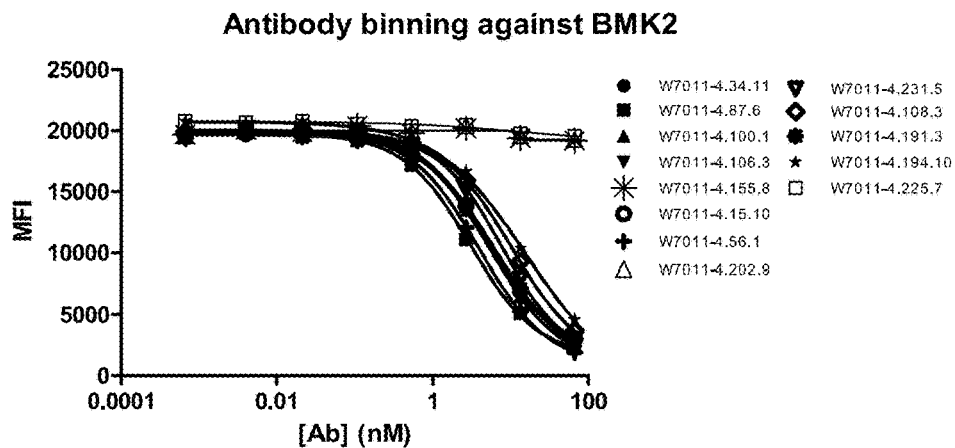
Figure 7C:
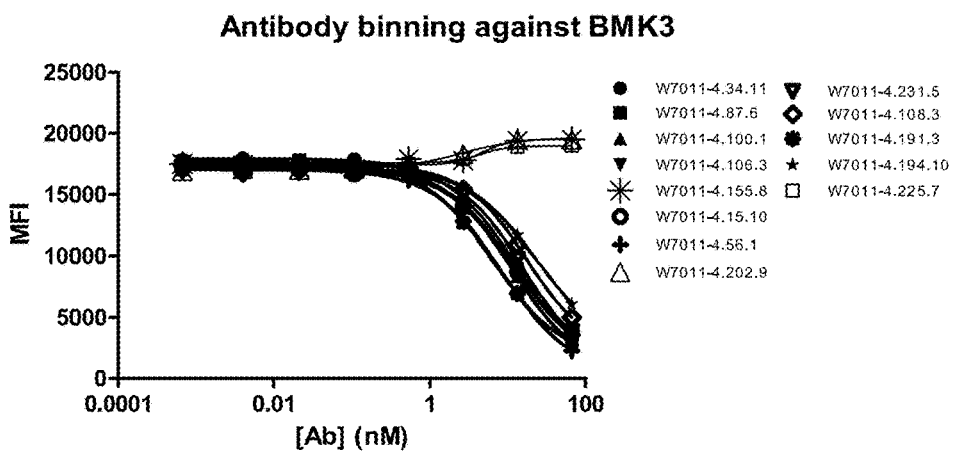

The selected candidate clones were tested competitive binding against BMK1, BMK2 and BMK3 reference antibodies. Some candidate antibodies can block the binding of reference antibodies to CD19. W7011-4.155.8, W7011-4.202.9 and W7011-4.225.7 do not compete with reference antibodies (FIG. 7). Based on the competitive binding result, the antibodies are assigned to two epitope bins (Table 9).

TABLE 9

Epitope Bin of candidate antibodies

| Bin1 | Bin2 |
|---|---|
| WBP701-BMK1 | W7011-4.155.8 |
| WBP701-BMK2 | W7011-4.202.9 |
| WBP701-BMK3 | W7011-4.225.7 |
| W7011-4.34.11 | |
| W7011-4.87.6 | |
| W7011-4.100.1 | |
| W7011-4.106.3 | |
| W7011-4.15.10 | |
| W7011-4.56.1 | |
| W7011-4.231.5 | |
| W7011-4.108.3 | |
| W7011-4.191.3 | |
| W7011-4.194.10 | |

Upon sequencing of the antibody clones, we found that the amino acid sequence of antibody clones W7011-4.155.8, W7011-4.202.9 and W7011-4.225.7 are identical. The amino acid and nucleic acid sequences for the antibody clones are listed in the detailed description section.

Example 4: Antibody Humanization and Affinity Maturation 4.1 Hybridoma Sequencing RNA were isolated from hybridoma cells using Trizol reagent (Invitrogen-15596018). cDNA was amplified using 5'-RACE kit (Takara-28001488), followed by PCR amplification using 3'-degenerated primers and 3'-adaptor primers (ExTaq: Takara-RR001B). PCR fragments was inserted into pMD18-T vector (Takara-D101C) and sent for sequencing (Shanghai Biosune).

Antibody sequences (mouse) from hybridoma are as shown by SEQ ID NOs: 94-123.

4.2 Humanization

"Best Fit" approach was used to humanize antibody light and heavy chains. For light chains amino acid sequences of corresponding V-genes were blasted against in-house human germline V-gene database. The sequence of humanized VL-gene was derived by replacing human CDR sequences in the top hit with mouse CDR sequences using Kabat CDR definition. For heavy chain 4 humanized sequences were derived, for light chain 1 humanized sequence was derived first according to the method described above, and 3 additional sequences were created by blasting mouse frameworks against human germline V-gene database. Frameworks were defined using extended CDR definition where Kabat CDR1 was extended by 5 amino acids at N-terminus. Top three hits were used to derive sequences of humanized V genes. Humanized genes were back-translated, codon-optimized for mammalian expression, and synthesized by GeneArt Costum Gene Synthesis (Life Technologies). Synthetic genes were re-cloned into IgG expression vector, expressed, and purified.

4.3 Affinity Maturation

Each amino acid of the six complementary-determining regions (CDRs) was individually mutated to the 20 amino acids using a hybridization mutagenesis method (Kunkel, 1985). DNA primers containing a NNS codon encoding 20 amino acids were used to introduce mutation to each targeted CDR position. The individual degenerate primers were used in hybridization mutagenesis reactions. Synthesis products for VH and VL CDRs were pooled respectively. 200 ng of the pooled library DNA was transfected into BL21 for the production of scFv fragments.

The mutants were firstly screened by capture ELISA using periplasmic extract of bacteria. The 96-well Maxisorp Immunoplate (Nunc) was coated with anti-c-myc antibody in coating buffer (200 mM $Na_2CO_3$/$NaHCO_3$, pH9.2) overnight at 4° C. After blocking with Casein for 1 hr at room temperature, periplasmic extract samples were then added to the plate and incubated at room temperature for 1 hr. After washing, biotinylated CD19 ECD protein was added and incubated for 1 hr at room temperature, followed by incubation with Strepatavidin-HRP for 1 hr. After washing, TMB substrate was added and the reaction was stopped by 2M HCl. The absorbance at 450 nm was read using a microplate reader (Molecular Device).

Clones exhibiting an optical density (OD) signal at 450 nm greater than the parental clone were picked for sequencing. The unique clones were confirmed by FACS under normalized scFv concentration in order to determine the relative binding affinity of the mutant scFv and the parental antibody.

The point mutations in VH and VL determined to be beneficial for binding to antigen were further combined to gain additional binding synergy. The combinatorial mutants were expressed as scFvs and screened using the capture ELISA. Clones exhibiting an optical density (OD) signal at 450 nm greater than the parental clone were sequenced and further confirmed by binding FACS.

4.4 Binding Affinity of Engineered Antibodies 4.4.1 WBP7011-4.34.11-z1-m5-IgG1k

Figure 8:
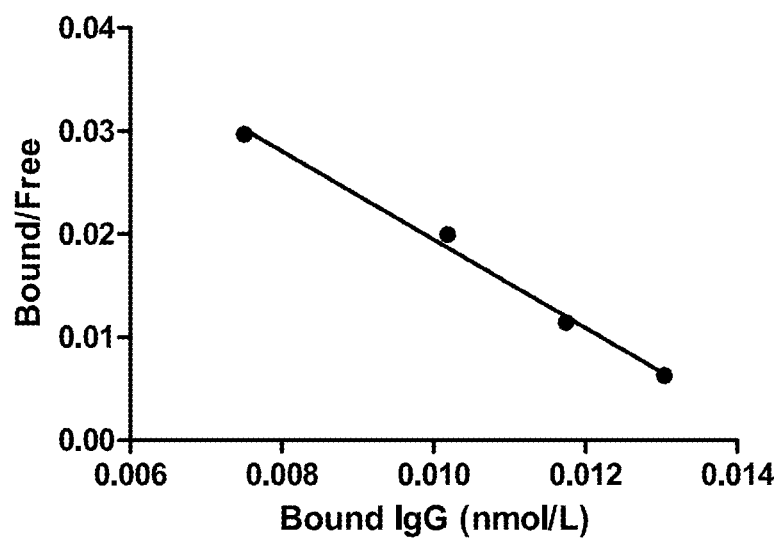
FIG. 8 shows Scarchard binding affinity analysis of antibody WBP7011-4.34.11-z1-m5-IgG1k to Ramos cell by FACS.

Antibody WBP7011-4.34.11 was humanized and affinity matured. The affinity of engineered antibody WBP7011-4.34.11-z1-m5 was measured on Ramos cell by FACS (FIG. 8). $K_D$ was calculated using Scatchard Analysis. The affinity of WBP7011-4.34.11-z1-m5-IgG1k is 0.23 nM.

4.4.2 WBP7011-4.87.6-z1-IgG1k (N-S)

Figure 9:
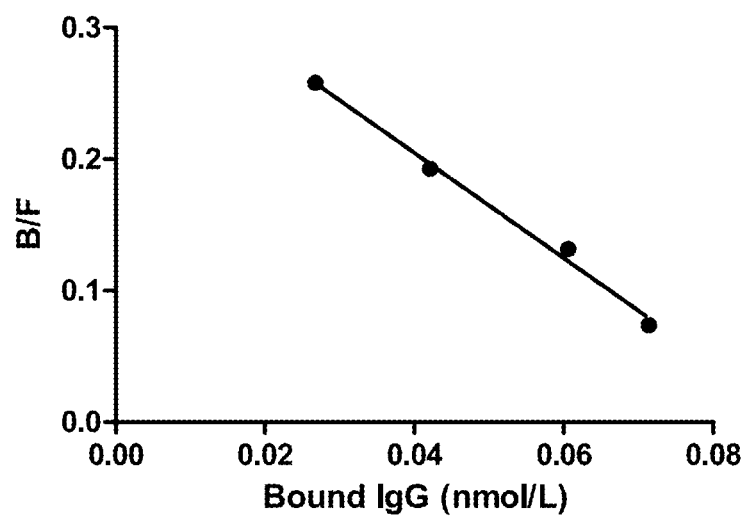
FIG. 9 shows Scarchard binding affinity analysis of antibody WBP7011-4.87.6-z1-IgG1K (N-S) to Ramos cell by FACS.

Antibody WBP7011-4.87.6 was humanized and engineered on PTM risky residues. The affinity of final lead antibody WBP7011-4.87.6-z1-IgG1k (N-S) was measured on Ramos cell by FACS (FIG. 9). $K_D$ was calculated using Scatchard Analysis. The affinity of WBP7011-4.87.6-z1-IgG1k (N-S) is 0.25 nM.

4.4.3 W7011-4.155.8-z1-uIgG1K

Figure 10:
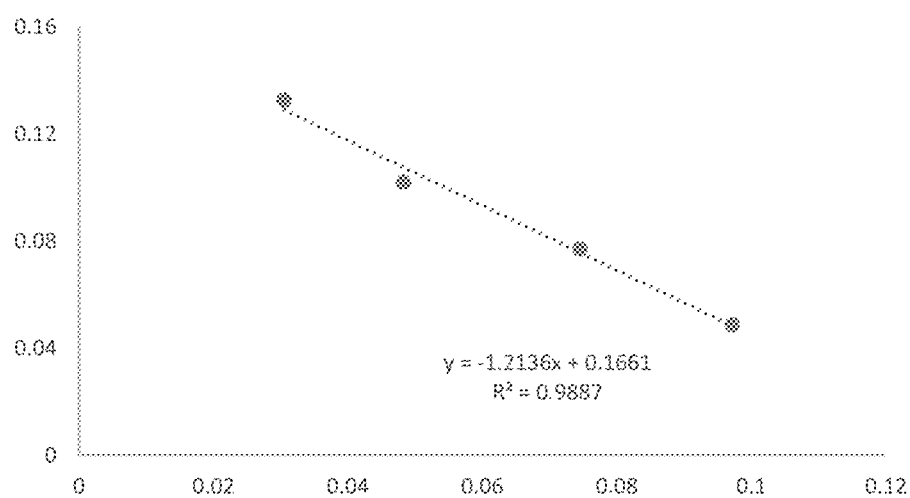
FIG. 10 shows Scarchard binding affinity analysis of antibody W7011-4.155.8-z1-uIgG1K to Ramos cell by FACS.

Antibody W7011-4.155.8 was humanized. The affinity of humanized antibody W7011-4.155.8-z1-uIgG1K was measured on CD19 transfected CHO-K1 cell by FACS (FIG. 10). KD was calculated using Scatchard Analysis. The affinity of W7011-4.155.8-z1-uIgG1K is 0.82 nM.

4.5 Engineered Antibody Sequence

Engineered antibody sequences are as shown by SEQ ID NOs: 124-135.

Example 5: Generation of Antibody-Drug Conjugate (ADC)

Antibodies were buffer exchanged into PBS (pH7.4) buffer and mixed with DMA (Alfa Aesar). DM1-SMCC (BrightGene) was then added and the mixture was incubated at 22° C. with gentle rotation for conjugation.

To remove free drug, the ADC product was buffer exchanged to ADC storage buffer using 30 KDa ultrafilter tube (Millipore). After 8 times buffer exchange, ADC product was filtered with 0.22 µm membrane for final characterization.

Concentration of ADC was characterized with UV-vis (NanoDrop). DAR valure was determined by UV-vis and SEC-HPLC. The aggregation level and purity were determined by SEC-HPLC. Free drug was determined by RP-HPLC. The endotoxin level was determined by kinetic turbidimetric assay.

The lead antibodies were conjugated with DM1. The concentration, purity, DAR, aggregation level and free drug % were evaluated after conjugation (Table 10).

TABLE 10

Characterization of DM1 conjugated antibody

| Antibody | Conc. mg/ml | Purity % | Free Drug % | Endo. EU/mg | UV-DAR | SEC-DAR | Aggr % |
|---|---|---|---|---|---|---|---|
| W7011-BMK1-DM1 | 14.2 | 95.45 | 0 | 0.039 | 3.57 | 3.57 | 4.54 |
| W7011-4.87.6-z1-IgG1K(N-S)-DM1 | 9.71 | 97.7 | 1.06 | 2.36 | 3.38 | 2.95 | 2.31 |
| W7011-4.34.11-z1-m5-1gG1K-DM1 | 6.45 | 96.38 | 0 | limits | 3.32 | 3.38 | 3.02 |
| IgG1K isotype control-DM1 | 5.85 | 98.47 | 0 | 0.086 | 2.86 | 2.69 | 1.53 |

Example 6: Cell Toxicity Analysis of ADC

B lymphoma cells (5000/well) were incubated with various concentrations of DM1-conjugated antibodies at 37° C. for 72 hrs. Cell cytotoxicity was determined by CellTiter Glo (Promega). Cell viability (%) was calculated as follows: cell viability (%)=RLU of sample/RLU of control×100%.

Figure 11:
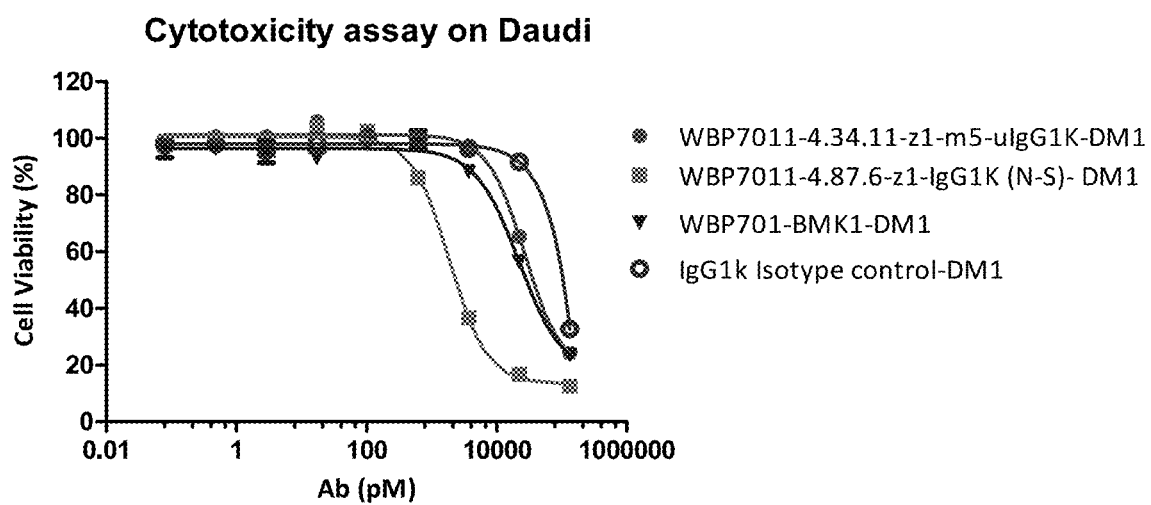
FIG. 11 shows cytotoxicity assay of humanized antibody-drug-conjugates W7011-4.155.8-z1-uIgG1K-DM1 and WBP7011-4.87.6-z1-IgG1K (N-S)-DM1 on Daudi cell.
Figure 12:
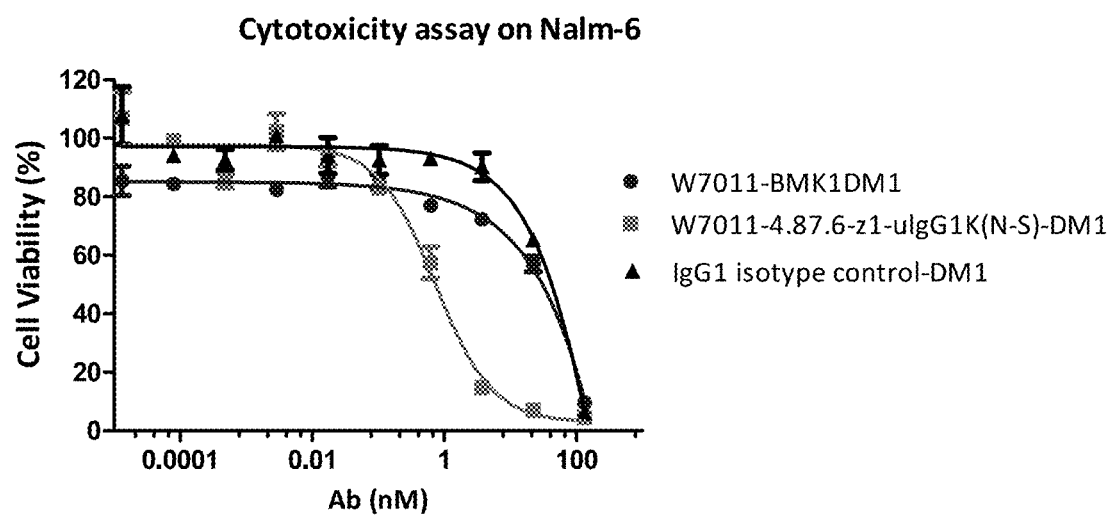
FIG. 12 shows cytotoxicity assay of humanized antibody-drug-conjugate WBP7011-4.87.6-z1-IgG1K (N-S)-DM1 on Nalm-6 cell.
Figure 13:
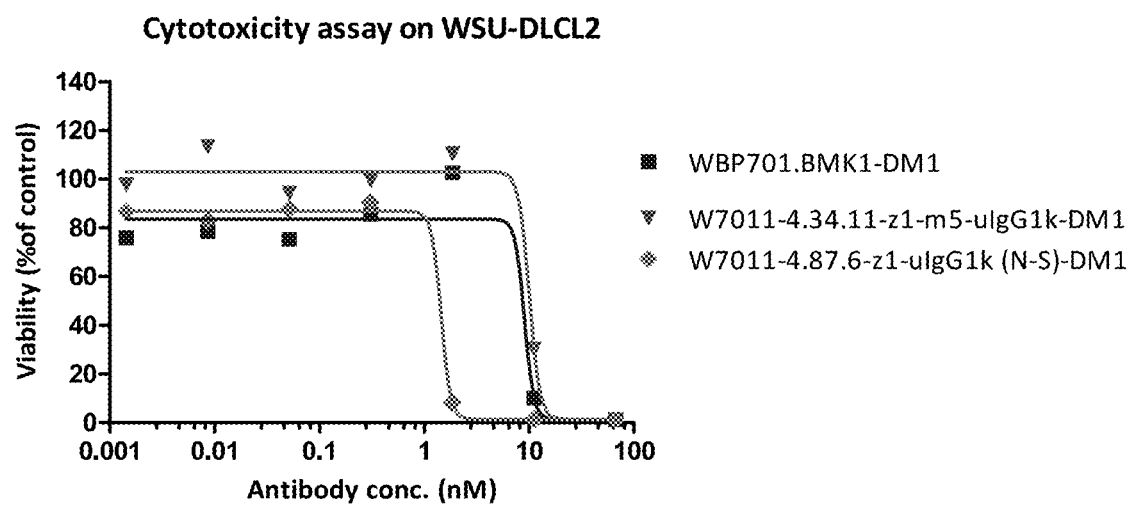
FIG. 13 shows cytotoxicity assay of humanized antibody-drug-conjugates W7011-4.155.8-z1-uIgG1K-DM1 and WBP7011-4.87.6-z1-IgG1K (N-S)-DM1 on WSU-DLCL2 cell.

DM1 conjugated antibodies were tested in cytotoxicity assay on Daudi, Nalm-6 and WSU-DLCL2 cells (FIGS. 11, 12, 13). The EC50 values were summarized in Tables 11, 12 and 13. ADC WBP7011-4.87.6-z1-IgG1K (N-S)-DM1 showed better cytotoxicity activity than WBP701-BMK1-DM1 on all the tested tumor cells. ADC WBP7011-4.34.11-z1-m5-uIgG1K-DM1 showed comparable cytotoxicity activity with WBP701-BMK1-DM1.

TABLE 11

Cytotoxicity assay on Daudi

| Antibody | EC50 (nM) |
|---|---|
| WBP7011-4.34.11-z1-m5-uIgG1K-DM1 | 27 |
| WBP7011-4.87.6-z1-IgG1K (N-S)-DM1 | 1.9 |
| WBP701-BMK1-DM1 | 22 |
| IgG1k isotype contro-DM1 | NA |

TABLE 12

Cytotoxicity assay on Nalm-6 cell

| Antibody | EC50 (nM) |
|---|---|
| WBP7011-4.87.6-z1-IgG1K (N-S)-DM1 | 0.73 |
| WBP701-BMK1-DM1 | NA |
| IgG1k isotype contro-DM1 | NA |

TABLE 13

Cytotoxicity assay on WSU-DLCL2 cell

| Antibody | EC50 (nM) |
|---|---|
| WBP7011-4.34.11-z1-m5-uIgG1K-DM1 | 10.1 |
| WBP7011-4.87.6-z1-IgG1K (N-S)-DM1 | 1.4 |
| WBP701-BMK1-DM1 | 9.0 |

Example 7: Anti-Tumor Analysis of ADC

7.1 Cell Culture

The Nalm-6 tumor cells were maintained in vitro as a suspension culture in RPMI-1640 supplemented with 10% fetal bovine serum, at 37° C. in a humidified atmosphere (95% air and 5% $CO_2$). The tumor cells were routinely subcultured twice weekly. The cells growing in an exponential growth phase were harvested and counted for tumor inoculation.

7.2 Tumor Inoculation and Group Assignment

Each mouse was implanted subcutaneously at the right flank with Nalm-6 tumor cells (10 million+Matrigel) for tumor development. The treatments were started when the average tumor volume reaches 113 $mm^3$. The test articles administration and the animal numbers in each group were shown in the following table.

TABLE 14

Test ADCs administration and the animal numbers in each group

| Group | Treatment | n | Dose (mg/kg) | Dosing Volume (ul/g) | Dosing Route | Schedule |
|---|---|---|---|---|---|---|
| 1 | Isotype Control-DM1 | 6 | 10 | 10 | i.v. | Biw * 3 weeks |
| 2 | W7011-BMK1-DM1 | 6 | 1 | 10 | i.v. | Biw * 3 weeks |
| 3 | W7011-BMK1-DM1 | 6 | 10 | 10 | i.v. | Biw * 3 weeks |
| 4 | W7011-4.87.6-z1-uIgGlk (N-S)-DM1 | 6 | 1 | 10 | i.v. | Biw * 3 weeks |

TABLE 14-continued

Test ADCs administration and the animal numbers in each group

| Group | Treatment | n | Dose (mg/kg) | Dosing Volume (ul/g) | Dosing Route | Schedule |
|---|---|---|---|---|---|---|
| 5 | W7011-4.87.6-z1-uIgGlk (N-S)-DM1 | 6 | 3 | 10 | i.v. | Biw * 3 weeks |
| 6 | W7011-4.87.6-z1-uIgGlk (N-S)-DM1 | 6 | 10 | 10 | i.v. | Biw * 3 weeks |

7.3 Observations

The protocol and any amendment(s) or procedures involving the care and use of animals in this study will be reviewed and approved by the Institutional Animal Care and Use Committee (IACUC) of WuXi AppTec prior to conduct. During the study, the care and use of animals were conducted in accordance with the regulations of the Association for Assessment and Accreditation of Laboratory Animal Care (AAALAC). After inoculation, the animals were checked daily for morbidity and mortality. At the time of routine monitoring, the animals were checked for any effects of tumor growth and treatments on normal behavior such as mobility, food and water consumption, body weight gain/loss (body weights were measured every day), eye/hair matting and any other abnormal effect. Death and observed clinical signs were recorded on the basis of the numbers of animals within each subset.

7.4 Tumor Measurements and the Endpoints

The major endpoint was to see if the tumor growth could be delayed or mice could be cured. Tumor size was measured twice weekly in two dimensions using a caliper, and the volume was expressed in mm3 using the formula: V=0.5 a×b² where a and b are the long and short diameters of the tumor, respectively. The tumor size was then used for calculations of T/C value and TGI. The T/C value (in percent) is an indication of antitumor effectiveness; T and C are the mean volumes of the treated and control groups, respectively, on Day 21 & Day 28. TGI was calculated for each group using the formula: TGI (%)=[1−($T_i$−$T_0$)/($V_i$−$V_0$)]×100; $T_i$ is the average tumor volume of a treatment group on Day 21 & Day 28, $T_0$ is the average tumor volume of the treatment group on the day of treatment start, $V_i$ is the average tumor volume of the vehicle control group on Day 21 & Day 28, and $V_0$ is the average tumor volume of the vehicle group on the day of treatment start.

All groups were taken down on Day 28 according to the protocol.

All animals kept their body weights well during the experiment period.

7.5 Efficacy Study in Nalm-6 Lymphoma Cancer Xenograft Model

Figure 14:
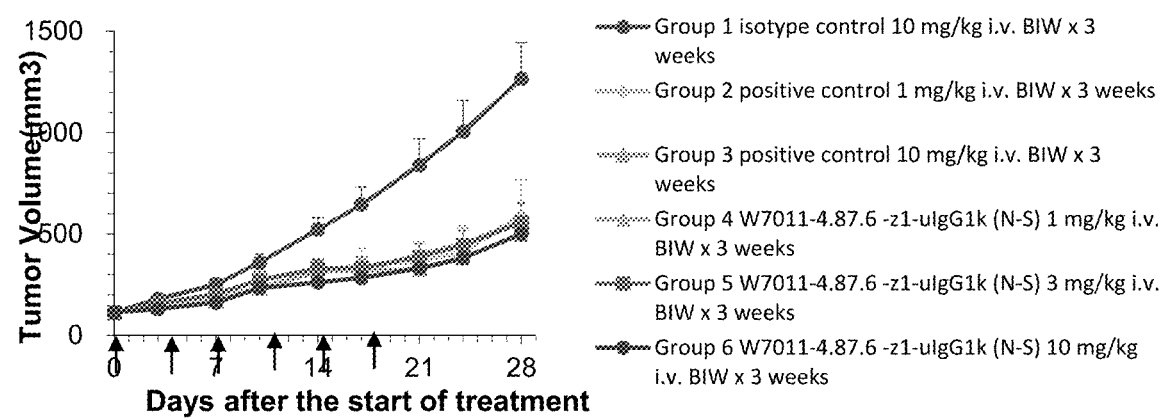
FIG. 14 shows anti-tumor efficacy of benchmark antibody (W7011-BMK1-DM1) and antibody (W7011-4.87.6-z1-uIgGlk (N-S)-DM1), data represents tumor volumes in the different treatment groups of female CB17-SCID mice bearing Nalm-6 lymphoma cancer xenografts. Data points represent as mean+SEM. Arrow represents dosing days

In this study, the efficacy of reference antibody-drug-conjugates W7011-BMK1-DM1 and W7011-4.87.6-z1-uIg-Glk (N-S)-DM1 were evaluated in Nalm-6 lymphoma cancer xenograft in female CB17-SCID mice. Tumor volumes of all groups at various time points are displayed in FIG. 14.

On PG-D21, the mean tumor volume of isotype control treated group reached 840 mm³. Treatment with W7011-BMK1-DM1 at 1 mg/kg (TV=364 mm³, TGI=66%, p<0.01) and 10 mg/kg (TV=327 mm³, TGI=71%, p<0.001) showed significant antitumor activity. ADC W7011-4.87.6-z1-uIg-Glk (N-S)-DM1 at 1 mg/kg (TV=398 mm³, TGI=61%, p<0.01), 3 mg/kg (TV=387 mm³, TGI=62%, p<0.01) and 10 mg/kg (TV=332 mm³, TGI=70%, p<0.001) all showed significant antitumor activity.

After dosing suspension for 1 week, the mean tumor volume of isotype control treated group reached 1266 mm³. Treatment with W7011-BMK1-DM1 at 1 mg/kg (TV=593 mm³, TGI=58%, p<0.01) and 10 mg/kg (TV=499 mm3, TGI=67%, p<0.001) showed significant antitumor activity. ADC W7011-4.87.6-z1-uIgGlk (N-S)-DM1 at 1 mg/kg (TV=562 mm³, TGI=61%, p<0.01), 3 mg/kg (TV=556 mm³, TGI=62%, p<0.01) and 10 mg/kg (TV=502 mm³, TGI=66%, p<0.001) all showed significant antitumor activity.

All animals kept their body weights well during the experiment period.

What is claimed is:

1. An isolated anti-CD19 antibody or an antigen binding fragment thereof, comprising:
 a) heavy chain CDRs 1-3 of SEQ ID NO: 13, SEQ ID NO: 141, and SEQ ID NO: 15, respectively; and kappa light chain CDRs 1-3 of SEQ ID NO: 16, SEQ ID NO: 17, and SEQ ID NO: 18, respectively;
 b) heavy chain CDRs 1-3 of SEQ ID NO: 1, SEQ ID NO: 2, and SEQ ID NO: 3, respectively; and kappa light chain CDRs 1-3 of SEQ ID NO: 4, SEQ ID NO: 5, and SEQ ID NO: 6, respectively;
 c) heavy chain CDRs 1-3 of SEQ ID NO: 7, SEQ ID NO: 8, and SEQ ID NO: 9, respectively; and kappa light chain CDRs 1-3 of SEQ ID NO: 10, SEQ ID NO: 11, and SEQ ID NO: 12, respectively;
 d) heavy chain CDRs 1-3 of SEQ ID NO: 13, SEQ ID NO: 14, and SEQ ID NO: 15, respectively; and kappa light chain CDRs 1-3 of SEQ ID NO: 16, SEQ ID NO: 17, and SEQ ID NO: 18, respectively;
 e) heavy chain CDRs 1-3 of SEQ ID NO: 19, SEQ ID NO: 20, and SEQ ID NO: 21, respectively; and kappa light chain CDRs 1-3 of SEQ ID NO: 4, SEQ ID NO: 5, and SEQ ID NO: 6, respectively;
 f) heavy chain CDRs 1-3 of SEQ ID NO: 22, SEQ ID NO: 23, and SEQ ID NO: 24, respectively; and kappa light chain CDRs 1-3 of SEQ ID NO: 4, SEQ ID NO: 5, and SEQ ID NO: 6, respectively;
 g) heavy chain CDRs 1-3 of SEQ ID NO: 25, SEQ ID NO: 26, and SEQ ID NO: 27, respectively; and kappa light chain CDRs 1-3 of SEQ ID NO: 4, SEQ ID NO: 5, and SEQ ID NO: 6, respectively;
 h) heavy chain CDRs 1-3 of SEQ ID NO: 28, SEQ ID NO: 29, and SEQ ID NO: 30, respectively; and kappa light chain CDRs 1-3 of SEQ ID NO: 4, SEQ ID NO: 5, and SEQ ID NO: 6, respectively;
 i) heavy chain CDRs 1-3 of SEQ ID NO: 31, SEQ ID NO: 32, and SEQ ID NO: 33, respectively; and kappa light chain CDRs 1-3 of SEQ ID NO: 4, SEQ ID NO: 5, and SEQ ID NO: 6, respectively;
 j) heavy chain CDRs 1-3 of SEQ ID NO: 34, SEQ ID NO: 35, and SEQ ID NO: 36, respectively; and kappa light chain CDRs 1-3 of SEQ ID NO: 4, SEQ ID NO: 5, and SEQ ID NO: 6, respectively;
 k) heavy chain CDRs 1-3 of SEQ ID NO: 37, SEQ ID NO: 38, and SEQ ID NO: 39, respectively; and kappa light chain CDRs 1-3 of SEQ ID NO: 40, SEQ ID NO: 41, and SEQ ID NO: 42, respectively;
 l) heavy chain CDRs 1-3 of SEQ ID NO: 43, SEQ ID NO: 44, and SEQ ID NO: 45, respectively; and kappa light chain CDRs 1-3 of SEQ ID NO: 4, SEQ ID NO: 5, and SEQ ID NO: 6, respectively;
 m) heavy chain CDRs 1-3 of SEQ ID NO: 136, SEQ ID NO: 2, and SEQ ID NO: 3, respectively; and kappa light chain CDRs 1-3 of SEQ ID NO: 137, SEQ ID NO: 138, and SEQ ID NO: 139, respectively; or
 n) heavy chain CDRs 1-3 of SEQ ID NO: 7, SEQ ID NO: 140, and SEQ ID NO: 9, respectively; and kappa light chain CDRs 1-3 of SEQ ID NO: 10, SEQ ID NO: 11, and SEQ ID NO: 12, respectively.

2. The antibody or an antigen binding fragment thereof of claim 1, comprising:
 a) a heavy chain variable region comprising SEQ ID NO: 132 and a kappa light chain variable region comprising SEQ ID NO: 134;
 b) a heavy chain variable region comprising SEQ ID NO: 94 and a kappa light chain variable region comprising SEQ ID NO: 96;
 c) a heavy chain variable region comprising SEQ ID NO: 98 and a kappa light chain variable region comprising SEQ ID NO: 100;
 d) a heavy chain variable region comprising SEQ ID NO: 102 and a kappa light chain variable region comprising SEQ ID NO: 104;
 e) a heavy chain variable region comprising SEQ ID NO: 106 and a kappa light chain variable region comprising SEQ ID NO: 96;
 f) a heavy chain variable region comprising SEQ ID NO: 108 and a kappa light chain variable region comprising SEQ ID NO: 96;
 g) a heavy chain variable region comprising SEQ ID NO: 110 and a kappa light chain variable region comprising SEQ ID NO: 96;
 h) a heavy chain variable region comprising SEQ ID NO: 112 and a kappa light chain variable region comprising SEQ ID NO: 96;
 i) a heavy chain variable region comprising SEQ ID NO: 114 and a kappa light chain variable region comprising SEQ ID NO: 96;
 j) a heavy chain variable region comprising SEQ ID NO: 116 and a kappa light chain variable region comprising SEQ ID NO: 96;
 k) a heavy chain variable region comprising SEQ ID NO: 118 and a kappa light chain variable region comprising SEQ ID NO: 120;
 l) a heavy chain variable region comprising SEQ ID NO: 122 and a kappa light chain variable region comprising SEQ ID NO: 96;
 m) a heavy chain variable region comprising SEQ ID NO: 124 and a kappa light chain variable region comprising SEQ ID NO: 126; or
 n) a heavy chain variable region comprising SEQ ID NO: 128 and a kappa light chain variable region comprising SEQ ID NO: 130.

3. The antibody or antigen-binding fragment thereof of claim 1, further comprising an immunoglobulin constant region, optionally a constant region of IgG, optionally a constant region of human IgG1.

4. The antibody or an antigen binding fragment thereof of claim 1, which is a humanized antibody.

5. The antibody or antigen-binding fragment thereof of claim 1, which is a bispecific antibody, a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

6. The antibody or antigen-binding fragment thereof of claim 1 linked to one or more conjugates.

7. An isolated polynucleotide sequence encoding the antibody or an antigen binding fragment thereof of claim 1.

8. A vector comprising the isolated polynucleotide of claim 7.

9. A host cell comprising the vector of claim 8.

10. A method of expressing the antibody or antigen-binding fragment thereof of claim 1, comprising culturing a host cell comprising a vector comprising an isolated polynucleotide sequence encoding the antibody or antigen binding fragment thereof of claim 4 under the condition at which the vector is expressed.

11. An antibody-drug conjugate comprising one or more drug moieties covalently attached to the antibody or antigen-binding fragment of claim 1 either directly or via a linker, wherein the drug moiety is a cytotoxin or a radioactive isotope.

12. A pharmaceutical composition comprising the antibody or antigen-binding fragment thereof of claim 1 or an antibody-drug conjugate comprising one or more drug moieties covalently attached to the antibody or antigen-binding fragment thereof of claim 4, and a pharmaceutically acceptable carrier.

13. A method of treating a CD19 related disease or condition in a subject, comprising administering a therapeutically effective amount of the antibody or antigen-binding fragment thereof of claim 1, or an antibody-drug conjugate comprising one or more drug moieties covalently attached to the antibody or antigen-binding fragment thereof of claim 4 to the subject.

14. A chimeric antigen receptor (CAR) comprising the antigen binding fragment of claim 1 and a T-cell activation moiety, wherein the T-cell activation moiety comprises a transmembrane domain of a T cell receptor and an intracellular signal transduction domain of a T cell receptor.

15. A nucleic acid sequence encoding the CAR of claim 14.

16. A vector comprising the nucleic acid sequence of claim 15.

17. An isolated T cell which expresses the CAR of claim 14.

18. A method for stimulating a T cell-mediated immune response to a CD19 expressing target in a subject, the method comprising administering to the subject an effective amount of the T cell of claim 17.

19. A kit comprising the antibody or antigen-binding fragment thereof of claim 1, useful in detecting presence or amount of CD19 in a sample, or useful in diagnosing a CD19 related disease or condition in a subject.

* * * * *

SEQUENCE LISTING

```
<160> NUMBER OF SEQ ID NOS: 141

<210> SEQ ID NO 1
<211> LENGTH: 10
<212> TYPE: PRT
<213> ORGANISM: Mus musculus

<400> SEQUENCE: 1

Gly Tyr Thr Phe Thr Asn Tyr Val Ile His
1               5                   10

<210> SEQ ID NO 2
<211> LENGTH: 17
<212> TYPE: PRT
<213> ORGANISM: Mus musculus

<400> SEQUENCE: 2

Tyr Phe Asn Pro Tyr Asn Asp Gly Thr Glu Tyr Asn Glu Lys Phe Lys
1               5                   10                  15

Ala
```

```
<210> SEQ ID NO 3
<211> LENGTH: 12
<212> TYPE: PRT
<213> ORGANISM: Mus musculus

<400> SEQUENCE: 3

Gly Pro Tyr Tyr Tyr Gly Ser Ser Pro Phe Asp Tyr
1               5                   10

<210> SEQ ID NO 4
<211> LENGTH: 16
<212> TYPE: PRT
<213> ORGANISM: Mus musculus

<400> SEQUENCE: 4

Arg Ser Ser Gln Ser Leu Glu Asn Ser Asn Gly Asn Thr Tyr Leu Asn
1               5                   10                  15

<210> SEQ ID NO 5
<211> LENGTH: 7
<212> TYPE: PRT
<213> ORGANISM: Mus musculus

<400> SEQUENCE: 5

Arg Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Leu Gln Val Thr His Val Pro Tyr Thr
1               5

<210> SEQ ID NO 7
<211> LENGTH: 10
<212> TYPE: PRT
<213> ORGANISM: Mus musculus

<400> SEQUENCE: 7

Gly Tyr Ala Phe Ser Thr Tyr Trp Met Asn
1               5                   10

<210> SEQ ID NO 8
<211> LENGTH: 17
<212> TYPE: PRT
<213> ORGANISM: Mus musculus

<400> SEQUENCE: 8

Gln Ile Tyr Pro Gly Asp Asp Thr Lys Tyr Asn Gly Lys Phe Lys
1               5                   10                  15

Gly

<210> SEQ ID NO 9
<211> LENGTH: 12
<212> TYPE: PRT
<213> ORGANISM: Mus musculus

<400> SEQUENCE: 9

Arg Tyr Phe Arg Tyr Asp Tyr Trp Tyr Ser Asp Val
1               5                   10
```

```
<210> SEQ ID NO 10
<211> LENGTH: 11
<212> TYPE: PRT
<213> ORGANISM: Mus musculus

<400> SEQUENCE: 10

Arg Ala Ser Gln Asp Ile Ser Asn Tyr Leu Asn
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 9
<212> TYPE: PRT
<213> ORGANISM: Mus musculus

<400> SEQUENCE: 12

His Gln Gly Asn Thr Leu Pro Leu Thr
1               5

<210> SEQ ID NO 13
<211> LENGTH: 10
<212> TYPE: PRT
<213> ORGANISM: Mus musculus

<400> SEQUENCE: 13

Gly Tyr Ala Phe Thr Ser Tyr Asn Met Tyr
1               5                   10

<210> SEQ ID NO 14
<211> LENGTH: 17
<212> TYPE: PRT
<213> ORGANISM: Mus musculus

<400> SEQUENCE: 14

Tyr Ile Asp Pro Tyr Asn Gly Asp Thr Thr Tyr Asn Gln Lys Phe Lys
1               5                   10                  15

Gly

<210> SEQ ID NO 15
<211> LENGTH: 7
<212> TYPE: PRT
<213> ORGANISM: Mus musculus

<400> SEQUENCE: 15

Thr Ala Tyr Ala Met Asp Tyr
1               5

<210> SEQ ID NO 16
<211> LENGTH: 10
<212> TYPE: PRT
<213> ORGANISM: Mus musculus

<400> SEQUENCE: 16

Ser Ala Ser Ser Thr Val Asn Tyr Met His
1               5                   10
```

```
<210> SEQ ID NO 17
<211> LENGTH: 7
<212> TYPE: PRT
<213> ORGANISM: Mus musculus

<400> SEQUENCE: 17

Ser Thr Ser Asn Leu Ala Ser
1               5

<210> SEQ ID NO 18
<211> LENGTH: 9
<212> TYPE: PRT
<213> ORGANISM: Mus musculus

<400> SEQUENCE: 18

His Gln Trp Ser Ser Tyr Pro Tyr Thr
1               5

<210> SEQ ID NO 19
<211> LENGTH: 10
<212> TYPE: PRT
<213> ORGANISM: Mus musculus

<400> SEQUENCE: 19

Gly Tyr Thr Phe Thr Asn Tyr Val Ile His
1               5                   10

<210> SEQ ID NO 20
<211> LENGTH: 17
<212> TYPE: PRT
<213> ORGANISM: Mus musculus

<400> SEQUENCE: 20

Tyr Ile Asn Pro Tyr Asn Asp Gly Thr Glu Tyr Asn Glu Lys Phe Lys
1               5                   10                  15

Gly

<210> SEQ ID NO 21
<211> LENGTH: 12
<212> TYPE: PRT
<213> ORGANISM: Mus musculus

<400> SEQUENCE: 21

Gly Pro Tyr Tyr Tyr Gly Gly Ser Pro Phe Asp Tyr
1               5                   10

<210> SEQ ID NO 22
<211> LENGTH: 10
<212> TYPE: PRT
<213> ORGANISM: Mus musculus

<400> SEQUENCE: 22

Gly Tyr Thr Phe Thr Ser Tyr Val Met His
1               5                   10

<210> SEQ ID NO 23
<211> LENGTH: 17
<212> TYPE: PRT
<213> ORGANISM: Mus musculus

<400> SEQUENCE: 23

Tyr Ile Asn Pro Tyr Asn Asp Gly Thr Glu Tyr His Glu Lys Phe Lys
1               5                   10                  15

Gly
```

<210> SEQ ID NO 24
<211> LENGTH: 12
<212> TYPE: PRT
<213> ORGANISM: Mus musculus

<400> SEQUENCE: 24

Gly Pro Tyr Tyr Tyr Gly Gly Ser Pro Phe Asp Phe
1               5                   10

<210> SEQ ID NO 25
<211> LENGTH: 10
<212> TYPE: PRT
<213> ORGANISM: Mus musculus

<400> SEQUENCE: 25

Gly Tyr Thr Phe Thr Ser Tyr Val Ile His
1               5                   10

<210> SEQ ID NO 26
<211> LENGTH: 17
<212> TYPE: PRT
<213> ORGANISM: Mus musculus

<400> SEQUENCE: 26

Tyr Ile Asn Pro Tyr Asn Asp Gly Ala Glu Tyr Thr Glu Lys Phe Lys
1               5                   10                  15

Gly

<210> SEQ ID NO 27
<211> LENGTH: 12
<212> TYPE: PRT
<213> ORGANISM: Mus musculus

<400> SEQUENCE: 27

Gly Pro Tyr Tyr Tyr Gly Gly Ser Pro Phe Asp Tyr
1               5                   10

<210> SEQ ID NO 28
<211> LENGTH: 10
<212> TYPE: PRT
<213> ORGANISM: Mus musculus

<400> SEQUENCE: 28

Gly Tyr Thr Phe Ser Ser Tyr Val Ile His
1               5                   10

<210> SEQ ID NO 29
<211> LENGTH: 17
<212> TYPE: PRT
<213> ORGANISM: Mus musculus

<400> SEQUENCE: 29

Tyr Ile Asn Pro Tyr Asn Asp Gly Ala Glu Tyr Ala Glu Lys Phe Lys
1               5                   10                  15

Gly

<210> SEQ ID NO 30
<211> LENGTH: 12
<212> TYPE: PRT
<213> ORGANISM: Mus musculus

<400> SEQUENCE: 30

Gly Pro Tyr Tyr Tyr Gly Gly Ser Pro Phe Asp Tyr
1               5                   10

<210> SEQ ID NO 31
<211> LENGTH: 10
<212> TYPE: PRT
<213> ORGANISM: Mus musculus

<400> SEQUENCE: 31

Gly Tyr Thr Phe Thr Ser Tyr Val Ile His
1               5                   10

<210> SEQ ID NO 32
<211> LENGTH: 17
<212> TYPE: PRT
<213> ORGANISM: Mus musculus

<400> SEQUENCE: 32

Tyr Ile Asn Pro Tyr Asn Asp Gly Ala Glu Tyr Asn Glu Lys Phe Lys
1               5                   10                  15

Gly

<210> SEQ ID NO 33
<211> LENGTH: 12
<212> TYPE: PRT
<213> ORGANISM: Mus musculus

<400> SEQUENCE: 33

Gly Pro Tyr Tyr Tyr Gly Ser Ser Pro Phe Asp Tyr
1               5                   10

<210> SEQ ID NO 34
<211> LENGTH: 10
<212> TYPE: PRT
<213> ORGANISM: Mus musculus

<400> SEQUENCE: 34

Gly Tyr Thr Phe Thr Asp Tyr Val Ile His
1               5                   10

<210> SEQ ID NO 35
<211> LENGTH: 17
<212> TYPE: PRT
<213> ORGANISM: Mus musculus

<400> SEQUENCE: 35

Tyr Ile Asn Pro Tyr Asn Asp Gly Ser Glu Tyr Ser Glu Lys Phe Lys
1               5                   10                  15

Gly

<210> SEQ ID NO 36
<211> LENGTH: 12
<212> TYPE: PRT
<213> ORGANISM: Mus musculus

<400> SEQUENCE: 36

Gly Pro Tyr Tyr Tyr Gly Gly Ser Pro Phe Asp Tyr
1               5                   10

<210> SEQ ID NO 37
<211> LENGTH: 10
<212> TYPE: PRT
<213> ORGANISM: Mus musculus

<400> SEQUENCE: 37

Gly Tyr Thr Phe Thr Ser Tyr Val Met His
1               5                   10

<210> SEQ ID NO 38
<211> LENGTH: 17
<212> TYPE: PRT
<213> ORGANISM: Mus musculus

<400> SEQUENCE: 38

Tyr Ile Asn Pro Tyr Asn Asp Gly Thr Lys Tyr Asn Glu Lys Phe Lys
1               5                   10                  15

Gly

<210> SEQ ID NO 39
<211> LENGTH: 12
<212> TYPE: PRT
<213> ORGANISM: Mus musculus

<400> SEQUENCE: 39

Gly Pro Tyr Tyr Tyr Gly Ser Ser Pro Phe Asp Tyr
1               5                   10

<210> SEQ ID NO 40
<211> LENGTH: 16
<212> TYPE: PRT
<213> ORGANISM: Mus musculus

<400> SEQUENCE: 40

Arg Ser Ser Gln Thr Leu Glu Asn Ser Asn Gly Asn Thr Tyr Leu Asn
1               5                   10                  15

<210> SEQ ID NO 41
<211> LENGTH: 7
<212> TYPE: PRT
<213> ORGANISM: Mus musculus

<400> SEQUENCE: 41

Arg Val Ser Asn Arg Phe Ser
1               5

<210> SEQ ID NO 42
<211> LENGTH: 9
<212> TYPE: PRT
<213> ORGANISM: Mus musculus

<400> SEQUENCE: 42

Leu Gln Val Thr His Val Pro Tyr Thr
1               5

<210> SEQ ID NO 43
<211> LENGTH: 10
<212> TYPE: PRT
<213> ORGANISM: Mus musculus

<400> SEQUENCE: 43

Gly Tyr Thr Phe Thr Ser Tyr Val Met His
1               5                   10

<210> SEQ ID NO 44
<211> LENGTH: 17
<212> TYPE: PRT
<213> ORGANISM: Mus musculus

<400> SEQUENCE: 44

Tyr Ile Asn Pro Tyr Asn Asp Gly Thr Gln Tyr Asn Glu Lys Phe Lys
1               5                   10                  15

Gly

<210> SEQ ID NO 45
<211> LENGTH: 12
<212> TYPE: PRT
<213> ORGANISM: Mus musculus

<400> SEQUENCE: 45

Gly Pro Tyr Tyr Tyr Ser Pro Ser Phe Asp Tyr
1               5                   10

<210> SEQ ID NO 46
<211> LENGTH: 25
<212> TYPE: PRT
<213> ORGANISM: Mus musculus

<400> SEQUENCE: 46

Glu Val Gln Leu Gln Gln Ser Gly Pro Glu Leu Val Lys Pro Gly Ala
1               5                   10                  15

Ser Val Lys Met Ser Cys Lys Ala Ser
            20                  25

<210> SEQ ID NO 47
<211> LENGTH: 14
<212> TYPE: PRT
<213> ORGANISM: Mus musculus

<400> SEQUENCE: 47

Trp Val Lys Gln Arg Pro Gly Gln Gly Leu Glu Trp Ile Gly
1               5                   10

<210> SEQ ID NO 48
<211> LENGTH: 32
<212> TYPE: PRT
<213> ORGANISM: Mus musculus

<400> SEQUENCE: 48

Lys Ala Thr Leu Thr Ser Asp Lys Ser Ser Thr Ala Tyr Met Glu
1               5                   10                  15

Leu Ser Ser Leu Thr Ser Glu Asp Ser Ala Val Tyr Tyr Cys Ala Lys
            20                  25                  30

<210> SEQ ID NO 49
<211> LENGTH: 11
<212> TYPE: PRT
<213> ORGANISM: Mus musculus

<400> SEQUENCE: 49

Trp Gly Gln Gly Thr Thr Leu Thr Val Ser Ser
1               5                   10

<210> SEQ ID NO 50
<211> LENGTH: 23
<212> TYPE: PRT
<213> ORGANISM: Mus musculus

<400> SEQUENCE: 50

Asp Ala Val Met Thr Gln Thr Pro Leu Ser Leu Pro Val Ser Leu Gly
1               5                   10                  15

```
Asp Gln Ala Ser Ile Ser Cys
            20

<210> SEQ ID NO 51
<211> LENGTH: 15
<212> TYPE: PRT
<213> ORGANISM: Mus musculus

<400> SEQUENCE: 51

Trp Tyr Gln Gln Lys Pro Gly Gln Ser Pro Lys Leu Leu Ile Tyr
1               5                   10                  15

<210> SEQ ID NO 52
<211> LENGTH: 32
<212> TYPE: PRT
<213> ORGANISM: Mus musculus

<400> SEQUENCE: 52

Gly Val Leu Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Phe Cys
            20                  25                  30

<210> SEQ ID NO 53
<211> LENGTH: 10
<212> TYPE: PRT
<213> ORGANISM: Mus musculus

<400> SEQUENCE: 53

Phe Gly Gly Gly Thr Lys Leu Glu Ile Lys
1               5                   10

<210> SEQ ID NO 54
<211> LENGTH: 25
<212> TYPE: PRT
<213> ORGANISM: Homo sapiens

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 55
<211> LENGTH: 14
<212> TYPE: PRT
<213> ORGANISM: Homo sapiens

<400> SEQUENCE: 55

Trp Val Arg Gln Ala Pro Gly Gln Gly Leu Glu Trp Met Gly
1               5                   10

<210> SEQ ID NO 56
<211> LENGTH: 32
<212> TYPE: PRT
<213> ORGANISM: Homo sapiens

<400> SEQUENCE: 56

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

```
<210> SEQ ID NO 57
<211> LENGTH: 11
<212> TYPE: PRT
<213> ORGANISM: Homo sapiens

<400> SEQUENCE: 57

Trp Gly Gln Gly Thr Thr Val Thr Val Ser Ser
1               5                   10

<210> SEQ ID NO 58
<211> LENGTH: 23
<212> TYPE: PRT
<213> ORGANISM: Homo sapiens

<400> SEQUENCE: 58

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 59
<211> LENGTH: 15
<212> TYPE: PRT
<213> ORGANISM: Homo sapiens

<400> SEQUENCE: 59

Trp Tyr Leu Gln Lys Pro Gly Gln Ser Pro Gln Leu Leu Ile Tyr
1               5                   10                  15

<210> SEQ ID NO 60
<211> LENGTH: 32
<212> TYPE: PRT
<213> ORGANISM: Homo sapiens

<400> SEQUENCE: 60

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 61
<211> LENGTH: 10
<212> TYPE: PRT
<213> ORGANISM: Homo sapiens

<400> SEQUENCE: 61

Phe Gly Gln Gly Thr Lys Leu Glu Ile Lys
1               5                   10

<210> SEQ ID NO 62
<211> LENGTH: 25
<212> TYPE: PRT
<213> ORGANISM: Mus musculus

<400> SEQUENCE: 62

Gln Val Gln Leu Gln Gln Ser Gly Ala Glu Leu Val Arg Pro Gly Ser
1               5                   10                  15

Ser Val Lys Ile Ser Cys Lys Ala Ser
            20                  25

<210> SEQ ID NO 63
<211> LENGTH: 14
<212> TYPE: PRT
```

-continued

<400> SEQUENCE: 63

Trp Val Lys Gln Arg Pro Gly Gln Gly Leu Glu Trp Ile Gly
1               5                   10

<210> SEQ ID NO 64
<211> LENGTH: 32
<212> TYPE: PRT
<213> ORGANISM: Mus musculus

<400> SEQUENCE: 64

Lys Ala Ser Leu Thr Ala Asp Lys Ser Ser Thr Ala Tyr Met Gln
1               5                   10                  15

Leu Ile Ser Leu Thr Ser Glu Asp Ser Ala Val Tyr Phe Cys Ala Arg
            20                  25                  30

<210> SEQ ID NO 65
<211> LENGTH: 11
<212> TYPE: PRT
<213> ORGANISM: Mus musculus

<400> SEQUENCE: 65

Trp Gly Ala Gly Thr Thr Val Thr Val Thr Ser
1               5                   10

<210> SEQ ID NO 66
<211> LENGTH: 23
<212> TYPE: PRT
<213> ORGANISM: Mus musculus

<400> SEQUENCE: 66

Asp Ile Gln Met Thr Gln Thr Thr Ser Ser Leu Ser Ala Ser Leu Gly
1               5                   10                  15

Asp Arg Val Thr Ile Ser Cys
            20

<210> SEQ ID NO 67
<211> LENGTH: 15
<212> TYPE: PRT
<213> ORGANISM: Mus musculus

<400> SEQUENCE: 67

Trp Tyr Gln Gln Lys Pro Asp Gly Thr Val Lys Leu Leu Ile Tyr
1               5                   10                  15

<210> SEQ ID NO 68
<211> LENGTH: 32
<212> TYPE: PRT
<213> ORGANISM: Mus musculus

<400> SEQUENCE: 68

Gly Val Pro Ala Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 69
<211> LENGTH: 10
<212> TYPE: PRT
<213> ORGANISM: Mus musculus

<400> SEQUENCE: 69

Phe Gly Ala Gly Thr Lys Leu Glu Leu Lys

```
<210> SEQ ID NO 70
<211> LENGTH: 25
<212> TYPE: PRT
<213> ORGANISM: Homo sapiens

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 71
<211> LENGTH: 14
<212> TYPE: PRT
<213> ORGANISM: Homo sapiens

<400> SEQUENCE: 71

Trp Val Arg Gln Ala Pro Gly Gln Gly Leu Glu Trp Met Gly
1               5                   10

<210> SEQ ID NO 72
<211> LENGTH: 32
<212> TYPE: PRT
<213> ORGANISM: Homo sapiens

<400> SEQUENCE: 72

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 73
<211> LENGTH: 11
<212> TYPE: PRT
<213> ORGANISM: Homo sapiens

<400> SEQUENCE: 73

Trp Gly Gln Gly Thr Thr Val Thr Val Ser Ser
1               5                   10

<210> SEQ ID NO 74
<211> LENGTH: 23
<212> TYPE: PRT
<213> ORGANISM: Homo sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 75
<211> LENGTH: 15
<212> TYPE: PRT
<213> ORGANISM: Homo sapiens

<400> SEQUENCE: 75

Trp Tyr Gln Gln Lys Pro Gly Lys Val Pro Lys Leu Leu Ile Tyr
1               5                   10                  15

<210> SEQ ID NO 76
```

```
<211> LENGTH: 32
<212> TYPE: PRT
<213> ORGANISM: Homo sapiens

<400> SEQUENCE: 76

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 77
<211> LENGTH: 10
<212> TYPE: PRT
<213> ORGANISM: Homo sapiens

<400> SEQUENCE: 77

Phe Gly Gln Gly Thr Lys Leu Glu Ile Lys
1               5                   10

<210> SEQ ID NO 78
<211> LENGTH: 25
<212> TYPE: PRT
<213> ORGANISM: Mus musculus

<400> SEQUENCE: 78

Glu Ile Gln Leu Gln Gln Ser Gly Pro Glu Leu Val Lys Pro Gly Ala
1               5                   10                  15

Ser Val Lys Val Ser Cys Lys Ala Ser
            20                  25

<210> SEQ ID NO 79
<211> LENGTH: 14
<212> TYPE: PRT
<213> ORGANISM: Mus musculus

<400> SEQUENCE: 79

Trp Val Lys Gln Ser His Gly Lys Ser Leu Glu Trp Ile Gly
1               5                   10

<210> SEQ ID NO 80
<211> LENGTH: 32
<212> TYPE: PRT
<213> ORGANISM: Mus musculus

<400> SEQUENCE: 80

Lys Ala Thr Leu Thr Val Asp Lys Ser Ser Ser Thr Ala Tyr Met His
1               5                   10                  15

Leu Asn Ser Leu Thr Ser Glu Asp Ser Ala Val Tyr Tyr Cys Leu Thr
            20                  25                  30

<210> SEQ ID NO 81
<211> LENGTH: 11
<212> TYPE: PRT
<213> ORGANISM: Mus musculus

<400> SEQUENCE: 81

Trp Gly Gln Gly Thr Ser Val Thr Val Ser Ser
1               5                   10

<210> SEQ ID NO 82
<211> LENGTH: 23
<212> TYPE: PRT
<213> ORGANISM: Mus musculus
```

```
<400> SEQUENCE: 82

Gln Ile Val Leu Thr Gln Ser Pro Ala Ile Met Ser Ala Ser Leu Gly
1               5                   10                  15

Glu Glu Ile Thr Leu Thr Cys
            20

<210> SEQ ID NO 83
<211> LENGTH: 15
<212> TYPE: PRT
<213> ORGANISM: Mus musculus

<400> SEQUENCE: 83

Trp Tyr Gln Gln Lys Ser Gly Thr Ser Pro Lys Leu Leu Ile Tyr
1               5                   10                  15

<210> SEQ ID NO 84
<211> LENGTH: 32
<212> TYPE: PRT
<213> ORGANISM: Mus musculus

<400> SEQUENCE: 84

Gly Val Pro Ser Arg Phe Ser Gly Ser Gly Ser Gly Thr Phe Tyr Ser
1               5                   10                  15

Leu Thr Ile Arg Ser Val Glu Ala Glu Asp Ala Ala Asp Tyr Tyr Cys
            20                  25                  30

<210> SEQ ID NO 85
<211> LENGTH: 10
<212> TYPE: PRT
<213> ORGANISM: Mus musculus

<400> SEQUENCE: 85

Phe Gly Gly Gly Thr Lys Leu Glu Ile Lys
1               5                   10

<210> SEQ ID NO 86
<211> LENGTH: 25
<212> TYPE: PRT
<213> ORGANISM: Homo sapiens

<400> SEQUENCE: 86

Gln Met Gln Leu Val Gln Ser Gly Pro Glu Val Lys Lys Pro Gly Thr
1               5                   10                  15

Ser Val Lys Val Ser Cys Lys Ala Ser
            20                  25

<210> SEQ ID NO 87
<211> LENGTH: 14
<212> TYPE: PRT
<213> ORGANISM: Homo sapiens

<400> SEQUENCE: 87

Trp Val Arg Gln Ala Arg Gly Gln Arg Leu Glu Trp Ile Gly
1               5                   10

<210> SEQ ID NO 88
<211> LENGTH: 32
<212> TYPE: PRT
<213> ORGANISM: Homo sapiens

<400> SEQUENCE: 88

Arg Val Thr Ile Thr Arg Asp Met Ser Thr Ser Thr Ala Tyr Met Glu
1               5                   10                  15
```

Leu Ser Ser Leu Arg Ser Glu Asp Thr Ala Val Tyr Tyr Cys Leu Thr
            20                  25                  30

<210> SEQ ID NO 89
<211> LENGTH: 11
<212> TYPE: PRT
<213> ORGANISM: Homo sapiens

<400> SEQUENCE: 89

Trp Gly Gln Gly Thr Leu Val Thr Val Ser Ser
1               5                   10

<210> SEQ ID NO 90
<211> LENGTH: 23
<212> TYPE: PRT
<213> ORGANISM: Homo sapiens

<400> SEQUENCE: 90

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 91
<211> LENGTH: 15
<212> TYPE: PRT
<213> ORGANISM: Homo sapiens

<400> SEQUENCE: 91

Trp Tyr Gln Gln Lys Pro Gly Lys Ala Pro Lys Leu Leu Ile Tyr
1               5                   10                  15

<210> SEQ ID NO 92
<211> LENGTH: 32
<212> TYPE: PRT
<213> ORGANISM: Homo sapiens

<400> SEQUENCE: 92

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 93
<211> LENGTH: 10
<212> TYPE: PRT
<213> ORGANISM: Homo sapiens

<400> SEQUENCE: 93

Phe Gly Gln Gly Thr Lys Leu Glu Ile Lys
1               5                   10

<210> SEQ ID NO 94
<211> LENGTH: 121
<212> TYPE: PRT
<213> ORGANISM: Mus musculus

<400> SEQUENCE: 94

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
         35                  40                  45

Gly Tyr Phe Asn Pro Tyr Asn Asp Gly Thr Glu Tyr Asn Glu Lys Phe
 50                  55                  60

Lys Ala Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Lys Gly Pro Tyr Tyr Tyr Gly Ser Ser Pro Phe Asp Tyr Trp Gly
                100                 105                 110

Gln Gly Thr Thr Leu Thr Val Ser Ser
        115                 120

<210> SEQ ID NO 95
<211> LENGTH: 363
<212> TYPE: DNA
<213> ORGANISM: Mus musculus

<400> SEQUENCE: 95
gaggtccagc tgcagcagtc tggacctgag ctggtaaagc ctggggcttc agtgaagatg    60
tcctgcaagg cttctggata cacattcact aactatgtta ttcactgggt gaagcagaag   120
cctgggcagg gccttgagtg gattggatat tttaatcctt acaatgatgg tactgaatac   180
aatgagaagt tcaagccaa ggccacactg acttcagaca atcctccag cacagcctac   240 atggagctca gcagcctgac ctctgaggac tctgcggtct attactgtgc aaaaggtccc   300
tactactacg gtagtagccc ctttgactac tggggccaag gcaccactct cacagtctcc   360
tca                                                                 363

<210> SEQ ID NO 96
<211> LENGTH: 112
<212> TYPE: PRT
<213> ORGANISM: Mus musculus

<400> SEQUENCE: 96

Asp Ala Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Glu Asn Ser
             20                  25                  30

Asn Gly Asn Thr Tyr Leu Asn Trp Tyr Leu Gln Lys Pro Gly Gln Ser
         35                  40                  45

Pro Gln Leu Leu Ile Tyr Arg Val Ser Asn Arg Phe Ser Gly Val Leu
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Leu Gln Val
                 85                  90                  95

Thr His Val Pro Tyr Thr Phe Gly Gly Gly Thr Lys Leu Glu Ile Lys
                100                 105                 110

<210> SEQ ID NO 97
<211> LENGTH: 336
<212> TYPE: DNA
<213> ORGANISM: Mus musculus

<400> SEQUENCE: 97
gatgctgtga tgacccaaac tccactctcc ctgcctgtca gtcttggaga tcaagcctcc    60

-continued

```
atctcttgca ggtctagtca gagccttgaa aacagtaatg gaaacaccta tttgaactgg      120
tacctccaga aaccaggcca gtctccacag ctcctgatct acagggtttc caaccgattt      180 tctgggtcc ttgacaggtt cagtggtagt ggatcaggga cagatttcac actgaaaatc       240
agtagagtgg aggctgagga tttgggagtt tatttctgtc tccaagttac acatgtcccg      300
tacacgttcg gaggggggac caagctggaa ataaaa                                336
```

<210> SEQ ID NO 98
<211> LENGTH: 121
<212> TYPE: PRT
<213> ORGANISM: Mus musculus

<400> SEQUENCE: 98

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Thr Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Asp Asp Thr Lys Tyr Asn Gly Lys Phe
    50                  55                  60

Lys Gly Lys Ala Ser Leu Thr Ala Asp Lys Ser Ser Thr Ala Tyr
65                  70                  75                  80

Met Gln Leu Ile Ser Leu Thr Ser Glu Asp Ser Ala Val Tyr Phe Cys
                85                  90                  95

Ala Arg Arg Tyr Phe Arg Tyr Asp Tyr Trp Tyr Ser Asp Val Trp Gly
            100                 105                 110

Ala Gly Thr Thr Val Thr Val Thr Ser
        115                 120
```

<210> SEQ ID NO 99
<211> LENGTH: 363
<212> TYPE: DNA
<213> ORGANISM: Mus musculus

<400> SEQUENCE: 99

```
caggttcaac tgcagcagtc tggggctgag ctggtgaggc ctgggtcctc agtgaagatt       60
tcctgcaagg cttctggcta tgcattcagt acctattgga tgaactgggt gaagcagagg      120
cctggacagg gtcttgagtg gattggacag atttatcctg gagatgatga tactaagtac      180
aatggaaagt tcaagggtaa agcctcactg actgcagaca atcctccag caccgcctac       240 atgcagctca tcagcctaac atctgaggac tctgcggtct atttctgtgc aagaagatac      300
tttaggtacg actactggta ttccgatgtc tggggcgcag ggaccacggt caccgtcacc      360
tca                                                                    363
```

<210> SEQ ID NO 100
<211> LENGTH: 107
<212> TYPE: PRT
<213> ORGANISM: Mus musculus

<400> SEQUENCE: 100

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
```

```
              35                  40                  45
Tyr Tyr Thr Ser Arg Leu His Ser Gly Val Pro Ala Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys His Gln Gly Asn Thr Leu Pro Leu
                 85                  90                  95

Thr Phe Gly Ala Gly Thr Lys Leu Glu Leu Lys
            100                 105

<210> SEQ ID NO 101
<211> LENGTH: 321
<212> TYPE: DNA
<213> ORGANISM: Mus musculus

<400> SEQUENCE: 101
gatatccaga tgacacagac tacatcctcc ctgtctgcct ctctgggaga cagagtcacc    60
atcagttgca gggcaagtca ggacattagc aattatttaa actggtatca gcagaaaccg   120
gatggaactg ttaaactcct gatctattac acatcaagat tacactcagg agtcccagca   180
agattcagtg gcagtgggtc tggaacagat tactctctca ccattagtaa cctggaacaa   240
gaagatattg ccacttactt ttgccaccag ggtaatacgc ttccgctcac gttcggtgct   300
gggaccaagc tggagctgaa a                                             321

<210> SEQ ID NO 102
<211> LENGTH: 116
<212> TYPE: PRT
<213> ORGANISM: Mus musculus

<400> SEQUENCE: 102

Glu Ile Gln Leu Gln Gln Ser Gly Pro Glu Leu Val Lys Pro Gly Ala
  1               5                  10                  15

Ser Val Lys Val Ser Cys Lys Ala Ser Gly Tyr Ala Phe Thr Ser Tyr
             20                  25                  30

Asn Met Tyr Trp Val Lys Gln Ser His Gly Lys Ser Leu Glu Trp Ile
         35                  40                  45

Gly Tyr Ile Asp Pro Tyr Asn Gly Asp Thr Thr Tyr Asn Gln Lys Phe
 50                  55                  60

Lys Gly Lys Ala Thr Leu Thr Val Asp Lys Ser Ser Ser Thr Ala Tyr
 65                  70                  75                  80

Met His Leu Asn Ser Leu Thr Ser Glu Asp Ser Ala Val Tyr Tyr Cys
                 85                  90                  95

Leu Thr Thr Ala Tyr Ala Met Asp Tyr Trp Gly Gln Gly Thr Ser Val
            100                 105                 110

Thr Val Ser Ser
        115

<210> SEQ ID NO 103
<211> LENGTH: 348
<212> TYPE: DNA
<213> ORGANISM: Mus musculus

<400> SEQUENCE: 103
gagatccagc tgcagcagtc tggacctgag ctggtgaagc ctggggcttc agtgaaggta    60
tcctgcaagg cttctggtta tgcattcact agctacaaca tgtactgggt gaagcagagc   120
catggaaaga gccttgagtg gattggatat attgatcctt acaatggtga tactacctac   180
```

```
aaccagaagt tcaagggcaa ggccacattg actgttgaca agtcctccag cacagcctac    240
atgcatctca acagcctgac atctgaggac tctgcagtct attactgtct cactacggcc    300
tatgctatgg actactgggg tcaaggaacc tcagtcaccg tctcctca                 348
```

<210> SEQ ID NO 104
<211> LENGTH: 106
<212> TYPE: PRT
<213> ORGANISM: Mus musculus

<400> SEQUENCE: 104

```
Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Thr Val Asn Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Arg Ser Val Glu Ala Glu
65                  70                  75                  80

Asp Ala Ala Asp Tyr Tyr Cys His Gln Trp Ser Ser Tyr Pro Tyr Thr
                85                  90                  95

Phe Gly Gly Gly Thr Lys Leu Glu Ile Lys
            100                 105
```

<210> SEQ ID NO 105
<211> LENGTH: 318
<212> TYPE: DNA
<213> ORGANISM: Mus musculus

<400> SEQUENCE: 105

```
caaattgttc tcacccagtc tccagcaatc atgtctgcat ctctagggga ggagatcacc     60
ctaacctgca gtgccagctc gactgtaaat tacatgcact ggtaccagca gaagtcaggc    120
acttctccca aactcttgat ttatagcaca tccaacctgg cttctggagt cccttctcgc    180
ttcagtggca gtgggtctgg gaccttttat tctctcacaa tcagaagtgt ggaggctgaa    240
gatgctgccg attattactg ccatcagtgg agtagttatc cgtacacgtt cggaggggggg   300 accaagctgg aaataaaa                                                 318
```

<210> SEQ ID NO 106
<211> LENGTH: 121
<212> TYPE: PRT
<213> ORGANISM: Mus musculus

<400> SEQUENCE: 106

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Thr Glu Tyr Asn Glu Lys Phe
    50                  55                  60

Lys Gly Lys Ala Thr Leu Thr Ser Asp Thr Ser Ser Thr Ala Tyr
65                  70                  75                  80
```

```
Met Ala Leu Ser Ser Leu Thr Ser Glu Asp Ser Ala Val Tyr Tyr Cys
                85                  90                  95

Thr Arg Gly Pro Tyr Tyr Tyr Gly Gly Ser Pro Phe Asp Tyr Trp Gly
            100                 105                 110

Gln Gly Thr Thr Leu Thr Val Ser Ser
        115                 120

<210> SEQ ID NO 107
<211> LENGTH: 363
<212> TYPE: DNA
<213> ORGANISM: Mus musculus

<400> SEQUENCE: 107
gaggtccagc tgcagcagtc tggacctgag ctggtaaagc ctggggcttc agtgaagatg      60
tcctgcaagg cttctggata cacattcact aactatgtta tacactgggt gaagcagaag     120
cctgggcagg gccttgagtg gattggatat attaatcctt acaatgatgg tactgagtac     180
aatgagaagt tcaaaggcaa ggccacactg acttcagaca catcctccag cacagcctac     240
atggcgctca gcagcctgac ctctgaggac tctgcggtct attactgtac aagaggaccc     300
tattactacg gtggtagccc cttcgactac tggggccaag gcaccactct cacagtctcc     360
tca                                                                   363

<210> SEQ ID NO 108
<211> LENGTH: 121
<212> TYPE: PRT
<213> ORGANISM: Mus musculus

<400> SEQUENCE: 108

Glu Val Gln Leu Gln Gln Ser Gly Pro Glu Leu Val Lys Pro Gly Ala
1               5                  10                  15

Ser Val Lys Met Ser Cys Lys Ala Ser Gly Tyr Thr Phe Thr Ser Tyr
            20                  25                  30

Val Met His Trp Met Lys Gln Lys Pro Gly Gln Gly Leu Glu Trp Ile
        35                  40                  45

Gly Tyr Ile Asn Pro Tyr Asn Asp Gly Thr Glu Tyr His Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Phe Tyr Cys
                85                  90                  95

Ala Arg Gly Pro Tyr Tyr Tyr Gly Gly Ser Pro Phe Asp Phe Trp Gly
            100                 105                 110

Gln Gly Thr Thr Leu Thr Val Ser Ser
        115                 120

<210> SEQ ID NO 109
<211> LENGTH: 363
<212> TYPE: DNA
<213> ORGANISM: Mus musculus

<400> SEQUENCE: 109
gaggtccagc tgcagcagtc tgggcctgag ctggtaaagc ctggggcttc agtgaagatg      60
tcctgcaagg cttctggata cacattcact agctatgtta tgcactggat gaaacagaag     120
cctgggcagg gccttgagtg gattggatat attaatcctt acaatgatgg tactgagtac     180
catgagaagt tcaaaggcaa ggccacactg acttcagaca atcctccag cacagcctac      240
```

```
atggagctca gcagcctgac ctctgaggac tctgcggtct tttactgtgc aagaggaccc    300
tattactacg gtggtagccc ctttgacttc tggggccaag gcaccactct cacggtctcc    360
tca                                                                  363
```

<210> SEQ ID NO 110
<211> LENGTH: 121
<212> TYPE: PRT
<213> ORGANISM: Mus musculus

<400> SEQUENCE: 110

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ala Glu Tyr Thr Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Thr Val Tyr Tyr Cys
                85                  90                  95

Ala Arg Gly Pro Tyr Tyr Tyr Gly Gly Ser Pro Phe Asp Tyr Trp Gly
            100                 105                 110

Gln Gly Thr Thr Leu Thr Val Ser Ser
        115                 120
```

<210> SEQ ID NO 111
<211> LENGTH: 363
<212> TYPE: DNA
<213> ORGANISM: Mus musculus

<400> SEQUENCE: 111

```
gaggtccagc tgcagcagtc tggacctgag ctggtaaagc ctggggcttc agtgaagatg    60
tcctgcaagg cttctggata cacattcact agctatgtta tacactgggt gaagcagaag    120
cctgggcagg gccttgagtg gattggatat attaatcctt acaatgatgg tgctgagtac    180
actgagaagt tcaagggcaa ggccacactg acttcagaca atcctccag tactgcctat    240 atggagctca gcagcctgac ctctgaggac tctacggtct attactgtgc acgaggaccc    300
tattactacg gtggtagccc ctttgactac tggggccaag gcaccactct cacagtctcc    360
tca                                                                  363
```

<210> SEQ ID NO 112
<211> LENGTH: 121
<212> TYPE: PRT
<213> ORGANISM: Mus musculus

<400> SEQUENCE: 112

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Ser Ser Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ala Glu Tyr Ala Glu Lys Phe
    50                  55                  60
```

```
Lys Gly Lys Ala Thr Leu Thr Ser Asp Lys Ser Ser Ser Ala Tyr
65                  70                  75                  80

Met Glu Leu Gly Ser Leu Thr Ser Glu Asp Ser Ala Val Tyr Tyr Cys
                85                  90                  95

Ala Arg Gly Pro Tyr Tyr Tyr Gly Gly Ser Pro Phe Asp Tyr Trp Gly
            100                 105                 110

Gln Gly Thr Thr Leu Thr Val Ser Ser
        115                 120
```

<210> SEQ ID NO 113
<211> LENGTH: 363
<212> TYPE: DNA
<213> ORGANISM: Mus musculus

<400> SEQUENCE: 113

```
gaggtccagc tgcagcagtc tggacctgag ctggtaaagc ctggggcttc agtgaagatg      60
tcctgcaagg cttctggata cacattcagt agttatgtta tacactgggt gaagcagaag    120
cctgggcagg gccttgagtg gattggatat attaatcctt acaatgatgg tgctgagtat    180
gctgagaagt tcaagggcaa ggccacactg acttcagaca atcctccagt ttctgcctat    240
atggagctcg gcagcctgac ctctgaggac tctgcggtct attactgtgc acgaggaccc    300
tattactacg gtggtagtcc ctttgactac tggggccaag caccactctc acagtctcc    360 tca                                                                   363
```

<210> SEQ ID NO 114
<211> LENGTH: 121
<212> TYPE: PRT
<213> ORGANISM: Mus musculus

<400> SEQUENCE: 114

```
Glu Val Gln Leu Gln Gln Ser Gly Pro Glu Leu Val Lys Pro Gly Ala
1               5                   10                  15

Ser Val Glu Met Ser Cys Lys Ala Ser Gly Tyr Thr Phe Thr Ser Tyr
            20                  25                  30

Val Ile His Trp Leu Lys Gln Lys Pro Gly Gln Gly Leu Glu Trp Ile
        35                  40                  45

Gly Tyr Ile Asn Pro Tyr Asn Asp Gly Ala Glu Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Gly Pro Tyr Tyr Tyr Gly Ser Ser Pro Phe Asp Tyr Trp Gly
            100                 105                 110

Gln Gly Thr Thr Leu Thr Val Ser Ser
        115                 120
```

<210> SEQ ID NO 115
<211> LENGTH: 363
<212> TYPE: DNA
<213> ORGANISM: Mus musculus

<400> SEQUENCE: 115

```
gaggtccagc tgcagcagtc tggacctgag ctggtgaagc ctggggcttc agtggagatg      60
tcctgcaagg cttctggata cacattcact agctatgtta ttcactggtt gaagcagaag    120
```

```
cctgggcagg gccttgagtg gattggatat attaatcctt acaatgatgg tgctgagtat    180
aatgagaagt tcaagggcaa ggccacactg acttcagaca atcctccag tacagcctat     240 atggatctca acagcctgac ctctgaggac tctgcggtct attactgtgc aagaggaccc   300
tattactacg gtagtagccc ctttgactac tggggccaag gcaccactct cacagtctcc    360
tca                                                                  363
```

<210> SEQ ID NO 116
<211> LENGTH: 121
<212> TYPE: PRT
<213> ORGANISM: Mus musculus

<400> SEQUENCE: 116

```
Glu Val Gln Leu Leu Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile His Trp Val Lys Gln Arg Pro Gly Gln Gly Leu Glu Trp Ile
        35                  40                  45

Gly Tyr Ile Asn Pro Tyr Asn Asp Gly Ser Glu Tyr Ser Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Pro Tyr Tyr Tyr Gly Gly Ser Pro Phe Asp Tyr Trp Gly
            100                 105                 110

Gln Gly Thr Thr Leu Thr Val Ser Ser
        115                 120
```

<210> SEQ ID NO 117
<211> LENGTH: 363
<212> TYPE: DNA
<213> ORGANISM: Mus musculus

<400> SEQUENCE: 117

```
gaggtccagc tgctgcagtc tggacctgag ctggtaaagc ctggggcttc agtgaagatg   60
tcctgcaagg cttctggata cacattcact gactatgtta tacactgggt gaagcagagg  120
cctgggcagg gccttgagtg gattggatat attaatcctt acaatgatgg ttctgagtac  180
agtgagaagt tcaaaggcaa ggccacactg acttcagaca atcctccag cacagcctac   240 atggagctca gcagcctgac ctctgaggac tctgcggtct attactgtgc aagaggaccc  300
tattactacg gtggtagtcc ctttgactac tggggccaag gcaccactct cacagtctcc   360
tca                                                                  363
```

<210> SEQ ID NO 118
<211> LENGTH: 121
<212> TYPE: PRT
<213> ORGANISM: Mus musculus

<400> SEQUENCE: 118

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
```

```
            35                  40                  45
Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Gly Pro Tyr Tyr Tyr Gly Ser Ser Pro Phe Asp Tyr Trp Gly
                100                 105                 110

Gln Gly Thr Thr Leu Thr Val Ser Ser
            115                 120

<210> SEQ ID NO 119
<211> LENGTH: 363
<212> TYPE: DNA
<213> ORGANISM: Mus musculus

<400> SEQUENCE: 119
gaggtccagc tgcagcagtc tggacctgag ctggtaaagc ctggggcttc agtgaagatg     60
tcctgcaagg cttctggata cacattcact agctatgtta tgcactgggt gaagcagaag    120
cctgggcagg gccttgagtg gattggatat attaatcctt acaatgatgg tactaagtac    180
aatgagaagt tcaaaggcaa ggccacactg acttcagaca atcctccag cacagcctac    240 atggaactca gcagcctgac ctctgaggac tctgcggtct attactgtgc aagaggaccc    300
tattactacg gtagtagccc ctttgactac tggggccaag gcaccactct cacagtctcc    360
tca                                                                  363

<210> SEQ ID NO 120
<211> LENGTH: 112
<212> TYPE: PRT
<213> ORGANISM: Mus musculus

<400> SEQUENCE: 120

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Thr Leu Glu Asn Ser
                 20                  25                  30

Asn Gly Asn Thr Tyr Leu Asn Trp Tyr Leu Gln Lys Pro Gly Gln Ser
             35                  40                  45

Pro Gln Leu Leu Ile Tyr Arg Val Ser Asn Arg Phe Ser Gly Val Leu
 50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Leu Gly Val Tyr Phe Cys Leu Gln Val
                 85                  90                  95

Thr His Val Pro Tyr Thr Phe Gly Gly Gly Thr Lys Leu Glu Ile Lys
                100                 105                 110

<210> SEQ ID NO 121
<211> LENGTH: 336
<212> TYPE: DNA
<213> ORGANISM: Mus musculus

<400> SEQUENCE: 121
gatgctgtga tgacccaaac tccactctcc ctgcctgtca gtcttggaga tcaagcctcc     60
atctcttgca ggtctagtca gaccctttgaa aacagtaatg gaaacaccta tttgaactgg    120
```

```
tacctccaga aaccaggcca gtctccacag ctcctgatct acagggtttc caaccgattt      180
tctggggtcc tagacaggtt cagtggtagt ggatcaggga cagatttcac actgaaaatc      240
agcagagtgg agactgagga tttgggagtt tatttctgcc tccaagttac acatgtcccg      300
tacacgttcg gaggggggac caagctggaa ataaaa                                336
```

<210> SEQ ID NO 122
<211> LENGTH: 121
<212> TYPE: PRT
<213> ORGANISM: Mus musculus

<400> SEQUENCE: 122

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Gln Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Pro Tyr Tyr Tyr Ser Pro Ser Pro Phe Asp Tyr Trp Gly
            100                 105                 110

Gln Gly Thr Thr Leu Thr Val Ser Ser
        115                 120
```

<210> SEQ ID NO 123
<211> LENGTH: 363
<212> TYPE: DNA
<213> ORGANISM: Mus musculus

<400> SEQUENCE: 123

```
gaggtccagc tgcagcagtc tggacctgag ctggtaaagc ctggggcttc agtgaagatg      60
tcctgcaagg cttctggata cacattcact agctatgtca tgcactgggt gaagcagaag      120
cctgggcagg gccttgagtg gattggatat attaatcctt acaatgatgg tactcagtac      180
aatgagaagt ttaaaggcaa ggccacactg acttcagaca atcctccag cacagcctac       240 atggagctca gcagcctgac ctctgaggac tctgcggtct attactgtgc aagaggaccc      300
tattactaca gtcctagccc ctttgactac tggggccaag caccactct cacagtctcc       360 tca                                                                    363
```

<210> SEQ ID NO 124
<211> LENGTH: 121
<212> TYPE: PRT
<213> ORGANISM: Artificial Sequence
<220> FEATURE:
<223> OTHER INFORMATION: Synthetic

<400> SEQUENCE: 124

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30
```

Val Ile His Trp Val Arg Gln Ala Pro Gly Gln Gly Leu Glu Trp Met
        35                  40                  45

Gly Tyr Phe Asn Pro Tyr Asn Asp Gly Thr Glu Tyr Asn Glu Lys Phe
 50                  55                  60

Lys Ala Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Pro Tyr Tyr Tyr Gly Ser Ser Pro Phe Asp Tyr Trp Gly
                100                 105                 110

Gln Gly Thr Thr Val Thr Val Ser Ser
            115                 120

<210> SEQ ID NO 125
<211> LENGTH: 363
<212> TYPE: DNA
<213> ORGANISM: Artificial Sequence
<220> FEATURE:
<223> OTHER INFORMATION: Synthetic

<400> SEQUENCE: 125
caggtgcagc ttgtgcagtc tggagctgaa gtgaagaagc caggatcctc cgtgaaggtc      60
tcctgtaagg cttctggcta caccttcacc gattacgtga tccactgggt caggcaggcc     120
cctgggcaag gcttggagtg gatggggtac tttaaccccct acaacgatgg gactgagtac    180
aatgagaagt ttaaagcacg ggtgaccatt accgccgaca agagcacaag cacagcctac    240
atggagctgt ccagcctccg cagcgaggat acagccgtct actactgcgc cagaggcccct    300 tactactatg gtccagccc cttcgactat tggggccagg ggactacagt gactgtcagt     360
tca                                                                 363

<210> SEQ ID NO 126
<211> LENGTH: 112
<212> TYPE: PRT
<213> ORGANISM: Artificial Sequence
<220> FEATURE:
<223> OTHER INFORMATION: Synthetic

<400> SEQUENCE: 126

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Glu Asn Ser
                 20                  25                  30

Asn His Asn Thr Tyr Ile Asn Trp Tyr Leu Gln Lys Pro Gly Gln Ser
             35                  40                  45

Pro Gln Leu Leu Ile Tyr Arg Val Ser Lys Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys His Gln Val
                 85                  90                  95

Thr His Val Pro Tyr Thr Phe Gly Gln Gly Thr Lys Leu Glu Ile Lys
            100                 105                 110

<210> SEQ ID NO 127
<211> LENGTH: 336
<212> TYPE: DNA
<213> ORGANISM: Artificial Sequence
<220> FEATURE:

<223> OTHER INFORMATION: Synthetic

<400> SEQUENCE: 127

```
gatatcgtga tgacccagac tcccctgtcc cttcctgtga ccccaggaga accagcttct    60
atcagctgta ggtcctcaca gagcctggag aactccaacc acaacaccta cataaactgg   120
tacctccaga agcctgggca gtctccccag ttgctgatct acagggtcag caaacgcttc   180
tccggggtgc ccgatcggtt tagtgggagc gggagcggca cagactttac actcaagatt   240
tccagagtgg aggccgagga cgtcggcgtc tattactgcc accaagtgac acacgtgccc   300
tacacattcg gccagggcac taaactggag attaag                             336
```

<210> SEQ ID NO 128
<211> LENGTH: 121
<212> TYPE: PRT
<213> ORGANISM: Artificial Sequence
<220> FEATURE:
<223> OTHER INFORMATION: Synthetic

<400> SEQUENCE: 128

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ala Phe Ser Thr Tyr
                20                  25                  30
Trp Met Asn Trp Val Arg Gln Ala Pro Gly Gln Gly Leu Glu Trp Met
            35                  40                  45
Gly Gln Ile Tyr Pro Gly Asp Asp Asp Thr Lys Tyr Ser Gly Lys Phe
        50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Tyr Phe Arg Tyr Asp Tyr Trp Tyr Ser Asp Val Trp Gly
                100                 105                 110
Gln Gly Thr Thr Val Thr Val Ser Ser
        115                 120
```

<210> SEQ ID NO 129
<211> LENGTH: 363
<212> TYPE: DNA
<213> ORGANISM: Artificial Sequence
<220> FEATURE:
<223> OTHER INFORMATION: Synthetic

<400> SEQUENCE: 129

```
caggtccagc ttgtccagtc tggagcagaa gtgaagaagc caggggcttc agtgaaggtg    60
tcttgcaagg cttccggata cgccttctcc acttactgga tgaactgggt gcgccaggcc   120
cctgggcagg gcttggagtg gatgggccag atctatcccg gcgatgacga cacaaaatac   180
agcgggaagt tcaaggggcg ggtgaccatt accgccgata aaagcacctc caccgcctac   240
atggagctca gttccctgag aagcgaggat acagccgtgt actactgtgc caggaggtac   300
tttcggtacg actactggta tagcgacgtc tggggggcaag gcacaactgt cacagtgagc   360
agc                                                                 363
```

<210> SEQ ID NO 130
<211> LENGTH: 107
<212> TYPE: PRT
<213> ORGANISM: Artificial Sequence
<220> FEATURE:
<223> OTHER INFORMATION: Synthetic

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His Gln Gly Asn Thr Leu Pro Leu
                85                  90                  95

Thr Phe Gly Gln Gly Thr Lys Leu Glu Ile Lys
            100                 105

<210> SEQ ID NO 131
<211> LENGTH: 321
<212> TYPE: DNA
<213> ORGANISM: Artificial Sequence
<220> FEATURE:
<223> OTHER INFORMATION: Synthetic

<400> SEQUENCE: 131
gacatccaaa tgacccagag cccttcctcc ttgtccgcaa gtgtgggaga tagagtgacc        60
atcacctgca gggcttctca ggatatctcc aactacctga actggtatca gcagaagccc       120
ggcaaggtgc caaagctcct tatttactac acctcccggc tgcacagcgg agtcccatct       180
cgcttcagcg gtcaggcag cggcactgac tttactctga caattagcag cctccagcct        240
gaagacgtcg ccacttacta ctgtcatcag gggaatacac tccccctgac attcgggcag       300
gggacaaaac tggagattaa g                                                 321

<210> SEQ ID NO 132
<211> LENGTH: 116
<212> TYPE: PRT
<213> ORGANISM: Artificial Sequence
<220> FEATURE:
<223> OTHER INFORMATION: Synthetic

<400> SEQUENCE: 132

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ala Phe Thr Ser Tyr
            20                  25                  30

Asn Met Tyr Trp Val Arg Gln Ala Arg Gly Gln Arg Leu Glu Trp Ile
        35                  40                  45

Gly Tyr Ile Asp Pro Tyr Asn Ala Asp Thr Thr Tyr Asn Gln Lys Phe
50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Thr Thr Ala Tyr Ala Met Asp Tyr Trp Gly Gln Gly Thr Leu Val
            100                 105                 110

```
Thr Val Ser Ser
        115

<210> SEQ ID NO 133
<211> LENGTH: 348
<212> TYPE: DNA
<213> ORGANISM: Artificial Sequence
<220> FEATURE:
<223> OTHER INFORMATION: Synthetic

<400> SEQUENCE: 133
caaatgcagc tcgtccagtc tggacctgaa gtgaagaagc ccggacatc cgtcaaggtc      60 tcatgtaagg ctagcgggta cgcattcact tcctacaaca tgtactgggt gcgccaggcc     120
agaggacaga ggttggagtg gatcggctac atcgacccat acaacgccga tactacctac     180
aatcagaagt ttaaagggcg ggtgaccatt acccgggata tgtccacctc caccgcctac     240
atggagctga gcagcctgag gagcgaggac acagccgtgt actactgcct gacaacagcc     300
tatgccatgg actattgggg ccagggcaca cttgtgactg tgagcagt                  348

<210> SEQ ID NO 134
<211> LENGTH: 106
<212> TYPE: PRT
<213> ORGANISM: Artificial Sequence
<220> FEATURE:
<223> OTHER INFORMATION: Synthetic

<400> SEQUENCE: 134

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Thr Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Ser Ser Tyr Pro Tyr Thr
                85                  90                  95

Phe Gly Gln Gly Thr Lys Leu Glu Ile Lys
            100                 105

<210> SEQ ID NO 135
<211> LENGTH: 318
<212> TYPE: DNA
<213> ORGANISM: Artificial Sequence
<220> FEATURE:
<223> OTHER INFORMATION: Synthetic

<400> SEQUENCE: 135
gacatccagc tcacccaatc cccttctttc ctctccgcaa gtgtcggaga tagggtgact      60
atcacctgct cagcttcttc aaccgtgaac tacatgcatt ggtaccagca gaagcccggg     120
aaagccccaa agctgctgat ctacagcacc tccaatctgg ccagtggagt gccaagccgg     180
tttagcggga gcggctccgg cactgaattc actttgacaa ttagcagcct tcagcctgag     240
gactttgcca catattactg tcaccagtgg tccagctacc cctacacatt cgggcagggc     300
acaaagctgg agattaag                                                   318
```

<210> SEQ ID NO 136
<211> LENGTH: 10
<212> TYPE: PRT
<213> ORGANISM: Artificial Sequence
<220> FEATURE:
<223> OTHER INFORMATION: Synthetic

<400> SEQUENCE: 136

Gly Tyr Thr Phe Thr Asp Tyr Val Ile His
1               5                   10

<210> SEQ ID NO 137
<211> LENGTH: 16
<212> TYPE: PRT
<213> ORGANISM: Artificial Sequence
<220> FEATURE:
<223> OTHER INFORMATION: Synthetic

<400> SEQUENCE: 137

Arg Ser Ser Gln Ser Leu Glu Asn Ser Asn His Asn Thr Tyr Ile Asn
1               5                   10                  15

<210> SEQ ID NO 138
<211> LENGTH: 7
<212> TYPE: PRT
<213> ORGANISM: Artificial Sequence
<220> FEATURE:
<223> OTHER INFORMATION: Synthetic

<400> SEQUENCE: 138

Arg Val Ser Lys Arg Phe Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic

<400> SEQUENCE: 139

His Gln Val Thr His Val Pro Tyr Thr
1               5

<210> SEQ ID NO 140
<211> LENGTH: 17
<212> TYPE: PRT
<213> ORGANISM: Artificial Sequence
<220> FEATURE:
<223> OTHER INFORMATION: Synthetic

<400> SEQUENCE: 140

Gln Ile Tyr Pro Gly Asp Asp Asp Thr Lys Tyr Ser Gly Lys Phe Lys
1               5                   10                  15

Gly

<210> SEQ ID NO 141
<211> LENGTH: 17
<212> TYPE: PRT
<213> ORGANISM: Artificial Sequence
<220> FEATURE:
<223> OTHER INFORMATION: Synthetic

```
<400> SEQUENCE: 141

Tyr Ile Asp Pro Tyr Asn Ala Asp Thr Thr Tyr Asn Gln Lys Phe Lys
1               5                   10                  15
Gly
```